(12) United States Patent
Schimmer et al.

(10) Patent No.: US 8,008,354 B2
(45) Date of Patent: Aug. 30, 2011

(54) DEATH RECEPTOR SENSITIZING COMPOUNDS AND METHODS OF USE THEREFOR

(75) Inventors: Aaron D Schimmer, Ontario (CA); John C. Reed, Rancho Sante Fe, CA (US)

(73) Assignee: Burnham Institute for Medical Research, La Jolla, CA (US)

( * ) Notice: Subject to any disclaimer, the term of this patent is extended or adjusted under 35 U.S.C. 154(b) by 171 days.

(21) Appl. No.: 11/622,229

(22) Filed: Jan. 11, 2007

(65) Prior Publication Data

US 2008/0166378 A1    Jul. 10, 2008

Related U.S. Application Data

(60) Provisional application No. 60/758,166, filed on Jan. 11, 2006.

(51) Int. Cl.
*A01N 29/04*    (2006.01)

(52) U.S. Cl. ......................................... 514/757; 514/741

(58) Field of Classification Search ........................ None
See application file for complete search history.

(56) References Cited

OTHER PUBLICATIONS

Micheau et a.. (J. Natl. Cancer Inst. 1997; 89: 783-9).*
Freshney (Culture of Animal Cells, A Manual of Basic Technique, Alan R. Liss, Inc., 1983, New York, p. 4).*
Dermer (Bio/Technology, 1994, 12:320).*
Gura (Science, v278, 1997, pp. 1041-1042).*
Aoudjit, F., et al., "Matrix Attachment Regulates Fas-induced Apoptosis in Endothelial", *The Journal of Cell Biology*, 152(3), (2001), 633-643.
Boise, L. H, et al., "bcl-x, a bcl-2-Related Gene That Functions as a Dominant Regulator of Apoptotic Cell Death", *Cell*, 74(4), (1993), 597-608.
Bradford, M. M., "A Rapid and Sensitive Method for the Quantitation of Microgram Quantities of Protein Utilizing the Principle of Protein-Dye Binding", *Analytical Biochemistry*, 72, (1976), 248-254.
Carter, B. Z., et al., "Small-molecule XIAP inhibitors derepress downstream effector caspase and induce apoptosis of acute myeloid leukemia cells", *Blood*, 105(10), (2005), 4043-4050.
Frisch, S. M., "Evidence for a function of death-receptor-related, death-domain-containing proteins in anoikis", *Current Biology*, 9, (1999), 1047-1049.
Hajra, K. M., et al., "Apoptosome dysfunction in human cancer", *Apoptosis*, 9, (2004), 691-704.
Irmler, M., et al., "Inhibition of death receptor signal by cellular FLIP", *Nature*, 388, (Jul. 1997), 190-195.
Jiang, C., et al., "Caspases as Key Executors of Methyl Selenium-induced Apoptosis (Anoikis) of DU-145 Prostate Cancer Cells", *Cancer Research*, 61, (2001), 3062-3070.
Kharbanda, S., et al., "Role for Bcl-$x_L$ as an inhibitor of cytosolic cytochrome C accumulation in DNA damage-induced apoptosis", *Proc. Natl. Acad. Sci. USA*, 94, (1997), 6939-6942.
Kim, Y., et al., "An Inducible Pathway for Degradation of FLIP Protein Sensitizes Tumor Cells to TRAIL-induced Apoptosis", *The Journal of Biological Chemistry*, 277(25), (2002), 22320-22329.
Krueger, A., et al., "FLICE-Inhibitory Proteins: Regulators of Death Receptor-Mediated Apoptosis", *Molecular and Cellular Biology*, 21(24), (2001), 8247-8254.
Montel, A. H., et al., "Fas Involvement in Cytotoxicity Mediated by Human NK Cells", *Cellular Immunology*, 166, (1995), 236-246.
Montel, A. H., et al., "Fas-Mediated Cytotoxicity Remains Intact in Perforin and Granzyme B Antisense Transfectants of a Human NK-like Cell Line", *Cellular Immunology*, 165(2), (1995), 312-317.
Nagane, M., et al., "The potential of TRAIL for cancer chemotherapy", *Apoptosis*, 6(3), (2001), 191-197.
Pedersen, I. M., et al., "The triterpenoid CDDO induces apoptosis in refractory CLL B cells", *Blood* 100(8) , (2002), 2965-2972.
Perlman, H., et al., "FLICE-inhibitory Protein Expression Differentiation during Macrophage Differentiation Confers Resistance to Fas-mediatged Apoptosis", *The Journal of Experimental Medicine*, 190(11), (1999), 1679-1688.
Reed, J. C., "Drug Insight: cancer therapy strategies based on restoration of endogenous cell death mechanisms", *Nature Clinical Practice Oncology*, 3(7), (2006), 388.
Rosen, K., et al., "Cell Detachment Triggers p38 Mitogen-activated Protein Kinase-dependent Overexpression of Fas Ligand", *The Journal of Biological Chemistry*, 277(48), (2002), 46123-46130.
Rytömaa, M., et al., "Involvement of FADD and caspase-8 signalling in detachment-induced apoptosis", *Current Biology*, 9, (1999), 1043-1046.
Sayers, T. J., et al., "Molecular Mechanisms of Immune-Mediated Lysis of Murine Renal Cancer: Differential Contributions of Perforin-Dependent Versus Fas-Mediated Pathways in Lysis by NK and T Cells", *The Journal of Immunology*, 161(8), (1998), 3957-3965.
Scaffidi, C., et al., "The Role of c-FLIP in Modulation of CD95-induced Apoptosis", *The Journal of Biological Chemistry* 274(3), (1999), 1541-1548.
Scaffidi, C., et al., "Two CD95 (APO-1/Fas) signaling pathways", *The EMBO Journal*, 17(6), (1998), 1675-1687.
Schimmer, A. D., et al., "Identification of Small Molecules that sensitize Resistant Tumor Cells to Tumor Necrosis Factor-Family Death Receptors", *Cancer Research*, 66(4), (2006), 2367-2375.
Schimmer, A. D., et al., "Receptor- and mitochondrial-mediated apoptosis in acute leukemia: a translational view", *Blood*, 98(13), (2001), 3541-3553.
Schimmer, A. D., et al., "Small-molecule antagonists of apoptosis suppressor XIAP exhibit broad antitumor activity", *Cancer Cell*, 5, (2004), 25-35.
Takeda, K., et al., "Involvement of tumor necrosis factor-related apoptosis-inducing ligand in surveillance of tumor metastasis by liver natural killer cells", *Nature Medicine*, 7(1), (2001), 94-100.
Thome, M., et al., "Regulation of Lymphocyte Proliferation and Death by Flip", *Nature*, 1, (Oct. 2001), 50-58.
Wang, S., et al., "TRAIL and apoptosis induction by TNF-family death receptors", *Oncogene*, 22, (2003), 8628-8633.
Wood, T. E, et al., "A novel inhibitor of glucose uptake sensitizes cells to FAS-induced cell death", *Mol Cancer Ther.*, 7(11), (Nov. 2008), 3546-55.

(Continued)

*Primary Examiner* — Sheela J Huff

(74) *Attorney, Agent, or Firm* — Schwegman, Lundberg & Woessner, P.A.

(57) ABSTRACT

Methods of identifying death receptor sensitizing compounds and methods of using death receptor sensitizing compounds are provided.

20 Claims, 26 Drawing Sheets

OTHER PUBLICATIONS

Wuchter, C., et al., "In vitro susceptibility to TRAIL-induced apoptosis of acute leukemia cells in the context of TRAIL receptor gene expression and constitutive NF-kB activity", *Leukemia*, 15(6), (2001), 921-928.

Zhou, Q., et al., "Target Protease Specificity of the Viral Serpin CrmA", *The Journal of Biological Chemistry*, 272(12), (1997), 7797-7800.

Brothman, A. R., et al., "Abstract: Metastatic properties of the human prostatic cell line, PPC-1, in athymic nude mice", *J. Urol.*, 145(5):1008, (May 1991), 1 pg.

Fuchs-Young, R., et al., "Raloxifene is a tissue-selective agonist/antagonist that functions through the estrogen receptor", *Ann N Y Acad Sci.*, 761, (Jun. 12, 1995), 355-60.

Mediavilla, M. D., et al., "Abstract: Doses and time-dependent effects of 3'-azido-3'-deoxythymidine on T47D human breast cancer cells in vitro", *Pharmacol. Toxicol.*, 87(3):138-43, (Sep. 2000), 1 pg.

Place, Andrew E., et al., "The Novel Synthetic Triterpenoid, CDDO-Imidazolide, Inhibits Inflammatory Response and Tumor Growth in Vivo", *Clin. Cancer Res.*, 9:2798, vol. 9, (Jul. 2003), 2798-2806.

Zavaleta, C. L., et al., "Abstract: Use of avidin/biotin-liposome system for enhanced peritoneal drug delivery in an ovarian cancer model", *Int. J. Pharm.*, 337(1-2):316-28, Epub Jan. 14, 2007, (Jun. 2007), 1 pg.

\* cited by examiner

EC50

PPC1, CH-11
5.6 μM

PPC1
15 μM

EC50

PPC1, CH-11
25.7 μM

PPC1
45.4 μM

| ID | R | % Killing (5 μM + CH-11) | X |
|---|---|---|---|
| 5541203 | —CH₃ | 7.16 | Cl |
| 5569100 | —CH₂CH₃ | 44.2 | Cl |
| 5657593 | —CH₂–phenyl | 78.9 | Br |
| 5651311 | —CH₂–C₆H₄–CH₃ | 1.51 | Br |
| 5529457 | —CH₂CH₂–N(piperidine) | 77.2 | Cl |

DEATH RECEPTOR SENSITIZING COMPOUNDS AND METHODS OF USE THEREFOR

CROSS-REFERENCE TO RELATED APPLICATIONS

This application claims the benefit of the filing date of Ser. No. 60/758,166, filed Jan. 11, 2006, the disclosure of which is incorporated by reference herein.

STATEMENT OF GOVERNMENT RIGHTS

The invention was supported, at least in part, by a grant from the Government of the United States of America (grant no. CA78040 from the National Institutes of Health). The Government may have certain rights to the invention.

BACKGROUND

Interest in tumor vaccines is increasing with recent announcements of promising clinical trials. Vaccine strategies partially rely on cytolytic T lymphocytes (CTLs) and natural killer (NK) cells to eliminate malignant cells by inducing rapid apoptosis. In part, these immune cells use death receptor ligands such as tumor necrosis factor-α (TNFα), FAS-L, and TRAIL to stimulate certain TNF-family death receptors on tumor target cells, resulting in activation of caspase-family proteases and triggering of apoptosis (Takeda et al., 2001; Montel et al., 1995a; Montel et al., 1995b; Sayers et al., 1998). Attempts to exploit these immune effector molecules as anticancer agents have resulted in early stage clinical trials that employ a recombinant soluble fragment of TRAIL and agonistic monoclonal antibodies targeting TRAIL receptors (Nagane et al., 2001). A limitation of such therapies, however, is acquired or intrinsic resistance to TNF-family death ligands and death receptors, which commonly occurs in advanced malignancies (Wuchter et al., 2001).

Metastasis is the primary cause of cancer-related mortality in patients with most forms of solid tumors (Jemal et al., 2006). Early-stage tumors remain relatively localized, due in part to dependence on cell anchorage to the extra-cellular matrix (ECM) (Kimura et al., 2001; Zhou et al., 2001; Rennebeck et al., 2005). Continued tumor progression gives rise to cells that can grow independent of anchorage to the ECM and may eventually metastasize to other tissues (Zhou et al., 2001; DeMarzo et al., 2003).

Metastasis is a multi-step process. First, metastatic cells must detach from their primary tumor and survive in an anchorage-independent manner. After detachment, cells must migrate to the lymphatic and circulatory systems while evading immune surveillance. Once in the circulation, cells must invade distal organs, implant within local tissues, and initiate de novo tumor growth. Although all of these steps are required for metastasis, anchorage-independent survival represents a critical stage in the development of metastatic disease (Mehlen et al., 2006; Glinsky et al., 1997).

Normally, cells undergo apoptosis upon detachment from their ECM, a self-initiated process termed "anoikis" (Frisch et al., 1994; Frisch et al., 2001). Recent studies in non-malignant epithelial and endothelial cells suggest that anoikis is mediated, in part, by activation of the death receptor pathway of caspase activation (Frisch et al., 2001). In this pathway, ligands bind to the extra-cellular domains of the TNF family of death receptors. Ligand binding results in the recruitment of the intra-cellular protein FADD to the receptor's cytoplasmic domain (Jin et al., 2005). Receptor-bound FADD then recruits procaspase 8 to form a death-inducing signalling complex (DISC) (Muzio et al., 1996; Chinnaiyan et al., 1995; Kischkel et al., 1995). Dimerization and self-cleavage of procaspase 8 within the DISC generates active caspase 8, which returns to the cytosol to activate effector caspases (Medema et al., 1997; Boatright et al., 2003). In non-malignant cells, detachment from the ECM induces the expression of the death receptor protein Fas and its ligand FasL, with resultant activation of caspase 8 in a FADD-dependent manner (Aoudjit et al., 2001; Rosen et al., 2002; Rytomaa et al., 2999; Frisch, 1999; Bachelder et al., 2001).

This mechanism for achieving caspase activation is referred to as the "extrinsic" pathway, standing in contrast to another apoptosis pathway that involves mitochondria, and which has been termed the "intrinsic" pathway (Schimmer et al., 2001). Stimuli that activate the intrinsic pathway include DNA damaging anticancer drugs, γ-irradiation, hypoxia, and growth factor deprivation, causing mitochondria to release cytochrome c and other apoptogenic proteins into the cytosol, resulting in caspase activation (Hajra and Liu, 2004).

Diverse mechanisms can create roadblocks to apoptosis within the extrinsic or intrinsic pathways, occurring commonly in many cancers during tumor progression and thus creating impediments to successful treatment. Documented resistance mechanisms relevant to the extrinsic pathway include reduced expression of TNF-family death receptors, shedding of soluble death receptors and expression of ligand-binding decoy receptors, reduced expression of caspases-8 and -10, and overexpression of intracellular caspase inhibitors (Wand and El-Deiry, 2003). Among the endogenous caspase inhibitors affecting the extrinsic pathway is c-FLIP, a protein resembling caspases-8 and -10, which can bind and prevent their activation at the DISC (Irmler et al., 1997; Scaffidi et al., 1999).

Thus, there is a need for molecules that restore sensitivity of tumor cells to TNF-family death receptors and so are useful therapeutic adjuncts to agents such as recombinant TRAIL and tumor vaccines.

SUMMARY OF THE INVENTION

The invention provides a method to identify compounds that sensitize TNF-family death receptor ligand-resistant cells to one or more TNF-family death receptor ligands, as well as compounds that sensitize TNF-family death receptor ligand-resistant cells, e.g., compounds that sensitize FAS ligand- and TRAIL-resistant cancer cells to anti-FAS antibody- and TRAIL-mediated killing, compositions or kits which include one or more of those compounds, and methods of using those compounds. Thus, the invention provides compounds useful to induce apoptosis of cancer cells that are resistant to TNF-family death receptor ligand-mediated apoptosis. The compounds may alter extrinsic pathway apoptosis, or both extrinsic and intrinsic pathway apoptosis. In one embodiment, the compound alters extrinsic pathway apoptosis but does not alter FLIP expression in cells. In another embodiment, the compound alters extrinsic pathway apoptosis and alters FLIP expression.

In one embodiment, a compound of the invention has formula (I):

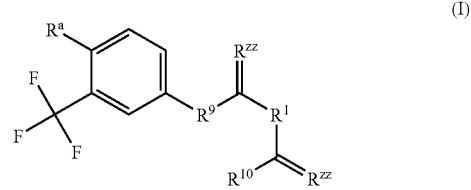

wherein, $R^1$ is alkylene, alkenylene, arylene, heteroarylene, heterocyclene or cycloalkylene;

$R^a$ is F, Cl, Br or I;

$R^9$ is O or $NR^x$;

each $R^{zz}$ is independently O, $NR^x$ or S;

$R^{10}$ is alkyl, alkenyl, alkoxy, halo, haloalkyl, hydroxy, hydroxyalkyl, heteroaryl, heterocycle, cycloalkyl, amino, alkylamino, $NR^xR^y$ or $COOR^x$; and each $R^x$ and $R^y$ is independently H, alkyl, alkenyl, aryl, heteroaryl, heterocycle, cycloalkyl or hydroxyl;

or a pharmaceutically acceptable salt thereof.

In another embodiment, a compound of the invention has formula (II):

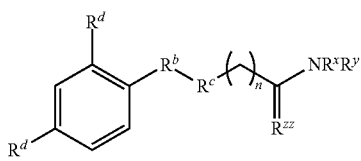

(II)

wherein, n is 0-5;

$R^b$ is O, S or $NR^z$, wherein $R^z$ is H or alkyl;

$R^c$ is alkylene, alkenylene, arylene, heteroarylene, heterocyclene or cycloalkylene;

each $R^d$ is independently halo, haloalkyl, hydroxyl, hydroxyalkyl, nitro, trifluoromethyl, trifluoromethoxy, cyano, or COOH;

$R^{zz}$ is O or NH;

$R^x$ and $R^y$ are each independently H, alkyl, alkenyl, aryl, heteroaryl, heterocycle, cycloalkyl or hydroxyl;

or a pharmaceutically acceptable salt thereof.

In yet another embodiment, a compound of the invention has formula (III):

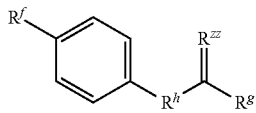

(III)

wherein, $R^f$ is halo, haloalkyl, hydroxyl, hydroxyalkyl, nitro, trifluoromethyl, trifluoromethoxy, cyano, or COOH;

$R^g$ is $CR^iR^j$ or $NR^iR^j$, wherein each $R^i$ and $R^j$ is independently alkyl, alkenyl, alkoxy, haloalkyl, hydroxy, hydroxyalkyl, aryl, heteroaryl, heterocycle, cycloalkyl, or $R^i$ and $R^j$ together form a heteroaryl or heterocycle optionally substituted with an arylalkenylene, arylalkylene, heteroarylalkylene, or heteroarylalkenylene;

$R^h$ is alkylene or alkenylene; and $R^{zz}$ is O, NH or S;

or a pharmaceutically acceptable salt thereof.

Also provided is a compound of formula (IV):

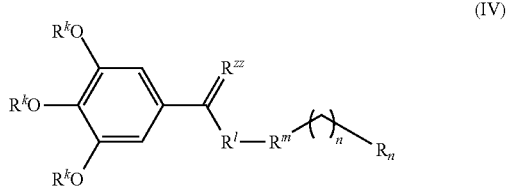

(IV)

wherein, n is 1-4;

each $R^k$ is independently H, alkyl or alkenyl;

$R^l$ is, alkylene, alkenylene or $NR^z$, wherein $R^z$ is H or alkyl;

$R^m$ is, alkylene, alkenylene or $NR^z$, wherein $R^z$ is H or alkyl;

$R^n$ is alkyl, alkenyl, alkoxy, haloalkyl, hydroxyalkyl, aryl, heteroaryl, heterocycle, or cycloalkyl; and $R^{zz}$ is O, NH or S;

or a pharmaceutically acceptable salt thereof;

a compound of formula (V):

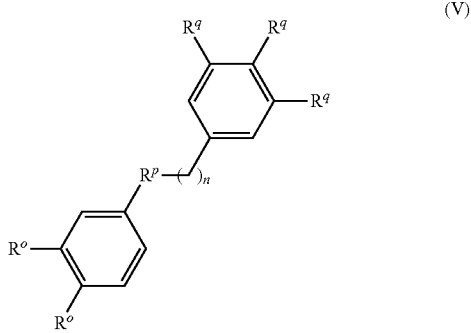

(V)

wherein, n is 1-4;

each $R^o$ is independently H, alkyl, alkoxy or alkenyl;

$R^p$ is O or $NR^z$, wherein $R^z$ is H or alkyl;

each $R^q$ is independently alkoxy or trifluoromethoxy;

or a pharmaceutically acceptable salt thereof;

a compound of formula (VI):

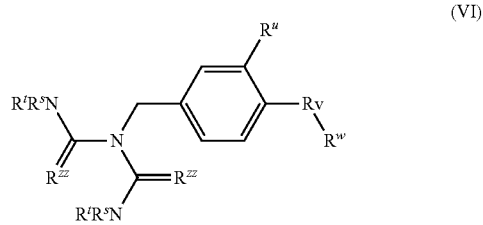

(VI)

wherein, each $R^s$ is independently H or alkyl;

each $R^t$ is independently H or alkyl;

$R^u$ is halo, haloalkyl, hydroxyl, hydroxyalkyl, nitro, trifluoromethyl, trifluoromethoxy, cyano, or COOH;

$R^v$ is O or $NR^z$;

$R^z$ is H or alkyl;

$R^w$ is alkyl, alkenyl, alkoxy, haloalkyl, hydroxyalkyl, aryl, heteroaryl, heterocycle, or cycloalkyl; and each $R^{zz}$ is independently O, NH or S;

or a pharmaceutically acceptable salt thereof;

a compound of formula (VII):

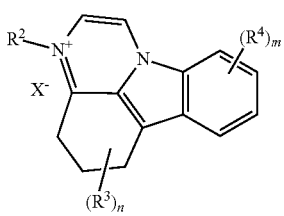

(VII)

wherein, $R^2$ is alkyl or alkenyl;

each $R^3$ is independently H, alkyl, alkylidenyl, alkenylidenyl, alkoxy, halo, haloalkyl, hydroxy, hydroxyalkyl, heteroaryl, heterocycle, cycloalkyl, alkanoyl, alkoxycarbonyl, amino, imino, alkylamino, acylamino, nitro, trifluoromethyl, trifluoromethoxy, carboxy, carboxyalkyl, keto, thioxo, alkylthio, alkylsulfinyl, alkylsulfonyl, cyano, imino, keto, thioxo, $NR^xR^y$ or $COOR^x$;

each $R^4$ is independently H, alkyl, alkoxy, halo, haloalkyl, hydroxy, hydroxyalkyl, heteroaryl, heterocycle, cycloalkyl, alkanoyl, alkoxycarbonyl, amino, alkylamino, acylamino, nitro, trifluoromethyl, trifluoromethoxy, carboxy, carboxyalkyl, keto, thioxo, alkylthio, alkylsulfinyl, alkylsulfonyl, cyano, $NR^xR^y$ or $COOR^x$;

each $R^x$ and $R^y$ are independently H, alkyl, aryl, heteroaryl, heterocycle, cycloalkyl or hydroxyl;

n is 0-3;

m is 0-5; and

X is a suitable counterion;

or a pharmaceutically acceptable salt thereof;

a compound of formula (VIII):

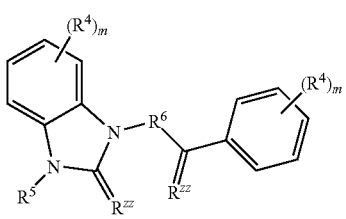

(VIII)

wherein, each $R^4$ is independently H, alkyl, alkoxy, halo, haloalkyl, hydroxy, hydroxyalkyl, heteroaryl, heterocycle, cycloalkyl, alkanoyl, alkoxycarbonyl, amino, alkylamino, acylamino, nitro, trifluoromethyl, trifluoromethoxy, carboxy, carboxyalkyl, alkylthio, alkylsulfinyl, alkylsulfonyl, cyano, $NR^xR^y$ and $COOR^x$;

each $R^x$ and $R^y$ are independently H, alkyl, aryl, heteroaryl, heterocycle, cycloalkyl or hydroxyl;

$R^5$ is H, alkyl, arylalkyl, or alkenyl;

$R^6$ is alkylene or alkenylene;

each $R^{zz}$ is independently O, $NR^x$ or S; and each m is independently 0-5;

or a pharmaceutically acceptable salt thereof; and

A compound of formula (IX):

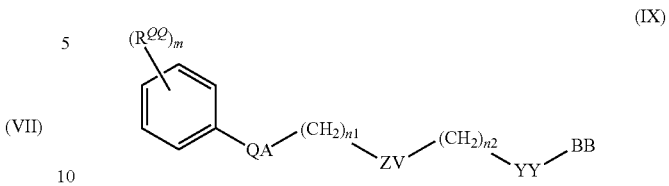

(IX)

wherein, each $R^{QQ}$ is independently H, alkyl, alkoxy, halo, haloalkyl, hydroxy, hydroxyalkyl, heteroaryl, heterocycle, cycloalkyl, alkanoyl, alkoxycarbonyl, amino, alkylamino, acylamino, nitro, trifluoromethyl, trifluoromethoxy, carboxy, carboxyalkyl, alkylthio, alkylsulfinyl, alkylsulfonyl, cyano, $NR^xR^y$ and $COOR^x$;

QA is alkylene, oxy (—O—), $NR^x$ or S;

ZV is C(=O)$NR^x$ or C(=S)$NR^x$;

YY is absent, oxy (—O—), or alkylene;

BB is alkyl or hydroxyl;

m is 0-5;

$n_1$ is 1-8;

$n_2$ is 0-8; and each $R^x$ is independently H or alkyl;

or a pharmaceutically acceptable salt thereof.

The compounds of the invention may be employed with any TNF-family death receptor ligand-resistant cancer, e.g., lung cancer, colorectal cancer, breast cancer, prostate cancer or other forms of cancer, and other diseases of proliferation.

As described hereinbelow, a 50,000 compound library was screened for agents that enhanced anti-FAS antibody-mediated killing of FAS ligand-resistant PPC-1 prostate cancer cells. PPC-1 cells are resistant to apoptosis induced by TRAIL and to agonistic antibodies targeting TNF-family death receptor FAS (CD95), despite expressing FAS and TRAIL receptors on their surface and expressing the requisite intracellular caspase activation machinery, including adaptor protein FADD and pro-caspases (Kim et al., 2002). After additional analyses, 8 compounds were identified that selectively sensitized PPC-1 cells to anti-FAS antibody, an extrinsic pathway agonist, without altering sensitivity to staurosporine and etoposide [VP16], which are intrinsic pathway agonists. These 8 compounds did not increase FAS surface levels, and besides sensitizing PPC-1 cells to apoptosis induced by an agonistic anti-FAS antibody, also sensitized PPC-1 cells to apoptosis induced by TNF-family member TRAIL, consistent with a post-receptor mechanism. Of the 8 compounds, 2 reduced expression of c-FLIP, an intracellular antagonist of the extrinsic pathway. Characterization of the effects of the 8 compounds on a panel of 10 solid tumor cell lines revealed 2 structurally distinct compounds that generally sensitized resistant cells to extrinsic pathway agonists. Structure-activity relation studies of one of these compounds revealed a pharmacophore useful to generate analogs with improved potency. Moreover, exposure of different tumor cell lines to compounds of the invention indicated that the compounds may be active in a variety of tumor cells and so useful with TNF-family death receptor- or ligand-based anti-cancer therapies. Altogether these findings demonstrate the feasibility of identifying compounds that selectively enhance apoptosis via the extrinsic pathway, thus providing tools for uncovering resistance mechanisms and therapeutics aimed at restoring sensitivity of tumor cells to immune effector mechanisms.

The present invention thus provides a method to identify one or more agents that enhance TNF-family death receptor ligand-mediated killing of tumor cells. The method includes contacting an amount of one or more agents, tumor cells that express TNF-family death receptors on the cell surface and are resistant to TNF-family death receptor ligand-mediated apoptosis, and an agonistic TNF-family death receptor ligand. Then it is determined whether one or more of the agents enhance TNF-family death receptor ligand-mediated killing of the tumor cells relative to tumor cells contacted with the agonistic TNF-family death receptor ligand but not the agent(s).

The invention also provides a method to enhance TNF-family death receptor ligand-mediated killing of tumor cells in a mammal in need of such therapy. The method includes administering an effective amount of a compound of formula (I)-(IX) and an effective amount of a TNF-family death receptor ligand to the mammal.

Further provided is a method to treat cells resistant to TNF-family death receptor ligand-mediated killing. The method includes contacting the cells with an effective amount of a compound of formula (I)-(IX).

The present invention also provides a method for treating TNF-family death receptor ligand-resistant cancer in a mammal, e.g., a human patient. The method includes contacting the cancer cells with a compound of formula (I)-(IX), or mixtures thereof, in an amount effective to provide for, or enhance the, susceptibility of the cancer cells to apoptosis mediated by one or more TNF-family death receptor ligands. The cancer cells may be contacted with a TNF-family death receptor ligand before, during or after contact with a compound of the invention, although some of the compounds of the invention may be useful to inhibit or treat cancer in the absence of a TNF-family death receptor ligand.

In addition, the present invention provides a method for inducing apoptosis or inducing cell death in cells in a mammal, e.g., a human patient, with TNF-family death receptor ligand-resistant cancer. The method includes contacting target cells ex vivo or in vivo with a compound of formula (I)-(IX), or mixtures thereof, in an amount effective to enhance apoptosis or cell death in the target cells which is mediated by one or more TNF-family death receptor ligands.

As also described herein, cells were grown on tissue culture treated polystyrene for adherent conditions or on hydrogel-coated ultra-low binding plates for suspension conditions. Cell viability, apoptosis and levels of FLIP were measured. Small molecules and siRNA were used to inhibit FLIP and assess the effects of FLIP inhibition on anoikis (loss of anchorage from the extra-cellular matrix) in vitro and in vivo. PPC-1 prostate cancer cells, which over express FLIP, that were cultured in anchorage-independent conditions resisted anoikis despite having increased levels of the death receptor Fas and its ligand FasL. Knockdown of FLIP expression by RNA interference or one of the identified compounds, sensitized prostate, breast, and ovarian cancer cell lines to anoikis in a manner that correlated with sensitization to Fas-signalling. Down-regulation of FLIP specifically initiated caspase 8 activation in suspension-cultured PPC-1 cells but not adherent-cultured PPC-1 cells, suggesting FLIP knockdown may derepress intrinsic mechanisms of Fas-signalling initiated upon loss of anchorage. FLIP knockdown also decreased the metastatic potential of circulating PPC-1 cells in vivo. Thus, FLIP may be a suppressor of anoikis and may be an important target for anti-metastatic therapeutic strategies.

Thus, also provided is a method of sensitizing cells to anoikis. The method includes administering to mammal in need thereof an effective amount of a compound of formula (I)-(IX) or siFLIP RNA.

Further provided is a method of inhibiting metastases. The method includes administering to mammal having cancer an effective amount of a compound of formula (I)-(IX) or siFLIP RNA.

The invention also provides a pharmaceutical composition comprising the compounds described herein, or a pharmaceutically acceptable salt thereof, in combination with a pharmaceutically acceptable diluent or carrier. Further, the invention provides a pharmaceutical composition comprising the compounds disclosed herein in combination with other known anticancer compounds, e.g., a TNF-family death receptor ligand.

Thus, the invention provides compounds for use in medical therapy, such as agents that induce TNF-family death receptor ligand-mediated apoptosis or agents that inhibit metastases, optionally in conjunction with other compounds that enhance TNF-family death receptor ligand-mediated apoptosis or cell death. Accordingly, the compounds of the invention are useful to inhibit or treat cancer, e.g., malignant gliomas, prostate cancer, ovarian cancer, colon cancer, breast cancer, leukemia, (such as, for example, lymphomas, neuroblastoma, breast cancer, lung cancer, prostate cancer, ovarian cancer, leukemias, and the like) or other proliferative diseases, including those that are resistant to TNF-family death receptor ligand-induced apoptosis. Also provided is the use of the compounds for the manufacture of a medicament to enhance apoptosis associated with TNF-family death receptor ligand binding to cells, or to inhibit metastases. The compounds may also be employed to enhance the efficacy of vaccines, e.g., tumor vaccines. Thus, further provided is the use of the compounds for the manufacture of a medicament to enhance the efficacy of a vaccine.

DETAILED DESCRIPTION OF THE INVENTION

Figure 1:
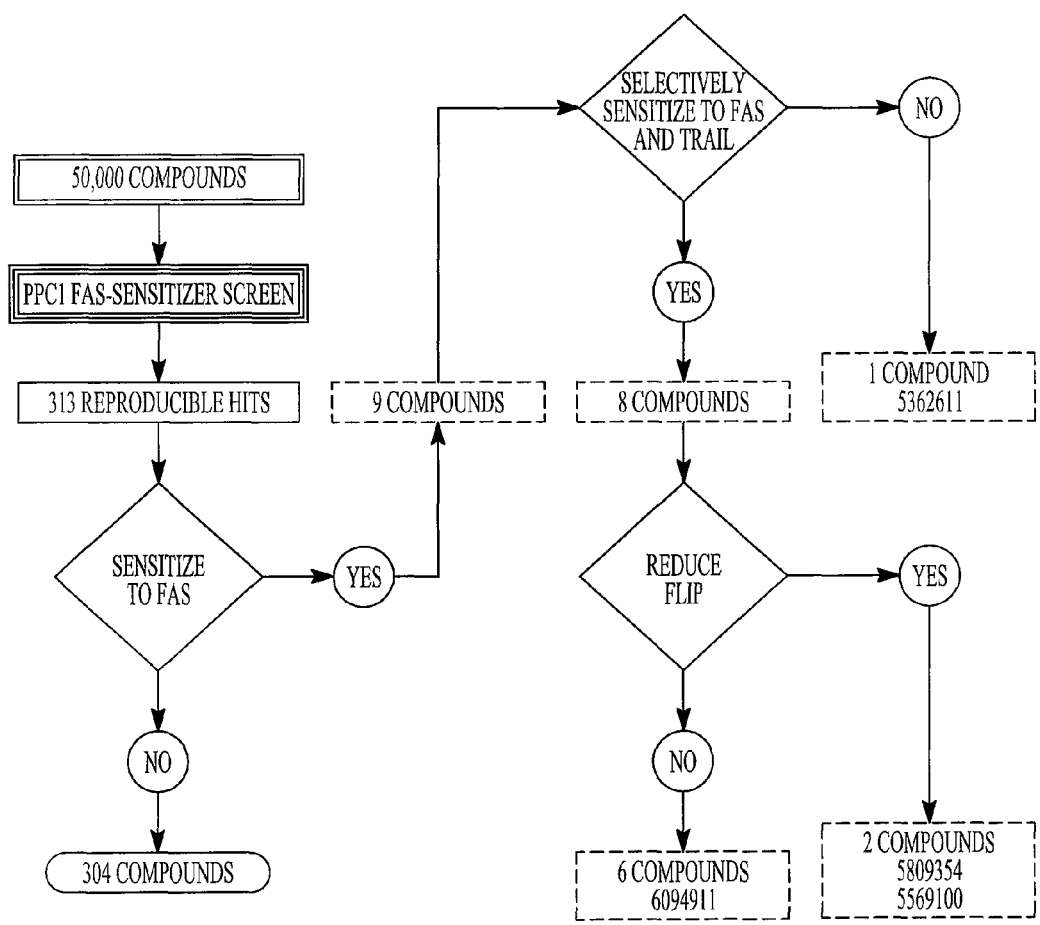
FIG. 1. A flowchart for identification of FAS-sensitizers using a cell-based high-throughput screening assay.
Figure 2A:
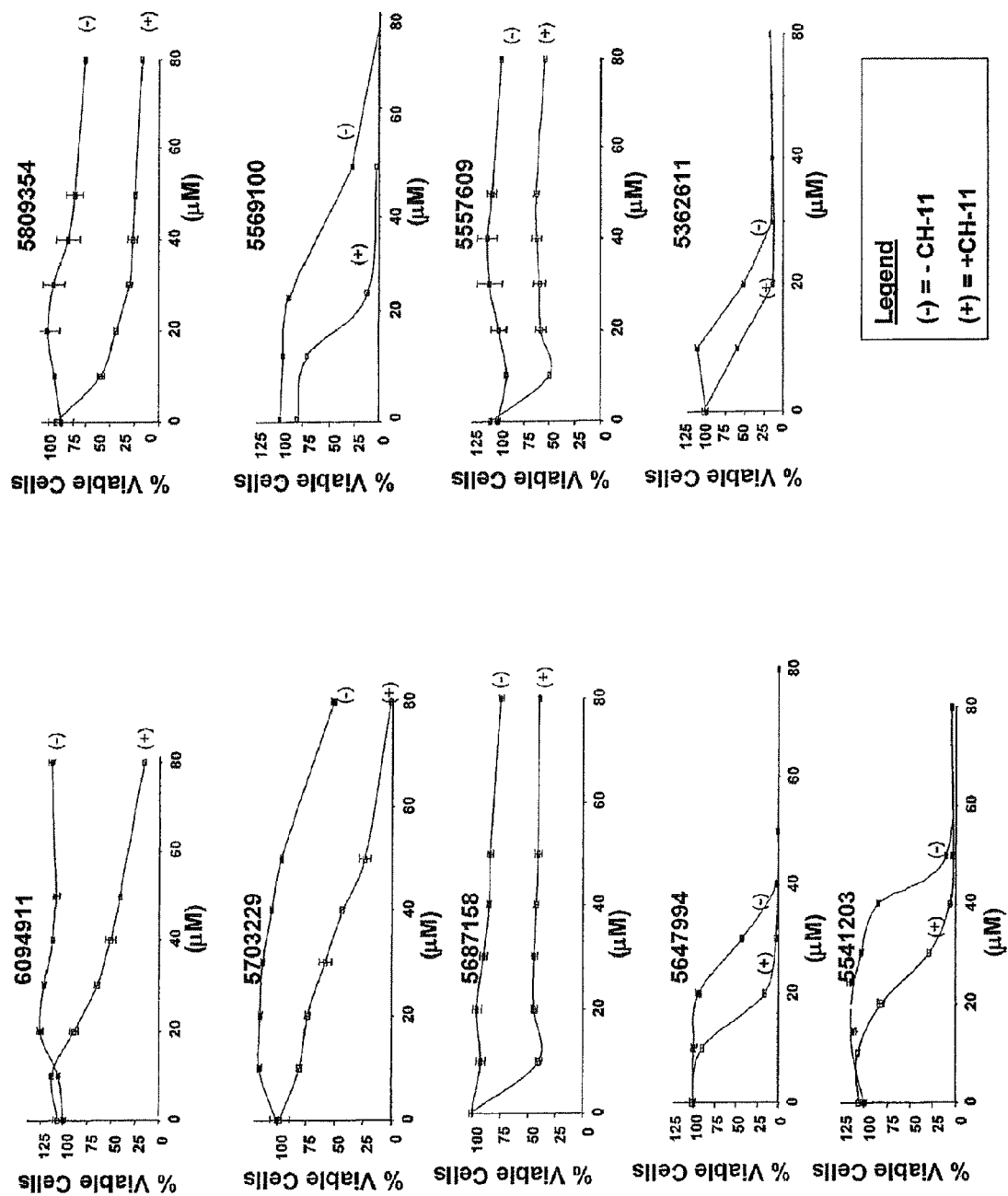
FIGS. 2A-C. Small molecules sensitize PPC-1 cells to CH-11 anti-FAS antibody. From the cell-based, high-throughput screen, 9 molecules were identified that sensitized PPC-1 cells to CH-11 antibody. PPC-1 cells ($1 \times 10^4$) were seeded in 96 well plates. The next day, cells were treated with increasing concentrations of the sensitizing compounds with (open squares) and without (closed squares) CH-11 antibody (100 ng/mL). Cell viability was measured 24 hours later by MTT assay. Cell viability is expressed as a mean percentage of untreated cells+SD (n=3). The Chembridge identification numbers of the compounds are provided. The same assay was employed to screen compounds related to compounds 5541203 and 5569100 (FIGS. 2B-C).
Figure 2B:
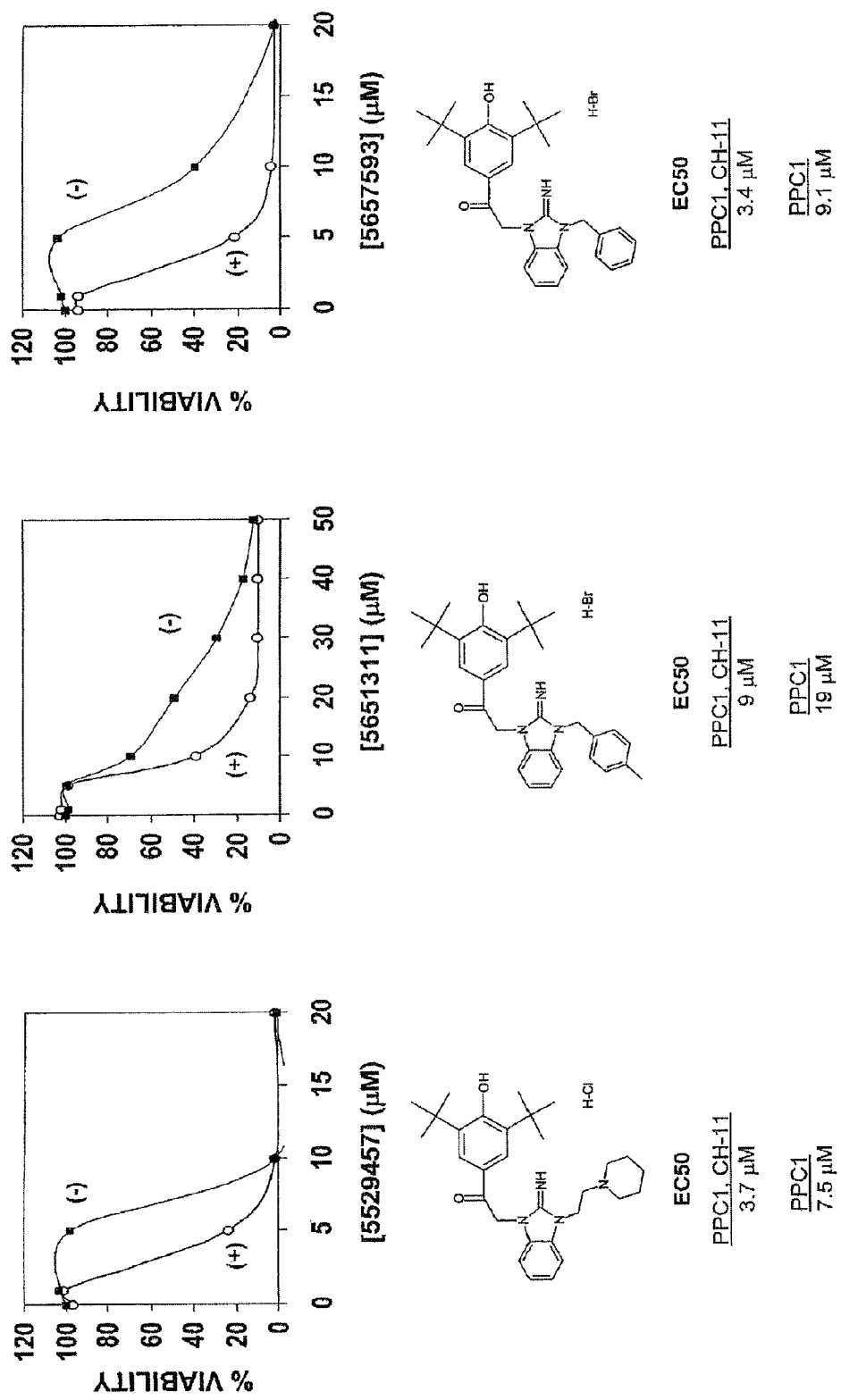
Figure 2C:
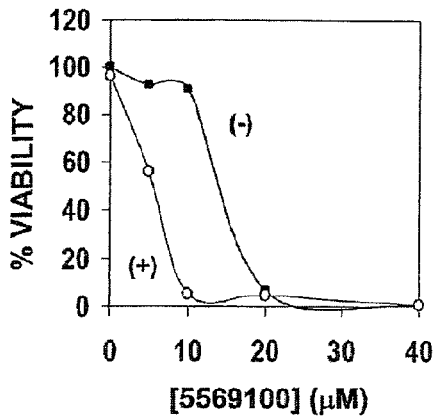
Figure 2C:
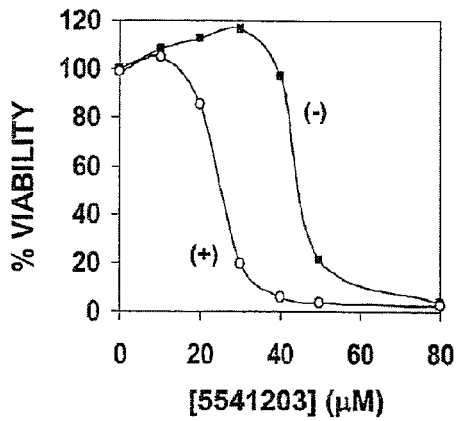
Figure 2C:
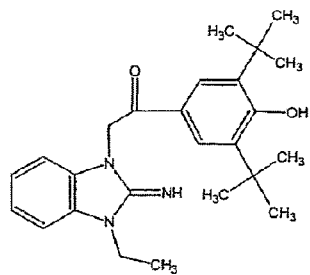
Figure 2C:
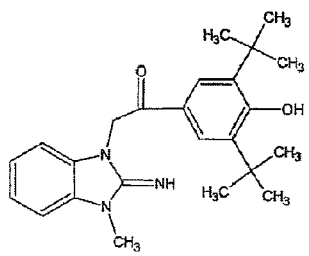

The present invention provides a method for screening compounds that either directly or indirectly kill cancer cells. In one embodiment, the screening method includes contacting cells, such as TNF-family death receptor ligand-resistant cells, with one or more test agents and a TNF-family death receptor ligand, to identify agents that sensitize cells to TNF-family death receptor ligand-mediated apoptosis. In another embodiment, cells are first contacted with one or more test agents and then with a TNF-family death receptor ligand, to identify agents that sensitize those cells to TNF-family death receptor ligand-mediated apoptosis. In one embodiment, cells are contacted with a TNF-family death receptor ligand and then with one or more test agents. In yet another embodiment, TNF-family death receptor ligand-resistant cells are contacted with one or more test agents, to identify agents that in a particular amount, kill those cells. The method thus identifies compounds that may be used alone or in conjunction with anticancer compounds, e.g., TNF-family death receptor ligands, to sensitize cancer cells, including cancer cells that are resistant, to TNF-family death receptor ligand-mediated cancer treatment. In one embodiment, compounds of the invention provide for apoptosis of cells that is not associated with intrinsic pathway apoptosis but is associated with extrinsic pathway apoptosis.

Definitions

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the compounds useful in the present invention can be synthesized from the parent compound, which contains a basic or acidic moiety, by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 17th ed., Mack Publishing Company, Easton, Pa., p. 1418 (1985), the disclosure of which is hereby incorporated by reference.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication commensurate with a reasonable benefit/risk ratio.

One diastereomer of a compound disclosed herein may display superior activity compared with the other. When required, separation of the racemic material can be achieved by HPLC using a chiral column or by a resolution using a resolving agent such as camphonic chloride as in Thomas J. Tucker, et al., J. Med. Chem. 1994 37, 2437-2444. A chiral compound of Formula I may also be directly synthesized using a chiral catalyst or a chiral ligand, e.g. Mark A. Huffman, et al., J. Org. Chem. 1995, 60, 1590-1594.

"Therapeutically effective amount" is intended to include an amount of a compound useful in the present invention or an amount of the combination of compounds claimed, e.g., to treat or prevent the disease or disorder, or to treat the symptoms of the disease or disorder, in a host. The combination of compounds is preferably a synergistic combination. Synergy, as described for example by Chou and Talalay, Adv. Enzyme Regul. 22:27-55 (1984), occurs when the effect of the compounds when administered in combination is greater than the additive effect of the compounds when administered alone as a single agent. In general, a synergistic effect is most clearly demonstrated at suboptimal concentrations of the compounds. Synergy can be in terms of lower cytotoxicity, increased activity, or some other beneficial effect of the combination compared with the individual components.

As used herein, "treating" or "treat" includes (i) preventing a pathologic condition from occurring (e.g. prophylaxis); (ii) inhibiting the pathologic condition or arresting its development; (iii) relieving the pathologic condition; and/or diminishing symptoms associated with the pathologic condition.

As used herein, the term "patient" refers to organisms to be treated by the methods of the present invention. Such organisms include, but are not limited to, mammals such as humans. In the context of the invention, the term "subject" generally refers to an individual who will receive or who has received treatment (e.g., administration of a compound of the invention, and optionally one or more anticancer agents) for cancer.

"Stable compound" and "stable structure" are meant to indicate a compound that is sufficiently robust to survive isolation to a useful degree of purity from a reaction mixture, and formulation into an efficacious therapeutic agent. Only stable compounds are contemplated by the present invention.

"Substituted" is intended to indicate that one or more hydrogens on the atom indicated in the expression using "substituted" is replaced with a selection from the indicated group(s), provided that the indicated atom's normal valency is not exceeded, and that the substitution results in a stable compound. Suitable indicated groups include, e.g., alkyl, alkenyl, alkylidenyl, alkenylidenyl, alkoxy, halo, haloalkyl, hydroxy, hydroxyalkyl, aryl, heteroaryl, heterocycle, cycloalkyl, alkanoyl, alkoxycarbonyl, amino, imino, alkylamino, acylamino, nitro, trifluoromethyl, trifluoromethoxy, carboxy, carboxyalkyl, keto, thioxo, alkylthio, alkylsulfinyl, alkylsulfonyl, cyano, $NR^xR^y$ and/or $COOR^x$, wherein each $R^x$ and $R^y$ are independently H, alkyl, alkenyl, aryl, heteroaryl, heterocycle, cycloalkyl or hydroxy. When a substituent is keto (i.e., =O) or thioxo (i.e., =S) group, then 2 hydrogens on the atom are replaced.

"Interrupted" is intended to indicate that in between two or more adjacent carbon atoms, and the hydrogen atoms to which they are attached (e.g., methyl ($CH_3$), methylene ($CH_2$) or methine (CH)), indicated in the expression using "interrupted" is inserted with a selection from the indicated group(s), provided that the each of the indicated atoms' normal valency is not exceeded, and that the interruption results in a stable compound. Such suitable indicated groups include, e.g., non-peroxide oxy (—O—), thio (—S—), carbonyl (—C(=O)—), carboxy (—C(=O)O—), imine (C=NH), sulfonyl (SO) or sulfoxide ($SO_2$).

Specific and preferred values listed below for radicals, substituents, and ranges, are for illustration only; they do not exclude other defined values or other values within defined ranges for the radicals and substituents.

"Alkyl" refers to a $C_1$-$C_{18}$ hydrocarbon containing normal, secondary, tertiary or cyclic carbon atoms. Examples are methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —CH($CH_3$)$_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —CH($CH_3$)$CH_2CH_3$), 2-methyl-2-propyl (t-Bu, t-butyl, —C($CH_3$)$_3$), 1-pentyl (n-pentyl, —$CH_2CH_2CH_2CH_2CH_3$), 2-pentyl (—CH($CH_3$)$CH_2CH_2CH_3$), 3-pentyl (—CH($CH_2CH_3$)$_2$), 2-methyl-2-butyl (—C($CH_3$)$_2CH_2CH_3$), 3-methyl-2-butyl (—Ch($CH_3$)CH($CH_3$)$_2$), 3-methyl-1-butyl (—$CH_2CH_2CH(CH_3)_2$), 2-methyl-1-butyl (—$Ch_2CH(CH_3)CH_2CH_3$), 1-hexyl (—$Ch_2CH_2CH_2CH_2CH_2CH_3$), 2-hexyl (—Ch($CH_3$)$CH_2CH_2CH_2CH_3$), 3-hexyl (—Ch($CH_2CH_3$)($CH_2CH_2CH_3$)), 2-methyl-2-pentyl (—C($CH_3$)$_2CH_2CH_2CH_3$), 3-methyl-2-pentyl (—Ch($CH_3$)CH($CH_3$)$CH_2CH_3$), 4-methyl-2-pentyl (—Ch($CH_3$)$CH_2CH(CH_3)_2$), 3-methyl-3-pentyl (—C($CH_3$)($CH_2CH_3$)$_2$), 2-methyl-3-pentyl (—CH($CH_2CH_3$)CH($CH_3$)$_2$), 2,3-dimethyl-2-butyl (—C($CH_3$)$_2$CH($CH_3$)$_2$), 3,3-dimethyl-2-butyl (—CH($CH_3$)C($CH_3$)$_3$).

The alkyl can optionally be substituted with one or more alkenyl, alkylidenyl, alkenylidenyl, alkoxy, halo, haloalkyl, hydroxy, hydroxyalkyl, aryl, heteroaryl, heterocycle, cycloalkyl, alkanoyl, alkoxycarbonyl, amino, imino, alkylamino, acylamino, nitro, trifluoromethyl, trifluoromethoxy, carboxy, carboxyalkyl, keto, thioxo, alkylthio, alkylsulfinyl, alkylsulfonyl, cyano, $NR^xR^y$ and/or $COOR^x$, wherein each $R^x$ and $R^y$ are independently H, alkyl, alkenyl, aryl, heteroaryl, heterocycle, cycloalkyl or hydroxyl. The alkyl can optionally be interrupted with one or more non-peroxide oxy (—O—), thio (—S—), carbonyl (—C(=O)—), carboxy (—C(=O)O—), sulfonyl (SO) or sulfoxide ($SO_2$). Additionally, the alkyl can optionally be at least partially unsaturated, thereby providing an alkenyl.

"Alkenyl" refers to a $C_2$-$C_{18}$ hydrocarbon containing normal, secondary, tertiary or cyclic carbon atoms with at least one site of unsaturation, i.e. a carbon-carbon, $sp^2$ double bond. Examples include, but are not limited to: ethylene or vinyl (—CH=$CH_2$), allyl (—$CH_2$CH=$CH_2$), cyclopentenyl (—$C_5H_7$), and 5-hexenyl (—$CH_2$ $CH_2CH_2CH_2$CH=$CH_2$).

The alkenyl can optionally be substituted with one or more alkyl, alkylidenyl, alkenylidenyl, alkoxy, halo, haloalkyl, hydroxy, hydroxyalkyl, aryl, heteroaryl, heterocycle, cycloalkyl, alkanoyl, alkoxycarbonyl, amino, imino, alkylamino, acylamino, nitro, trifluoromethyl, trifluoromethoxy, carboxy, carboxyalkyl, keto, thioxo, alkylthio, alkylsulfinyl, alkylsulfonyl, cyano, $NR^xR^y$ and/or $COOR^x$, wherein each $R^x$ and $R^y$ are independently H, alkyl, alkenyl, aryl, heteroaryl, heterocycle, cycloalkyl or hydroxyl. Additionally, the alkenyl can optionally be interrupted with one or more non-peroxide oxy (—O—), thio (—S—), carbonyl (—C(=O)—), carboxy (—C(=O)O—), sulfonyl (SO) or sulfoxide ($SO_2$).

"Alkylidenyl" refers to a $C_1$-$C_{18}$ hydrocarbon containing normal, secondary, tertiary or cyclic carbon atoms. Examples are methylidenyl (=$CH_2$), ethylidenyl (=CH$CH_3$), 1-propylidenyl (=CH$CH_2CH_3$), 2-propylidenyl (=C($CH_3$)$_2$), 1-butylidenyl (=CH$CH_2CH_2CH_3$), 2-methyl-1-propylidenyl (=CHCH($CH_3$)$_2$), 2-butylidenyl (=C($CH_3$)$CH_2CH_3$), 1-pentyl (=CH$CH_2CH_2CH_2CH_3$), 2-pentylidenyl (=C($CH_3$)$CH_2CH_2CH_3$), 3-pentylidenyl (=C($CH_2CH_3$)$_2$), 3-methyl-2-butylidenyl (=C($CH_3$)CH($CH_3$)$_2$), 3-methyl-1-butylidenyl (=CH$CH_2$CH($CH_3$)$_2$), 2-methyl-1-butylidenyl (=CHCH($CH_3$)$CH_2CH_3$), 1-hexylidenyl (=CH$CH_2CH_2CH_2CH_2CH_3$), 2-hexylidenyl (=C($CH_3$)$CH_2CH_2CH_2CH_3$), 3-hexylidenyl (=C($CH_2CH_3$)($CH_2CH_2CH_3$)), 3-methyl-2-pentylidenyl (=C($CH_3$)CH($CH_3$)$CH_2CH_3$), 4-methyl-2-pentylidenyl (=C($CH_3$)$CH_2$CH($CH_3$)$_2$), 2-methyl-3-pentylidenyl (=C($CH_2CH_3$)CH($CH_3$)$_2$), and 3,3-dimethyl-2-butylidenyl (=C($CH_3$)C($CH_3$)$_3$).

The alkylidenyl can optionally be substituted with one or more alkyl, alkenyl, alkenylidenyl, alkoxy, halo, haloalkyl, hydroxy, hydroxyalkyl, aryl, heteroaryl, heterocycle, cycloalkyl, alkanoyl, alkoxycarbonyl, amino, imino, alkylamino, acylamino, nitro, trifluoromethyl, trifluoromethoxy, carboxy, carboxyalkyl, keto, thioxo, alkylthio, alkylsulfinyl, alkylsulfonyl, cyano, $NR^xR^y$ and/or $COOR^x$, wherein each $R^x$ and $R^y$ are independently H, alkyl, alkenyl, aryl, heteroaryl, heterocycle, cycloalkyl or hydroxyl. Additionally, the alkylidenyl can optionally be interrupted with one or more non-peroxide oxy (—O—), thio (—S—), carbonyl (—C(=O)—), carboxy (—C(=O)O—), sulfonyl (SO) or sulfoxide ($SO_2$).

"Alkenylidenyl" refers to a $C_2$-$C_{18}$ hydrocarbon containing normal, secondary, tertiary or cyclic carbon atoms with at least one site of unsaturation, i.e. a carbon-carbon, $sp^2$ double bond. Examples include, but are not limited to: allylidenyl (=CHCH=$CH_2$), and 5-hexenylidenyl (=CH$CH_2CH_2CH_2$CH=$CH_2$).

The alkenylidenyl can optionally be substituted with one or more alkyl, alkenyl, alkylidenyl, alkoxy, halo, haloalkyl, hydroxy, hydroxyalkyl, aryl, heteroaryl, heterocycle, cycloalkyl, alkanoyl, alkoxycarbonyl, amino, imino, alkylamino, acylamino, nitro, trifluoromethyl, trifluoromethoxy, carboxy, carboxyalkyl, keto, thioxo, alkylthio, alkylsulfinyl, alkylsulfonyl, cyano, $NR^xR^y$ and/or $COOR^x$, wherein each $R^x$ and $R^y$ are independently H, alkyl, alkenyl, aryl, heteroaryl, heterocycle, cycloalkyl or hydroxyl. Additionally, the alkenylidenyl can optionally be interrupted with one or more non-peroxide oxy (—O—), thio (—S—), carbonyl (—C(=O)—), carboxy (—C(=O)O—), sulfonyl (SO) or sulfoxide ($SO_2$).

"Alkylene" refers to a saturated, branched or straight chain or cyclic hydrocarbon radical of 1-18 carbon atoms, and having two monovalent radical centers derived by the removal of two hydrogen atoms from the same or different carbon atoms of a parent alkane. Typical alkylene radicals include, but are not limited to: methylene (—$CH_2$—) 1,2-ethyl (—$CH_2CH_2$—), 1,3-propyl (—$CH_2CH_2CH_2$—), 1,4-butyl (—$CH_2CH_2CH_2CH_2$—), and the like.

The alkylene can optionally be substituted with one or more alkyl, alkenyl, alkylidenyl, alkenylidenyl, alkoxy, halo, haloalkyl, hydroxy, hydroxyalkyl, aryl, heteroaryl, heterocycle, cycloalkyl, alkanoyl, alkoxycarbonyl, amino, imino, alkylamino, acylamino, nitro, trifluoromethyl, trifluoromethoxy, carboxy, carboxyalkyl, keto, thioxo, alkylthio, alkylsulfinyl, alkylsulfonyl, cyano, $NR^xR^y$ and/or $COOR^x$, wherein each $R^x$ and $R^y$ are independently H, alkyl, alkenyl, aryl, heteroaryl, heterocycle, cycloalkyl or hydroxyl. Additionally, the alkylene can optionally be interrupted with one or more non-peroxide oxy (—O—), thio (—S—), carbonyl (—C(=O)—), carboxy (—C(=O)O—), sulfonyl (SO) or sulfoxide ($SO_2$). Moreover, the alkylene can optionally be at least partially unsaturated, thereby providing an alkenylene.

"Alkenylene" refers to an unsaturated, branched or straight chain or cyclic hydrocarbon radical of 2-18 carbon atoms, and having two monovalent radical centers derived by the removal of two hydrogen atoms from the same or two different carbon atoms of a parent alkene. Typical alkenylene radicals include, but are not limited to: 1,2-ethylene (—CH=CH—).

The alkenylene can optionally be substituted with one or more alkyl, alkenyl, alkylidenyl, alkenylidenyl, alkoxy, halo, haloalkyl, hydroxy, hydroxyalkyl, aryl, heteroaryl, heterocycle, cycloalkyl, alkanoyl, alkoxycarbonyl, amino, imino, alkylamino, acylamino, nitro, trifluoromethyl, trifluoromethoxy, carboxy, carboxyalkyl, keto, thioxo, alkylthio, alkylsulfinyl, alkylsulfonyl, cyano, $NR^xR^y$ and/or $COOR^x$, wherein each $R^x$ and $R^y$ are independently H, alkyl, alkenyl, aryl, heteroaryl, heterocycle, cycloalkyl or hydroxyl. Additionally, The alkenylene can optionally be interrupted with one or more non-peroxide oxy (—O—), thio (—S—), carbonyl (—C(=O)—), carboxy (—C(=O)O—), sulfonyl (SO) or sulfoxide ($SO_2$).

The term "alkoxy" refers to the groups alkyl-O—, where alkyl is defined herein. Preferred alkoxy groups include, e.g., methoxy, ethoxy, n-propoxy, iso-propoxy, n-butoxy, tert-butoxy, sec-butoxy, n-pentoxy, n-hexoxy, 1,2-dimethylbutoxy, and the like.

The alkoxy can optionally be substituted with one or more alkyl, alkylidenyl, alkenylidenyl, halo, haloalkyl, hydroxy, hydroxyalkyl, aryl, heteroaryl, heterocycle, cycloalkyl, alkanoyl, alkoxycarbonyl, amino, imino, alkylamino, acylamino, nitro, trifluoromethyl, trifluoromethoxy, carboxy, carboxyalkyl, keto, thioxo, alkylthio, alkylsulfinyl, alkylsulfonyl, cyano, $NR^xR^y$ and $COOR^x$, wherein each $R^x$ and $R^y$ are independently H, alkyl, aryl, heteroaryl, heterocycle, cycloalkyl or hydroxyl.

The term "aryl" refers to an unsaturated aromatic carbocyclic group of from 6 to 20 carbon atoms having a single ring (e.g., phenyl) or multiple condensed (fused) rings, wherein at least one ring is aromatic (e.g., naphthyl, dihydrophenanthrenyl, fluorenyl, or anthryl). Preferred aryls include phenyl, naphthyl and the like.

The aryl can optionally be substituted with one or more alkyl, alkenyl, alkoxy, halo, haloalkyl, hydroxy, hydroxyalkyl, heteroaryl, heterocycle, cycloalkyl, alkanoyl, alkoxycarbonyl, amino, imino, alkylamino, acylamino, nitro, trifluoromethyl, trifluoromethoxy, carboxy, carboxyalkyl, keto, thioxo, alkylthio, alkylsulfinyl, alkylsulfonyl, cyano, $NR^xR^y$ and $COOR^x$, wherein each $R^x$ and $R^y$ are independently H, alkyl, aryl, heteroaryl, heterocycle, cycloalkyl or hydroxyl.

The term "cycloalkyl" refers to cyclic alkyl groups of from 3 to 20 carbon atoms having a single cyclic ring or multiple condensed rings. Such cycloalkyl groups include, by way of example, single ring structures such as cyclopropyl, cyclobutyl, cyclopentyl, cyclooctyl, and the like, or multiple ring structures such as adamantanyl, and the like.

The cycloalkyl can optionally be substituted with one or more alkyl, alkenyl, alkoxy, halo, haloalkyl, hydroxy, hydroxyalkyl, aryl, heteroaryl, heterocycle, alkanoyl, alkoxycarbonyl, amino, imino, alkylamino, acylamino, nitro, trifluoromethyl, trifluoromethoxy, carboxy, carboxyalkyl, keto, thioxo, alkylthio, alkylsulfinyl, alkylsulfonyl, cyano, $NR^xR^y$ and $COOR^x$, wherein each $R^x$ and $R^y$ are independently H, alkyl, aryl, heteroaryl, heterocycle, cycloalkyl or hydroxyl.

The cycloalkyl can optionally be at least partially unsaturated, thereby providing a cycloalkenyl.

The term "halo" refers to fluoro, chloro, bromo, and iodo. Similarly, the term "halogen" refers to fluorine, chlorine, bromine, and iodine.

"Haloalkyl" refers to alkyl as defined herein substituted by 1-4 halo groups as defined herein, which may be the same or different. Representative haloalkyl groups include, by way of example, trifluoromethyl, 3-fluorododecyl, 12,12,12-trifluorododecyl, 2-bromooctyl, 3-bromo-6-chloroheptyl, and the like.

The term "heteroaryl" is defined herein as a monocyclic, bicyclic, or tricyclic ring system containing one, two, or three aromatic rings and containing at least one nitrogen, oxygen, or sulfur atom in an aromatic ring, and which can be unsubstituted or substituted, for example, with one or more, and in particular one to three, substituents, like halo, alkyl, hydroxy, hydroxyalkyl, alkoxy, alkoxyalkyl, haloalkyl, nitro, amino, alkylamino, acylamino, alkylthio, alkylsulfinyl, and alkylsulfonyl. Examples of heteroaryl groups include, but are not limited to, 2H-pyrrolyl, 3H-indolyl, 4H-quinolizinyl, 4nH-carbazolyl, acridinyl, benzo[b]thienyl, benzothiazolyl, β-carbolinyl, carbazolyl, chromenyl, cinnaolinyl, dibenzo[b,d] furanyl, furazanyl, furyl, imidazolyl, imidizolyl, indazolyl, indolisinyl, indolyl, isobenzofuranyl, isoindolyl, isoquinolyl, isothiazolyl, isoxazolyl, naphthyridinyl, naptho[2,3-b], oxazolyl, perimidinyl, phenanthridinyl, phenanthrolinyl, phenarsazinyl, phenazinyl, phenothiazinyl, phenoxathiinyl, phenoxazinyl, phthalazinyl, pteridinyl, purinyl, pyranyl, pyrazinyl, pyrazolyl, pyridazinyl, pyridyl, pyrimidinyl, pyrimidinyl, pyrrolyl, quinazolinyl, quinolyl, quinoxalinyl, thiadiazolyl, thianthrenyl, thiazolyl, thienyl, triazolyl, and xanthenyl. In one embodiment the term "heteroaryl" denotes a monocyclic aromatic ring containing five or six ring atoms containing carbon and 1, 2, 3, or 4 heteroatoms independently selected from the group non-peroxide oxygen, sulfur, and N(Z) wherein Z is absent or is H, O, alkyl, phenyl or benzyl. In another embodiment heteroaryl denotes an ortho-fused bicyclic heterocycle of about eight to ten ring atoms derived therefrom, particularly a benz-derivative or one derived by fusing a propylene, or tetramethylene diradical thereto.

The heteroaryl can optionally be substituted with one or more alkyl, alkenyl, alkoxy, halo, haloalkyl, hydroxy, hydroxyalkyl, aryl, heterocycle, cycloalkyl, alkanoyl, alkoxycarbonyl, amino, imino, alkylamino, acylamino, nitro, trifluoromethyl, trifluoromethoxy, carboxy, carboxyalkyl, keto, thioxo, alkylthio, alkylsulfinyl, alkylsulfonyl, cyano, $NR^xR^y$ and $COOR^x$, wherein each $R^x$ and $R^y$ are independently H, alkyl, aryl, heteroaryl, heterocycle, cycloalkyl or hydroxyl.

The term "heterocycle" refers to a saturated or partially unsaturated ring system, containing at least one heteroatom selected from the group oxygen, nitrogen, and sulfur, and optionally substituted with alkyl or $C(=O)OR^b$, wherein $R^b$ is hydrogen or alkyl. Typically heterocycle is a monocyclic, bicyclic, or tricyclic group containing one or more heteroatoms selected from the group oxygen, nitrogen, and sulfur. A heterocycle group also can contain an oxo group (=O) attached to the ring. Non-limiting examples of heterocycle groups include 1,3-dihydrobenzofuran, 1,3-dioxolane, 1,4-dioxane, 1,4-dithiane, 2H-pyran, 2-pyrazoline, 4H-pyran, chromanyl, imidazolidinyl, imidazolinyl, indolinyl, isochromanyl, isoindolinyl, morpholine, piperazinyl, piperidine, piperidyl, pyrazolidine, pyrazolidinyl, pyrazolinyl, pyrrolidine, pyrroline, quinuclidine, and thiomorpholine.

The heterocycle can optionally be substituted with one or more alkyl, alkenyl, alkoxy, halo, haloalkyl, hydroxy, hydroxyalkyl, aryl, heteroaryl, cycloalkyl, alkanoyl, alkoxycarbonyl, amino, imino, alkylamino, acylamino, nitro, trifluoromethyl, trifluoromethoxy, carboxy, carboxyalkyl, keto, thioxo, alkylthio, alkylsulfinyl, alkylsulfonyl, cyano, $NR^xR^y$ and $COOR^x$, wherein each $R^x$ and $R^y$ are independently H, alkyl, aryl, heteroaryl, heterocycle, cycloalkyl or hydroxyl.

Examples of nitrogen heterocycles and heteroaryls include, but are not limited to, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, morpholino, piperidinyl, tetrahydrofuranyl, and the like as well as N-alkoxy-nitrogen containing heterocycles. In one specific embodiment of the invention, the nitrogen heterocycle can be 3-methyl-5,6-dihydro-4H-pyrazino[3,2,1-jk]carbazol-3-ium iodide.

Another class of heterocyclics is known as "crown compounds" which refers to a specific class of heterocyclic compounds having one or more repeating units of the formula [—$(CH_2$-$)_a$A-] where a is equal to or greater than 2, and A at each separate occurrence can be O, N, S or P. Examples of crown compounds include, by way of example only, [—$(CH_2)_3$—NH—]$_3$, [—$((CH_2)_2$—O)$_4$—$((CH_2)_2$—NH)$_2$] and the like. Typically such crown compounds can have from 4 to 10 heteroatoms and 8 to 40 carbon atoms.

The term "alkanoyl" refers to C(=O)R, wherein R is an alkyl group as previously defined.

The term "acyloxy" refers to —O—C(=O)R, wherein R is an alkyl group as previously defined. Examples of acyloxy groups include, but are not limited to, acetoxy, propanoyloxy, butanoyloxy, and pentanoyloxy. Any alkyl group as defined above can be used to form an acyloxy group.

The term "alkoxycarbonyl" refers to C(=O)OR, wherein R is an alkyl group as previously defined.

The term "amino" refers to —$NH_2$, and the term "alkylamino" refers to —$NR_2$, wherein at least one R is alkyl and the second R is alkyl or hydrogen. The term "acylamino" refers to RC(=O)N, wherein R is alkyl or aryl.

The term "imino" refers to —C=NH.
The term "nitro" refers to —$NO_2$.
The term "trifluoromethyl" refers to —$CF_3$.
The term "trifluoromethoxy" refers to —$OCF_3$.
The term "cyano" refers to —CN.
The term "hydroxy" or "hydroxyl" refers to —OH.
The term "oxy" refers to —O—.
The term "thio" refers to —S—.
The term "thioxo" refers to (=S).
The term "keto" refers to (=O).

As to any of the above groups, which contain one or more substituents, it is understood, of course, that such groups do not contain any substitution or substitution patterns which are sterically impractical and/or synthetically non-feasible. In addition, the compounds of this invention include all stereochemical isomers arising from the substitution of these compounds.

Selected substituents within the compounds described herein are present to a recursive degree. In this context, "recursive substituent" means that a substituent may recite another instance of itself. Because of the recursive nature of such substituents, theoretically, a large number may be present in any given claim. One of ordinary skill in the art of medicinal chemistry understands that the total number of such substituents is reasonably limited by the desired properties of the compound intended. Such properties include, by way of example and not limitation, physical properties such as molecular weight, solubility or log P, application properties such as activity against the intended target, and practical properties such as ease of synthesis.

Recursive substituents are an intended aspect of the invention. One of ordinary skill in the art of medicinal and organic chemistry understands the versatility of such substituents. To the degree that recursive substituents are present in a claim of the invention, the total number will be determined as set forth above.

The compounds described herein can be administered as the parent compound, a pro-drug of the parent compound, or an active metabolite of the parent compound.

"Pro-drugs" are intended to include any covalently bonded substances which release the active parent drug or other formulas or compounds of the present invention in vivo when such pro-drug is administered to a mammalian subject. Pro-drugs of a compound of the present invention are prepared by modifying functional groups present in the compound in such a way that the modifications are cleaved, either in routine manipulation in vivo, to the parent compound. Pro-drugs include compounds of the present invention wherein the carbonyl, carboxylic acid, hydroxy or amino group is bonded to any group that, when the pro-drug is administered to a mammalian subject, cleaves to form a free carbonyl, carboxylic acid, hydroxy or amino group. Examples of pro-drugs include, but are not limited to, acetate, formate and benzoate derivatives of alcohol and amine functional groups in the compounds of the present invention, and the like.

"Metabolite" refers to any substance resulting from biochemical processes by which living cells interact with the active parent drug or other formulas or compounds of the present invention in vivo, when such active parent drug or other formulas or compounds of the present are administered to a mammalian subject. Metabolites include products or intermediates from any metabolic pathway.

"Metabolic pathway" refers to a sequence of enzyme-mediated reactions that transform one compound to another and provide intermediates and energy for cellular functions. The metabolic pathway can be linear or cyclic.

Obviously, numerous modifications and variations of the present invention are possible in light of the above teachings. It is therefore to be understood that within the scope of the appended claims, the invention may be practiced otherwise than as specifically described herein.

A specific group of compounds of the invention have the formula (I):

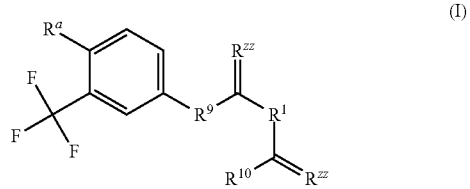

wherein, $R^1$ is alkylene, alkenylene, arylene, heteroarylene, heterocyclene or cycloalkylene;

$R^a$ is F, Cl, Br or I;

$R^9$ is O or $NR^x$;

each $R^{zz}$ is independently O, $NR^x$ or S;

$R^{10}$ is alkyl, alkenyl, alkoxy, halo, haloalkyl, hydroxy, hydroxyalkyl, heteroaryl, heterocycle, cycloalkyl, amino, alkylamino, $NR^xR^y$ or $COOR^x$; and each $R^x$ and $R^y$ is independently H, alkyl, alkenyl, aryl, heteroaryl, heterocycle, cycloalkyl or hydroxyl;

or a pharmaceutically acceptable salt thereof.

A specific group of compounds of the invention have the formula (II):

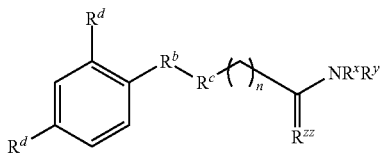

(II)

wherein, n is 0-5;

$R^b$ is O, S or $NR^z$, wherein $R^z$ is H or alkyl;

$R^c$ is alkylene, alkenylene, arylene, heteroarylene, heterocyclene or cycloalkylene;

each $R^d$ is independently halo, haloalkyl, hydroxyl, hydroxyalkyl, nitro, trifluoromethyl, trifluoromethoxy, cyano, or COOH;

$R^{zz}$ is O or NH;

$R^x$ and $R^y$ are each independently H, alkyl, alkenyl, aryl, heteroaryl, heterocycle, cycloalkyl or hydroxyl;

or a pharmaceutically acceptable salt thereof.

A specific group of compounds of the invention have the formula (III):

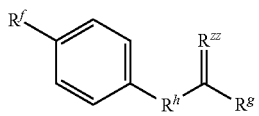

(III)

wherein, $R^f$ is halo, haloalkyl, hydroxyl, hydroxyalkyl, nitro, trifluoromethyl, trifluoromethoxy, cyano, or COOH;

$R^g$ is $CR^iR^j$ or $NR^iR^j$, wherein each $R^i$ and $R^j$ is independently alkyl, alkenyl, alkoxy, haloalkyl, hydroxy, hydroxyalkyl, aryl, heteroaryl, heterocycle, cycloalkyl, or $R^i$ and $R^j$ together form a heteroaryl or heterocycle optionally substituted with an arylalkenylene, arylalkylene, heteroarylalkylene, or heteroarylalkenylene;

$R^h$ is alkylene or alkenylene; and $R^{zz}$ is O, NH or S;

or a pharmaceutically acceptable salt thereof.

A specific group of compounds of the invention have the formula (IV):

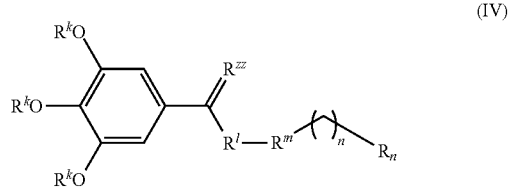

(IV)

wherein, n is 1-4;

each $R^k$ is independently H, alkyl or alkenyl;

$R^l$ is O, alkylene, alkenylene or $NR^z$, wherein $R^z$ is H or alkyl;

$R^m$ is O, alkylene, alkenylene or $NR^z$, wherein $R^z$ is H or alkyl;

$R^n$ is alkyl, alkenyl, alkoxy, haloalkyl, hydroxyalkyl, aryl, heteroaryl, heterocycle, or cycloalkyl; and $R^{zz}$ is O, NH or S;

or a pharmaceutically acceptable salt thereof.

A specific group of compounds of the invention have the formula (V):

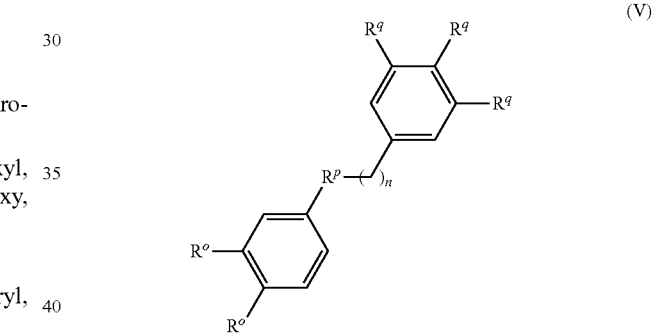

(V)

wherein, n is 1-4;

each $R^o$ is independently H, alkyl, alkoxy or alkenyl;

$R^p$ is O or $NR^z$, wherein $R^z$ is H or alkyl;

each $R^q$ is independently alkoxy or trifluoromethoxy;

or a pharmaceutically acceptable salt thereof.

A specific group of compounds of the invention have the formula (VI):

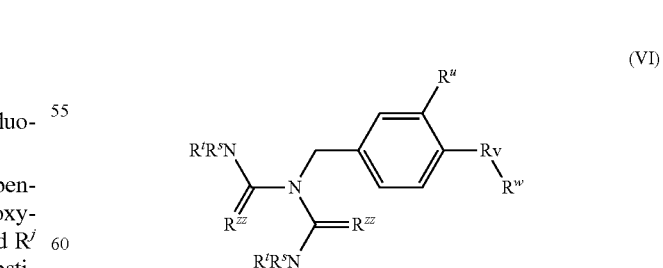

(VI)

wherein, each $R^s$ is independently H or alkyl;

each $R^t$ is independently H or alkyl;

$R^u$ is halo, haloalkyl, hydroxyl, hydroxyalkyl, nitro, trifluoromethyl, trifluoromethoxy, cyano, or COOH;

$R^v$ is O or $NR^z$;
$R^z$ is H or alkyl;
$R^w$ is alkyl, alkenyl, alkoxy, haloalkyl, hydroxyalkyl, aryl, heteroaryl, heterocycle, or cycloalkyl; and
each $R^{zz}$ is independently O, NH or S;
or a pharmaceutically acceptable salt thereof.

A specific group of compounds of the invention have the formula (VII):

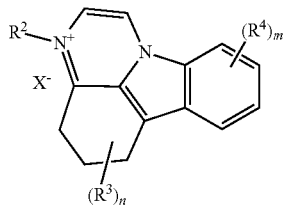

(VII)

wherein,
$R^2$ is alkyl or alkenyl;
each $R^3$ is independently H, alkyl, alkylidenyl, alkenylidenyl, alkoxy, halo, haloalkyl, hydroxy, hydroxyalkyl, heteroaryl, heterocycle, cycloalkyl, alkanoyl, alkoxycarbonyl, amino, imino, alkylamino, acylamino, nitro, trifluoromethyl, trifluoromethoxy, carboxy, carboxyalkyl, keto, thioxo, alkylthio, alkylsulfinyl, alkylsulfonyl, cyano, imino, keto, thioxo, $NR^xR^y$ or $COOR^x$;
each $R^4$ is independently H, alkyl, alkoxy, halo, haloalkyl, hydroxy, hydroxyalkyl, heteroaryl, heterocycle, cycloalkyl, alkanoyl, alkoxycarbonyl, amino, alkylamino, acylamino, nitro, trifluoromethyl, trifluoromethoxy, carboxy, carboxyalkyl, keto, thioxo, alkylthio, alkylsulfinyl, alkylsulfonyl, cyano, $NR^xR^y$ or $COOR^x$;
each $R^x$ and $R^y$ are independently H, alkyl, aryl, heteroaryl, heterocycle, cycloalkyl or hydroxyl;
n is 0-3;
m is 0-5; and
X is a suitable counterion;
or a pharmaceutically acceptable salt thereof.

A specific group of compounds of the invention have the formula (VIII):

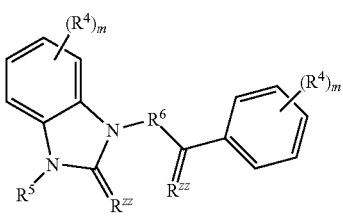

(VIII)

wherein,
each $R^4$ is independently H, alkyl, alkoxy, halo, haloalkyl, hydroxy, hydroxyalkyl, heteroaryl, heterocycle, cycloalkyl, alkanoyl, alkoxycarbonyl, amino, alkylamino, acylamino, nitro, trifluoromethyl, trifluoromethoxy, carboxy, carboxyalkyl, alkylthio, alkylsulfinyl, alkylsulfonyl, cyano, $NR^xR^y$ and $COOR^x$;
each $R^x$ and $R^y$ are independently H, alkyl, aryl, heteroaryl, heterocycle, cycloalkyl or hydroxyl;
$R^5$ is H, alkyl, arylalkyl, or alkenyl;
$R^6$ is alkylene or alkenylene;
each $R^{zz}$ is independently O, $NR^x$ or S; and
each m is independently 0-5;
or a pharmaceutically acceptable salt thereof A specific group of compounds of the invention have the formula (IX):

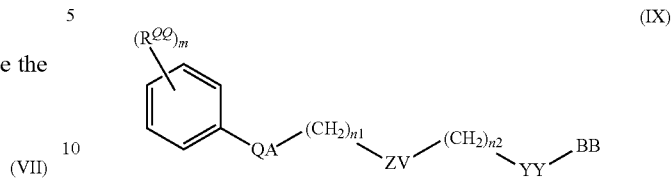

(IX)

wherein,
each $R^{QQ}$ is independently H, alkyl, alkoxy, halo, haloalkyl, hydroxy, hydroxyalkyl, heteroaryl, heterocycle, cycloalkyl, alkanoyl, alkoxycarbonyl, amino, alkylamino, acylamino, nitro, trifluoromethyl, trifluoromethoxy, carboxy, carboxyalkyl, alkylthio, alkylsulfinyl, alkylsulfonyl, cyano, $NR^xR^y$ and $COOR^x$;
QA is alkylene, oxy (—O—), $NR^x$ or S;
ZV is $C(=O)NR^x$ or $C(=S)NR^x$;
YY is absent, oxy (—O—), or alkylene;
BB is alkyl or hydroxyl;
m is 0-5;
$n_1$ is 1-8;
$n_2$ is 0-8; and
each $R^x$ is independently H or alkyl;
or a pharmaceutically acceptable salt thereof.

Specific Ranges, Values and Embodiments

Specific ranges, values, and embodiments provided below are for illustration purposes only and do not otherwise limit the scope of the invention, as defined by the claims.

For the compound of formula (I):
A specific value for $R^1$ is alkylene.
Another specific value for $R^1$ is methylene.
A specific value for $R^a$ is Cl.
A specific value for $R^9$ is $NR^x$.
Another specific value for $R^9$ is NH.
Another specific value for each $R^{zz}$ is O.
A specific value for $R^x$ is H.
A specific value for $R^{10}$ is alkyl.
Another specific value for $R^{10}$ is methyl.

For the compound of formula (II):
A specific value for n is 0.
A specific value for $R^b$ is O.
A specific value for $R^c$ is alkylene.
Another specific value for $R^c$ is n-propylene.
A specific value for each $R^d$ is halo.
Another specific value for each $R^d$ is chloro.
A specific value for $R^{zz}$ is O.
A specific value for $R^x$ is H.
A specific value for $R^y$ is hydroxyl.
or a pharmaceutically acceptable salt thereof.

For the compound of formula (III):
A specific value for $R^f$ is halo.
Another specific value for $R^f$ is chloro.
A specific value for $R^g$ is $NR^iR^j$, wherein $R^i$ and $R^j$ together form a heterocycle, substituted with an arylalkenylene, arylalkylene, heteroarylalkylene, or heteroarylalkenylene.
Another specific value for $R^g$ is $NR^iR^j$, wherein $R^i$ and $R^j$ together form a heterocycle, substituted with an arylalkenylene.
A specific value for $R^h$ is alkylene.
Another specific value for $R^h$ is methylene.
A specific value for $R^{zz}$ O.

For the compound of formula (IV):
  A specific value for n is 1.
  A specific value for each $R^k$ is alkyl.
  Another specific value for each $R^k$ is methyl.
  A specific value for $R^l$ is $NR^z$, wherein $R^z$ is H.
  A specific value for $R^m$ is $NR^z$, wherein $R^z$ is H.
  A specific value for $R^n$ is heterocycle.
  A specific value for $R^{zz}$ is O.
For the compound of formula (V):
  A specific value for n is 1.
  A specific value for each $R^o$ is alkyl.
  Another specific value for each $R^o$ is methyl.
  A specific value for $R^p$ is $NR^z$, wherein $R^z$ is H.
  A specific value for each $R^q$ is alkoxy.
For the compound of formula (VI):
  A specific value for each $R^s$ is H.
  A specific value for each $R^t$ is H.
  A specific value for $R^u$ is halo.
  Another specific value for $R^u$ is chloro.
  A specific value for $R^v$ is O.
  A specific value for $R^w$ is alkyl.
  Another specific value for $R^w$ is sec-butyl.
  A specific value for each $R^{zz}$ is NH.
For the compound of formula (VII):
  A specific value for $R^2$ is alkyl.
  Another specific value for $R^2$ is methyl.
  A specific value for each $R^3$ is H.
  A specific value for each $R^4$ is cycloalkyl.
  A specific value for each $R^4$ is cyclohexyl.
  A specific value for n is 1.
  A specific value for m is 1.
  A specific value for X is iodo.
For the compound of formula (VIII):
  A specific value for each $R^4$ is independently H, alkyl or hydroxyl.
  Another specific value for each $R^4$ is independently H, tert-butyl or hydroxyl.
  A specific value for $R^5$ is alkyl.
  Another specific value for $R^5$ is alkyl, which is optionally substituted with aryl, which is optionally substituted with alkyl.
  Another specific value for $R^5$ is alkyl, which is optionally substituted with aryl.
  Another specific value for $R^5$ is alkyl, which is optionally substituted with cycloalkyl.
  Another specific value for $R^5$ is methyl.
  Another specific value for $R^5$ is ethyl.
  Another specific value for $R^5$ is 1-ethylpiperidinyl.
  Another specific value for $R^5$ is 4-methyl benzyl.
  Another specific value for $R^5$ is benzyl.
  A specific value for $R^6$ is alkylene.
  Another specific value for $R^6$ is methylene.
  A specific value for each $R^{zz}$ is independently O or $NR^x$.
  A specific value for each $R^{zz}$ is independently O or $NR^x$, wherein $R^x$ is H.
  A specific value for each m is 1.
  Another specific value for m is 2.
  Another specific value for m is 3.
For the compound of formula (IX):
  A specific value for $R^{QQ}$ is halo and/or alkyl.
  Another specific value for $R^{QQ}$ is halo.
  Another specific value for $R^{QQ}$ is alkyl.
  Another specific value for $R^{QQ}$ is chloro and/or methyl.
  Another specific value for $R^{QQ}$ is ortho-methyl and para-chloro.
  A specific value for QA is oxy (—O—).
  A specific value for ZV is $C(=O)NR^x$.
  Another specific value for ZV is C(=O)NH.
  A specific value for YY is absent.
  Another specific value for YY is alkylene.
  Another specific value for YY is oxy (—O—).
  A specific value for BB is alkyl.
  A specific value for BB is hydroxyl.
  A specific value for m is 2.
  A specific value for $n_1$ is 3.
  A specific value for $n_2$ is 0-3.
  Another specific value for $n_2$ is 0.
  Another specific value for $n_2$ is 3.

Specific compounds useful in the present invention include, e.g.,

N-[4-chloro-3-(trifluoromethyl)phenyl]-3-oxobutanamide;
4-(2,4-dichlorophenoxy)-N-hydroxybutanamide;
1-[(4-chlorophenyl)acetyl]-4-[(2e)3-phenylprop-2-enyl]piperazine;
3,4,5-trimethoxy-N'-((5-methyltetrahydrofuran-2-yl)methyl)benzohydrazide;
3,4-dimethyl-N-(3,4,5-trimethoxybenzyl)aniline;
N-(3-chloro-4-(isopentyloxy)benzyl)-Imidodicarbonimidamide;
8-Cyclohexyl-3-methyl-5,6-dihydro-4H-pyrazino[3,2,1-jk]carbazol-3-ium; iodide;
1-(3,5-Di-tert-butyl-4-hydroxy-phenyl)-2-(2-imino-3-methyl-2,3-dihydro-benzoimidazol-1-yl)-ethanone;
1-(3,5-Di-tert-butyl-4-hydroxy-phenyl)-2-(3-ethyl-2-imino-2,3-dihydro-benzoimidazol-1-yl)-ethanone;
1-(3,5-di-tert-butyl-4-hydroxyphenyl)-2-(2-imino-3-(2-(piperidin-1-yl)ethyl)-2,3-dihydro-1H-benzo[d]imidazol-1-yl)ethanone hydrochloride;
1-(3,5-di-tert-butyl-4-hydroxyphenyl)-2-(2-imino-3-(4-methylbenzyl)-2,3-dihydro-1H-benzo[d]imidazol-1-yl)ethanone hydrobromide;
2-(3-benzyl-2-imino-2,3-dihydro-1H-benzo[d]imidazol-1-yl)-1-(3,5-di-tert-butyl-4-hydroxyphenyl)ethanone hydrobromide;
1-(3,5-di-tert-butyl-4-hydroxyphenyl)-2-(3-ethyl-2-imino-2,3-dihydro-1H-benzo[d]imidazol-1-yl)ethanone hydrobromide;
1-(3,5-di-tert-butyl-4-hydroxyphenyl)-2-(2-imino-3-methyl-2,3-dihydro-1H-benzo[d]imidazol-1-yl)ethanone hydrobromide;
((4-(4-chloro-2-methylphenoxy))-N-hydroxybutanamide); and
((4-(4-chloro-2-methylphenoxy))-N-(3-ethoxypropyl)-butanamide).

The compounds of the invention can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

The present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Useful dosages of the compounds of the invention can be determined by comparing their in vitro activity and in vivo activity in animal models. Methods for the extrapolation of effective dosages in mice, and other animals, to humans are known to the art; for example, see U.S. Pat. No. 4,938,949.

Generally, the concentration of the compounds of the invention in a liquid composition, such as a lotion, will be from about 0.1-25 wt-%, preferably from about 0.5-10 wt-%. The concentration in a semi-solid or solid composition such as a gel or a powder will be about 0.1-5 wt-%, preferably about 0.5-2.5 wt-%.

The amount of the compound, or an active salt or derivative thereof, required for use alone or with other anticancer compounds will vary not only with the particular salt selected but also with the route of administration, the nature of the condition being treated and the age and condition of the patient and will be ultimately at the discretion of the attendant physician or clinician.

In general, however, a suitable dose may be in the range of from about 0.5 to about 100 mg/kg, e.g., from about 10 to about 75 mg/kg of body weight per day, such as 3 to about 50 mg per kilogram body weight of the recipient per day, preferably in the range of 6 to 90 mg/kg/day, most preferably in the range of 15 to 60 mg/kg/day.

The compound may be conveniently administered in unit dosage form; for example, containing 5 to 1000 mg, conveniently 10 to 750 mg, most conveniently, 50 to 500 mg of active ingredient per unit dosage form.

The active ingredient may be administered to achieve peak plasma concentrations of the active compound of from about 0.5 to about 75 μM, preferably, about 1 to 50 μM, most preferably, about 2 to about 30 μM. This may be achieved, for example, by the intravenous injection of a 0.05 to 5% solution of the active ingredient, optionally in saline, or orally administered as a bolus containing about 1-100 mg of the active ingredient. Desirable blood levels may be maintained by continuous infusion to provide about 0.01-5.0 mg/kg/hr or by intermittent infusions containing about 0.4-15 mg/kg of the active ingredient(s).

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

The following invention will be further described by the following nonlimiting examples.

EXAMPLE 1

Experimental Methods

Reagents. A 50,000 compound Diversa chemical library was obtained from Chembridge (San Diego, Calif.). The anti-FAS monoclonal antibody CH-11 was purchased from MBL (MBL, Co. Ltd., Nagoya, Japan). TRAIL was obtained from Alexis (San Diego, Calif.). VP-16 and staurosporine were purchased from Sigma (Sigma Inc., Milwaukee, Wis.). 2-cyano-3,12-dioxooleana-1,9-dien-28-oic acid (CDDO) was a generous gift from Michael Sporn (Dartmouth University).

Cell Lines. Cell lines were maintained in RPMI 1640 supplemented with 2.5-10% fetal calf serum (FCS) (Hyclone, Tulare, Calif.), 1 mM L-glutamine and antibiotics (streptomycin/penicillin). Cells were cultured at 37° C. in a humid atmosphere with 5% $CO_2$.

High throughput screening. Screens were performed using a fully integrated, programmable robotic liquid handling system (Biomek® FX, Beckman-Coulter Inc., Fullerton, Calif.), with integrated plate reader (LJL analyst HT 96-384, Sunnyvale, Calif.) and environmentally controlled plate carousel set at 37° C. and 5% $CO_2$:95% air. PPC-1 cells ($1 \times 10^4$) were seeded overnight into 96 well, flat-bottom plates (Costar, Cambridge, Mass.) in 100 µL of medium containing 2.5% FCS. The next day, aliquots from the 50,000 compound Diversa library were added at a final concentration of 7.5 µg/mL (about 25 µM) in a final concentration of 0.5% (v:v) dimethylsulfoxide (DMSO). CH-11 antibody (100 ng/mL) was then added, and the cells were incubated for 24 hours before assessing cell viability by a 3-(4,5-Dimethylthiazol-2-yl)-2,5-diphenyltetrazolium Bromide (MTT) dye reduction assay (Sigma).

Cell death assays. Cell viability was measured by MTT and MTS assays, essentially as described in Schimmer et al. (2004). Absorbance readings were plotted against a standard curve to derive the corresponding cell number, and cell viability was expressed as a percentage relative to untreated cells. Apoptosis was measured by flow cytometric analysis of Annexin V surface expression after staining cells with FITC-anti-Annexin V and propidium iodide (PI) (Biovision, Mountain View, Calif.), as described in Pederson et al. (2002).

Cell transfections. PPC-1 cells ($2 \times 10^5$) were seeded in 35 mm diameter plates in RPMI with 10% FCS. The next day the cells were co-transfected using Lipofectamine Plus (Invitrogen, Carlsbad, Calif.) with 0.5 µg GFP-encoding plasmid pEGFP (Invitrogen) in combination with 1.5 µg of plasmids encoding Bcl-XL, the viral caspase-8 inhibitor Crm A, or empty vector. At 2 days post-transfection, cells were incubated with various concentrations of CH-11 antibody and the test compounds for 24 hours, then the percentage apoptosis was scored by UV-microscopic analysis of the GFP-positive cells, counting a minimum of 200 cells. Cells that had rounded up and were floating in the medium were counted as non-viable, while cells that remained adherent to the plate with normal morphological features were counted as viable.

Immunoblot analysis. Protein extracts were obtained by washing cells with phosphate-buffered saline (PBS) [pH 7.4] and suspending the cells in lysis buffer [10 mM Tris (pH 7.4), 150 mM NaCl, 0.1% Triton X-100, 0.5% sodium deoxycholate, and 5 mM EDTA] containing protease inhibitors (Complete tablets; Roche, Indianapolis, Ind.). Immunoblot assays were performed as described in Carter et al. (2005). Briefly, equal amounts of protein as determined by a Bradford assay (Bradford, 1976) were subjected to SDS-PAGE (4-20% gradient gels from ISC BioExpress, Kaysville, Utah), followed by transfer to nitrocellulose membranes. Membranes were incubated with mouse monoclonal anti-human FLIP (NF6 clone) (1:500 v/v) (Alexis, San Diego, Calif.), 1:1,000 (v/v) anti-caspase-8 clone 5F7 (Upstate) and mouse monoclonal anti-tubulin (1:2000 v/v) (Sigma Inc). Secondary antibodies consisted of horseradish peroxidase-conjugated goat anti-rabbit IgG or goat anti-mouse IgG (Bio-Rad, Hercules, Calif.). Detection was performed by the enhanced chemiluminescence method (Pierce, Rockford, Ill.).

Transfection of siRNA oligonucleotides. Double-stranded SMARTPOOL siRNA oligonucleotides targeting c-FLIP mRNA and double-stranded firefly luciferase control siRNA (Dharmacon Research, Lafayette, Colo.) (10 nM) were transfected into cells with Lipofectamine according to the manufacturer's instructions.

Quantitative RT-PCR. The cDNAs encoding the long isoform of FLIPL and GAPDH were amplified using the following primer pairs: 5'-CCTAGGAATCTGCCTGATAATCGA-3' (forward primer for FLIP; SEQ ID NO:1), 5'-TGGGATATACCATGCATACTGAGATG-3' (reverse primer for FLIP; SEQ ID NO:2), 5'-GAAGGTGAAGGTCG-GAGTC-3' (forward primer for GAPDH; SEQ ID NO:3), and 5'-GAAGATGGTGATGGGATTTC-3' (reverse primer for GAPDH; SEQ ID NO:4). Equal amounts of cDNA for each sample were added to a prepared master mix (SYBR Green PCR Master mix, Applied Biosystems, Foster City, Calif.). Real-time quantitative PCR reactions were performed on an ABI Prism 7700 sequence detection system (Applied Biosystems, Foster City, Calif., USA). The relative abundance of a transcript was represented by the threshold cycle of amplification ($C_T$), which is inversely correlated to the amount of target RNA/first strand cDNA being amplified. To normalize for equal amounts of the latter, the transcript levels of the putative housekeeping gene GAPDH were assayed. The comparative $C_T$ method was calculated as per manufacturer's instructions. To normalize the $C_T$ of FLIP for each sample, the following ratio was calculated: $C_T(FLIP)/C_T(GAPDH)$. The expression level of FLIP relative to the baseline level was calculated as $2^{-\Delta\Delta CT(FLIP)}$, where $\Delta CT$ is (average FLIP $C_T$–average GAPDH $C_T$) and $\Delta\Delta C_T$ is (average $\Delta C_T$ untreated sample–average $\Delta C_T$ treated sample.

Statistics. Cytotoxicity induced by compounds used in combination with conventional agents (e.g., CH-11, TRAIL, VP-16 and staurosporine) was evaluated for evidence of synergy toxicity by comparing the slopes of the dose-response curves. If the combination of the potential sensitizing compound with the conventional agent increased the slope of the dose-response curve compared to the slopes of either the sensitizer or the conventional agent alone, then the interaction was considered synergistic. If the slopes of the curves were not significantly different, it was concluded that the enhanced toxicity was additive but not synergistic. Statistical significance was defined as a $p<0.01$, using two-sided tests. Synergy was confirmed by performing multiple drug dose-effect calculations using the Median Effect methods as described in Chou (1991).

Results

Identification of Small Molecule FAS Sensitizers.

Resistance to death receptor ligands may permit malignant cells to escape immune surveillance and limit the clinical efficacy of recombinant death receptor ligands such as TRAIL. To identify small molecules that restore sensitivity to death receptor ligands, a cell-based high throughput screen was performed using the FAS and TRAIL-resistant prostate cancer cell line PPC-1 and a commercially available 50,000 compound library. The screens were performed in 96 well plates, to which compounds were added at 7.5 µg/ml (about 25 µM), followed by agonistic anti-FAS monoclonal antibody CH-11(100 ng/mL). Cell viability was measured 24 hours later by MTT assay. Each plate included controls of untreated cells, cells treated only with CH-11, and cells treated with a positive control compound, 2-cyano-3,12-dioxooleana-1,9-dien-28-oic acid (CDDO), previously determined to sensitize PPC-1 cells to TNF-family death receptors and ligands (Kim et al., 2002). The coefficient of variation (CV) for PPC-1 cells treated with CH-11 alone was determined to be 5%, based on 90 replicate determinations. A 50% decrease in cell viability was used as a cut-off for scoring hits.

From the primary screen of 50,000 compounds, 313 reproducible hits were obtained. FIG. 1 shows the overall workflow plan used to evaluate hits. To determine whether any of the 313 compounds were toxic molecules as opposed to FAS-sensitizers, the 313 compounds were evaluated in secondary screens where PPC-1 cells were treated with increasing concentrations of the compounds in the presence or absence of CH-11 antibody. Through these secondary screens, 9 sensitizers were identified that increased CH-11-mediated killing above the cell death produced by treatment of the cells with the compound alone (Table 1 and FIG. 2). In contrast, the remaining 304 compounds displayed toxicity as single agents, and did not potentiate CH-11-killing.

TABLE 1

| Chembridge ID | IUPAC Name | Structure |
| --- | --- | --- |
| 6094911 | N-[4-chloro-3-(trifluoromethyl)phenyl]-3-oxobutanamide | 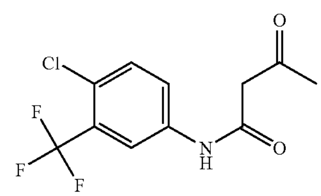 |
| 5809354 | 4-(2,4-dichlorophenoxy)-N-hydroxybutanamide | 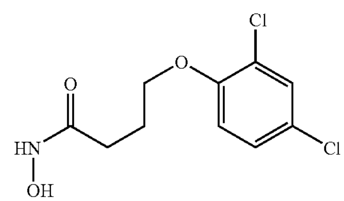 |
| 5703229 | 1-[(4-chlorophenyl)acetyl]-4-[(2e)3-phenylprop-2-enyl]piperazine | 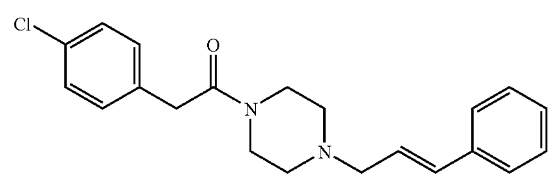 |
| 5687158 | 3,4,5-trimethoxy-N'-((5-methyltetrahydrofuran-2-yl)methyl)benzohydrazide | 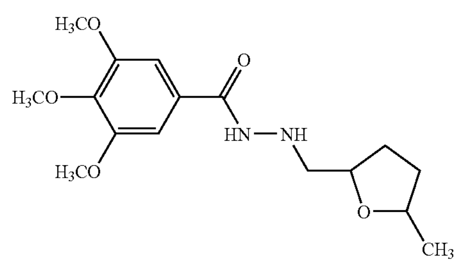 |
| 5557608 | 3,4-dimethyl-N-(3,4,5-trimethoxybenzyl)aniline | 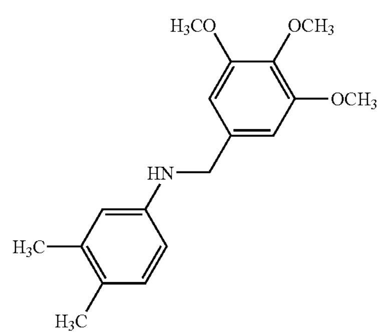 |

TABLE 1-continued

| Chembridge ID | IUPAC Name | Structure |
|---|---|---|
| 5647994 | N-(3-chloro-4-(isopentyloxy)benzyl)-imidodicarbonimidamide | 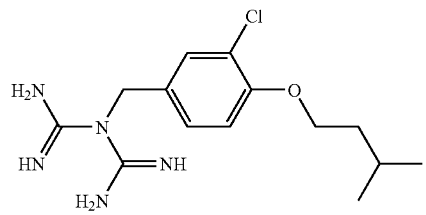 |
| 5362611 | 8-Cyclohexyl-3-methyl-5,6-dihydro-4H-pyrazino[3,2,1-jk]carbazol-3-ium; iodide | 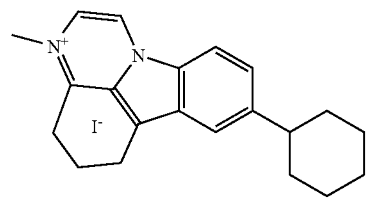 |
| 5541203 | 1-(3,5-Di-tert-butyl-4-hydroxy-phenyl)-2-(2-imino-3-methyl-2,3-dihydro-benzoimidazol-1-yl)-ethanone | 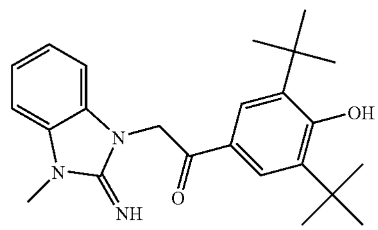 |
| 5569100 | 1-(3,5-Di-tert-butyl-4-hydroxy-phenyl)-2-(3-ethyl-2-imino-2,3-dihydro-benzoimidazol-1-yl)-ethanone | 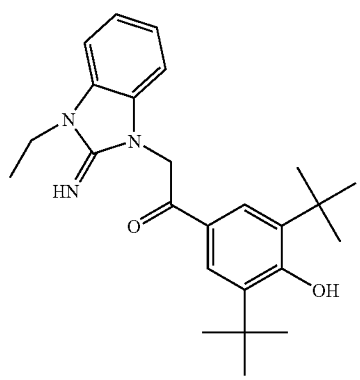 |
| 5529457 | 1-(3,5-di-tert-butyl-4-hydroxyphenyl)-2-(2-imino-3-(2-(piperidin-1-yl)ethyl)-2,3-dihydro-1H-benzo[d]imidazol-1-yl)ethanone hydrochloride | 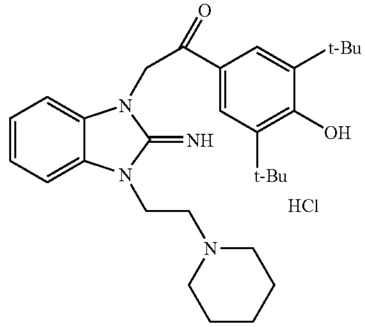 |

TABLE 1-continued

| Chembridge ID | IUPAC Name | Structure |
|---|---|---|
| 5651311 | 1-(3,5-di-tert-butyl-4-hydroxyphenyl)-2-(2-imino-3-(4-methylbenzyl)-2,3-dihydro-1H-benzo[d]imidazol-1-yl)ethanone hydrobromide | 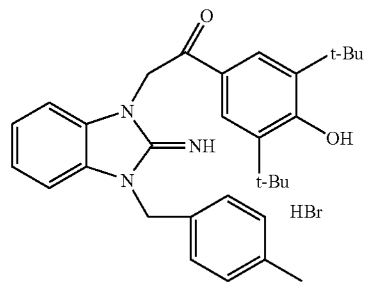 |
| 5657593 | 2-(3-benzyl-2-imino-2,3-dihydro-1H-benzo[d]imidazol-1-yl)-1-(3,5-di-tert-butyl-4-hydroxyphenyl)ethanone hydrobromide | 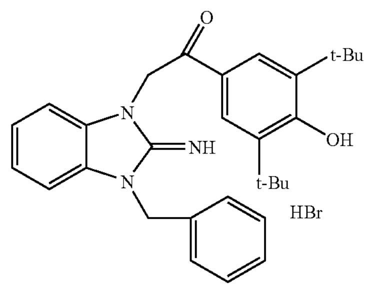 |
| 5569100 | 1-(3,5-di-tert-butyl-4-hydroxyphenyl)-2-(3-ethyl-2-imino-2,3-dihydro-1H-benzo[d]imidazol-1-yl)ethanone hydrobromide | 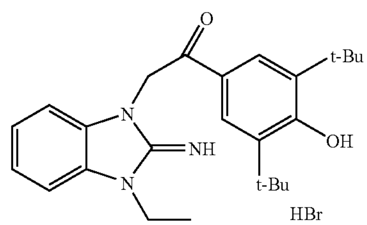 |
| 5541203 | 1-(3,5-di-tert-butyl-4-hydroxyphenyl)-2-(2-imino-3-methyl-2,3-dihydro-1H-benzo[d]imidazol-1-yl)ethanone hydrobromide | 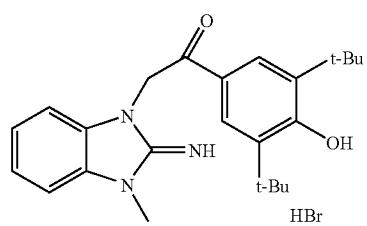 |

The identified molecules included compounds 5809354 (4-(4-chloro-2-methylphenoxy))-N-hydroxybutanamide and 6094911 (N-[4-chloro-3-(trifluoromethyl)phenyl]-3-oxobutanamide), which displayed little direct toxicity at concentrations up to 80 μM, but which sensitized PPC-1 cells to 100 ng/mL CH-11 with $LD_{50}$ of 20+2 μM and 35+4 μM, respectively (FIG. 2). In contrast, other compounds such as 5703229 (1-[(4-chlorophenyl)acetyl]-4-[(2E)-3-phenylprop-2-enyl] piperazine) were directly toxic with $LD_{50}$ of 50+5 μM, but sensitized to CH-11 at lower concentrations with an $LD_{50}$ of 34+4 μM (FIG. 2). Compounds 5809354, 6094911, and 5703229 demonstrated synergy when combined with CH-11 using the median-dose combination index (Chou, 1991; combination Index (CI)<1). In contrast, compound 5569100 did not demonstrate synergy with this method, likely reflecting the narrow range of concentrations over which 5569100 enhanced CH-11 killing.

Effects of Small Molecule Sensitizers on CH-11 Killing of a Spectrum of Malignant Cell Lines.

Figure 3:
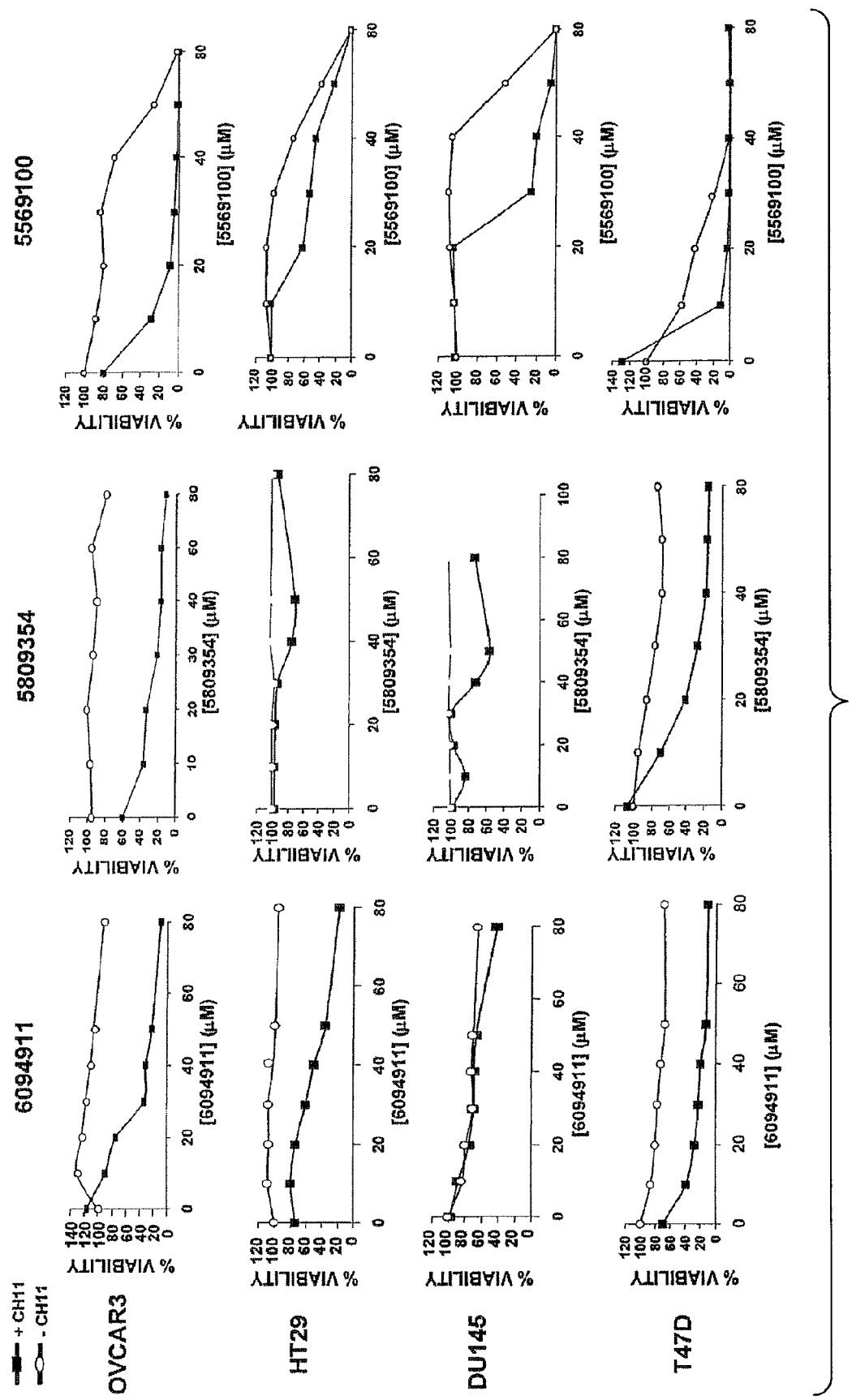
FIG. 3. Compounds 6094911, 5809354, and 5569100 sensitize a spectrum of tumor cells to CH-11 anti-FAS antibody. Solid tumor cell lines were seeded overnight in 96 well plates at a density of $1 \times 10^4$ cells per well. The next day, cells were treated with increasing concentrations of compound 6094911, 5809354, or 5569100 with (square) or without (circle) CH-11 antibody (100 ng/mL). Cell viability was measured 24 hours later by MTT assay. Cell viability is expressed as a mean percentage of untreated cells+SD (n=3).

To assess the spectrum of activity of the small molecule FAS sensitizers, an additional 9 malignant cell lines derived from breast, ovarian, and prostate carcinomas were treated with increasing concentrations of the sensitizers in the presence or absence of CH-11. Compound 6094911 sensitized 4 of 10 tumor cell lines to CH-11, including OVCAR-3 (ovarian), T47D (breast), HT29 (colon), and PPC-1 (prostate cancer) cells. Compound 5809354 sensitized the same tumor lines with the exception of HT29 (FIG. 3 and data not shown). None of the other compounds sensitized more than 4 of 10 tumor lines to CH-11. Among the non-responding tumor cell lines, for which 6094911 and 5809354 failed to sensitize, all except MDA-MB-468 expressed FAS antigen on the cell surface, as measured by flow cytometry using a specific fluorescinated antibody. Also, all of the non-responding cell lines, except Colo 205, had detectable levels of FLIP by immunoblotting (data not shown). Thus, the failure of 609411 and 5809354 to sensitize these tumor lines to anti-FAS antibody was not due to either lack of FAS expression or absence of FLIP, with rare exception.

Identification of Small Molecules that Specifically Sensitize to Extrinsic Pathway.

Figure 4:
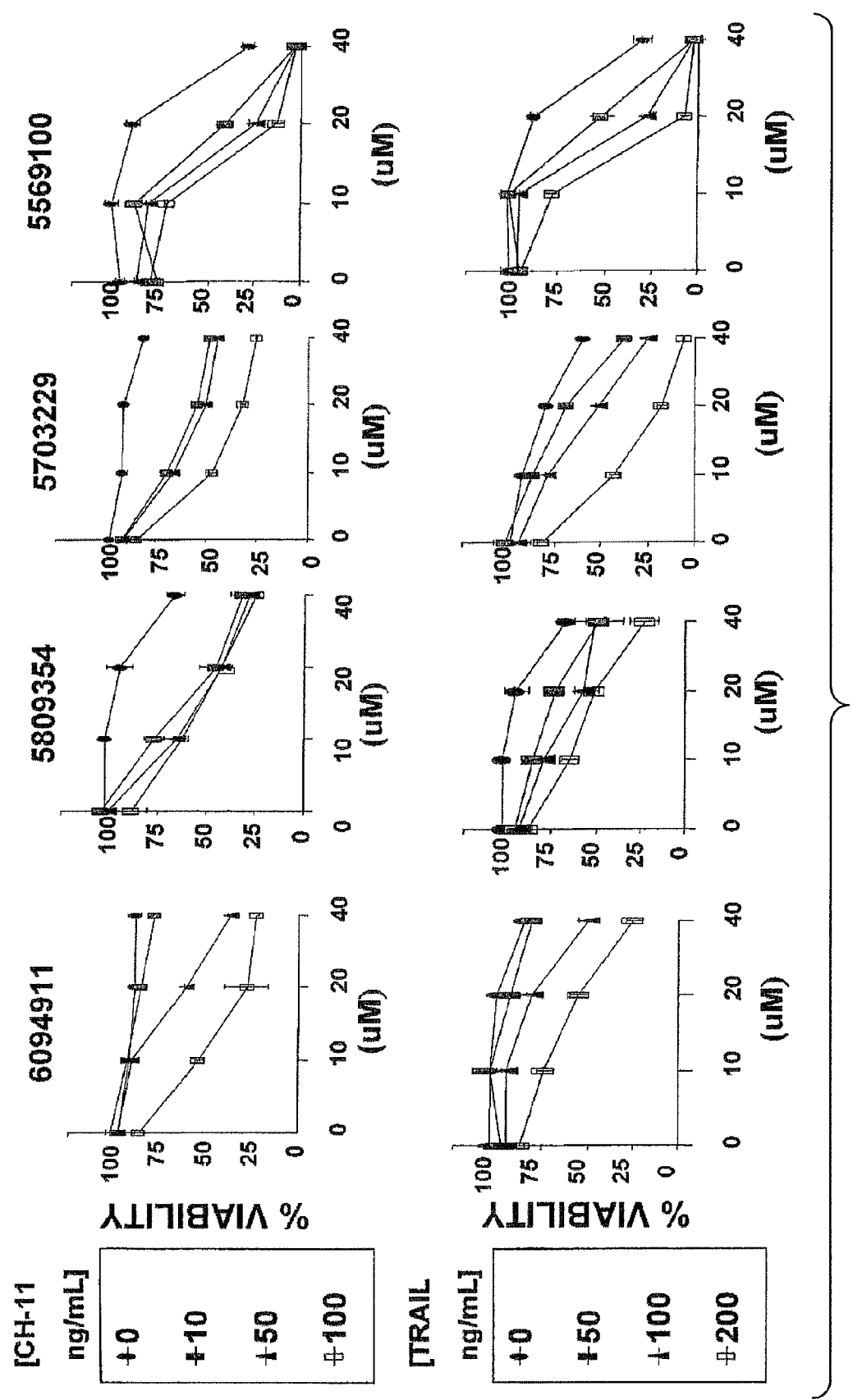
FIG. 4. Small molecules selectively sensitize to extrinsic pathway stimuli. PPC-1 cells ($1 \times 10^4$) were seeded overnight in 96 well plates. The next day, cells were treated with increasing concentrations of 6094911, 5809354, 5703229, or 5569100 in combination with increasing concentrations of CH-11 or TRAIL to activate the extrinsic pathway or with VP-16 or staurosporine to activate the intrinsic pathway. Cell viability was measured 24 hours later by MTT assay. Cell viability is expressed as a mean percentage of untreated cells+ SD(n=3).
Figure 5:
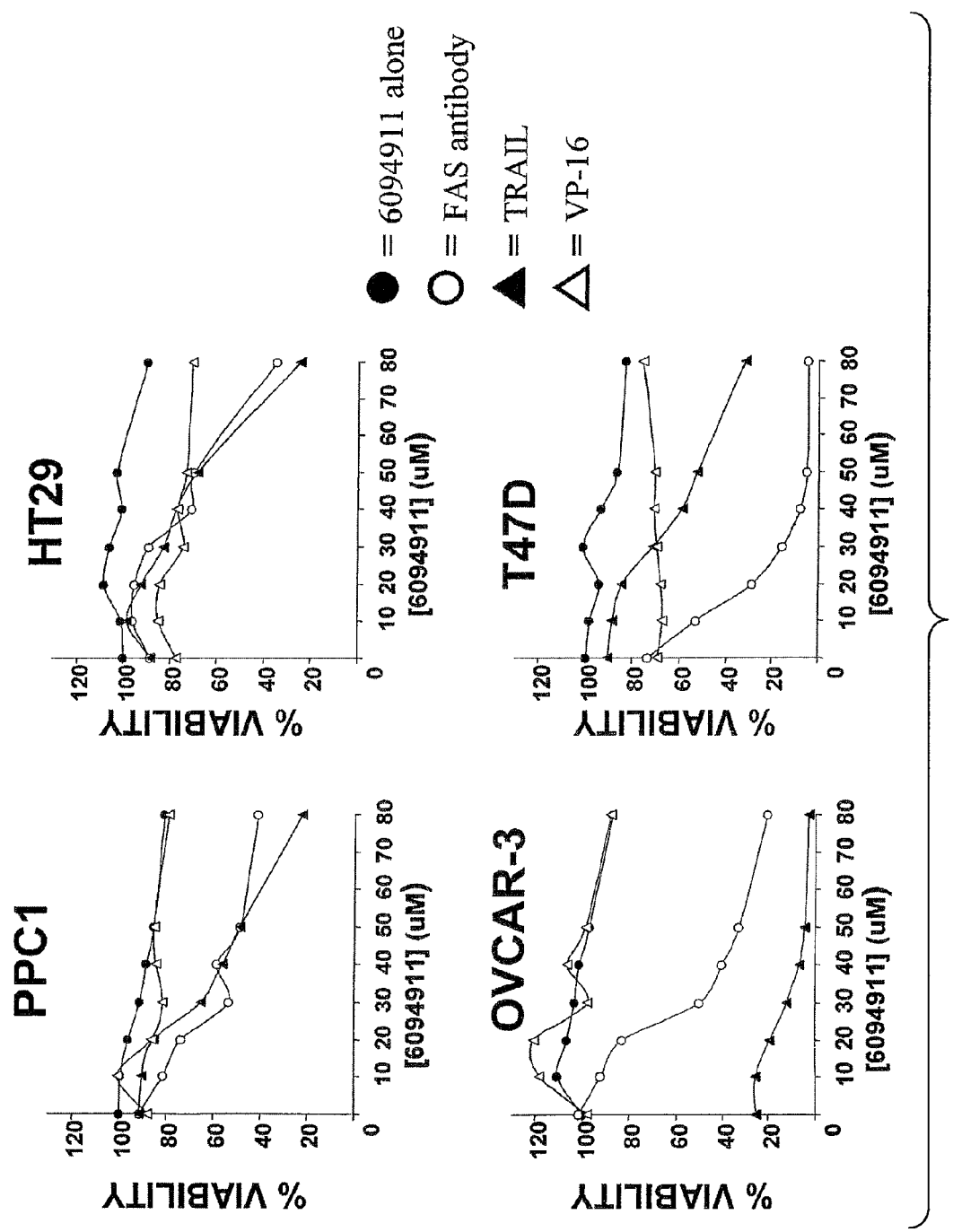
FIG. 5. Compound 6094911 selectively sensitizes tumor cell lines to extrinsic pathway stimuli. PPC-1 prostate, OVCAR-3 ovarian, HT29 colon, and T47D breast carcinoma cell lines were seeded overnight in 96 well plates ($10^4$ cells per well). The next day, cells were treated with increasing concentrations of 6094911 alone (closed circle) or in combination with CH-11 antibody (100 ng/mL) (open circle), TRAIL (200 ng/mL) (open triangle), or VP-16 (100 µM) (closed triangle). Cell viability was measured 24 hours later by MTT assay. Cell viability is expressed as a mean percentage+SD (n=3) relative to untreated cells.

The 9 compounds identified using anti-FAS antibody screening theoretically could non-specifically sensitize tumor cells to apoptotic stimuli or they could be selective for the extrinsic pathway. To distinguish between these two possibilities, the effects of compounds on apoptosis induced by extrinsic pathway stimuli (e.g., CH-11 antibody; TRAIL) were compared to the effects on the intrinsic pathway stimuli (e.g., etoposide [VP16]; staurosporine [STS]). Accordingly, PPC-1 cells were treated with various concentrations of compounds with or without CH-11, TRAIL, VP-16, or STS, and 24 hours later, cell viability was measured by MTT assays. Of the 9 candidate compounds, 8 sensitized PPC-1 cells to FAS and TRAIL (death receptor pathway stimuli) but not VP-16 or STS (intrinsic pathway stimuli), suggesting they selectively modulate the extrinsic pathway. Representative experiments with compounds 6094911, 5809354, 5703229, and 5569100 are shown in FIG. 4. In contrast, compound 5362611 sensitized to both the death receptor (extrinsic) and mitochondrial pathway (intrinsic) stimuli (FIG. 1), suggesting it operates downstream at the point of convergence of these two apoptotic pathways. Similar experiments were performed for compounds 6094911, 5809354, and 5569100 using OVCAR-3 and T47D tumor lines, confirming that the results are not unique to PPC-1 cells (FIG. 5 and data not shown).

Caspase-dependent Induction of Apoptosis by Combination Treatment with CH-11 and FAS-sensitizing Compounds.

Figure 6A:
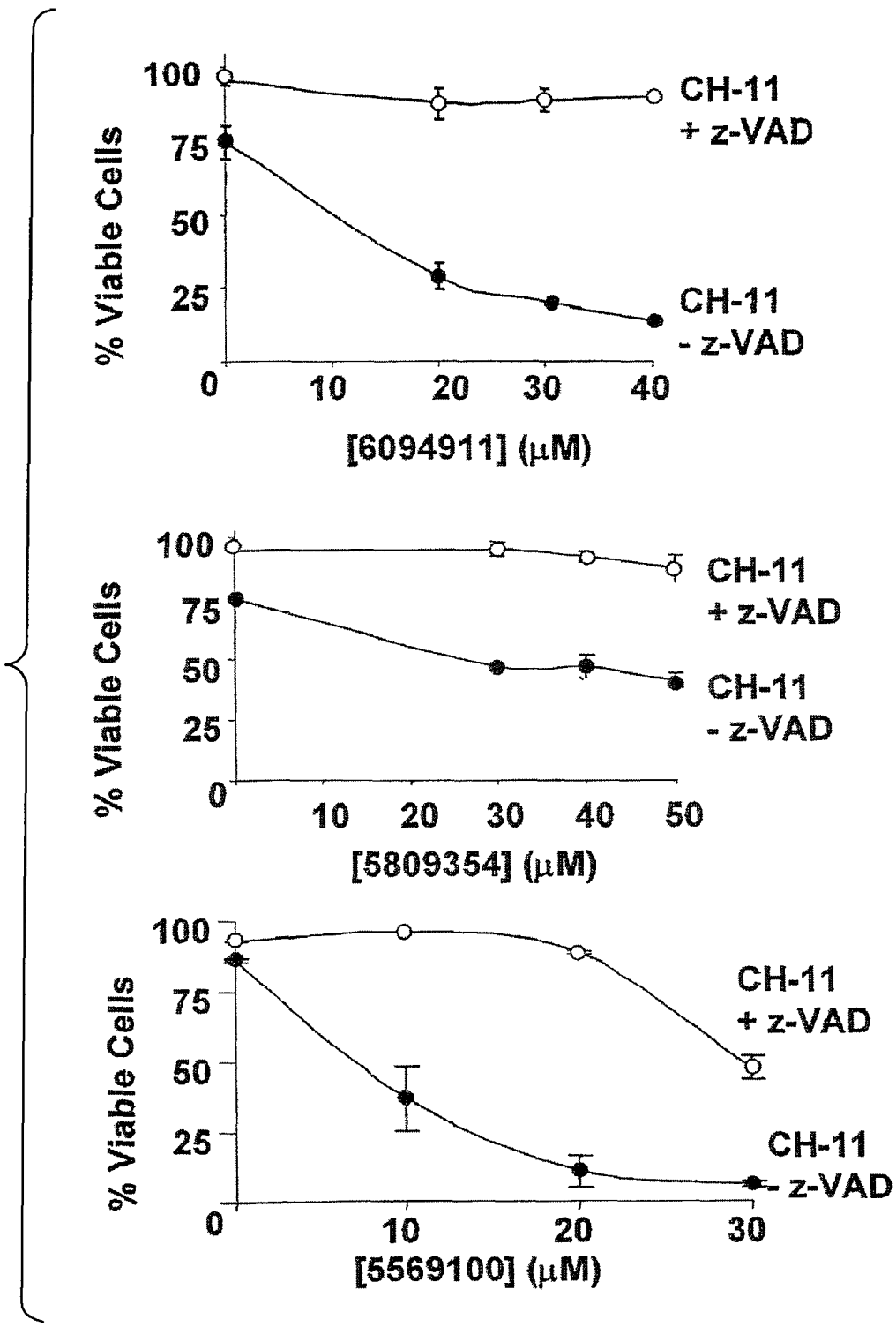
FIG. 6. Characterization of the mechanism of FAS-sensitizing compounds. (A) PPC-1 cells ($1\times10^5$) were seeded in 24 well plates. The next day, cells were treated with CH-11 antibody (100 ng/mL) and 30 µM 6094911, 5809354, or 5569100 with (square) or without (diamond) caspase inhibitor z-VAD-fmk (100 µM). Apoptosis was measured 24 hours later by Annexin V staining, expressing data as percentage of Annexin V-negative ("viable") cells (mean+SD) (n=3). (B) PPC-1 cells ($2\times10^5$) were seeded in 6 well plates and co-transfected with plasmids encoding Bcl-XL, CrmA, or empty vector along with a green fluorescent protein (GFP) encoding plasmid to identify successfully transfected cells. After 48 hours, cells were treated with CH-11 antibody (100 ng/mL) and 6094911 (30 µM), 5809354 (30 µM), or 5569100 (15 µM). As a positive control, transfected cells were treated with staurosporine (0.5 µM) (STS). Apoptotic cells were identified by morphological assessment of the GFP-positive cells, and data were expressed as the percentage of nonapoptotic ("viable") cells (mean+SD) (n=3).

To further assess the mechanism of the 8 compounds that selectively modulated tumor sensitivity to extrinsic pathway stimuli, the effects of benzoyl-Val-Ala-Asp-fluoromethylketone (zVAD-fmk), a broad-spectrum irreversible inhibitor of caspase-family proteases (Enzyme Systems, Dublin, Calif.) was tested. Accordingly, PPC-1 cells were treated with CH-11 and sensitizers such as 6094911, 5809354, and 5569100 with and without zVAD-fmk (100 µM) for 12 hours. Apoptosis was then measured by annexin V staining. Consistent with a caspase-dependent mechanism of action, zVAD-fmk blocked sensitization to CH-11 (FIG. 6A). Likewise, the caspase-8 inhibitory compounds acetyl-Isoleucinyl-Glutamyl-Threoninyl-Aspartyl-fluoromethylketone (Ac-IETD-fmk) (Calbiochem, San Diego, Calif.) also inhibited apoptosis induced by CH-11 in combination with these FAS-sensitizing compounds (data not shown).

To further address the specificity of the compounds for the extrinsic pathway, the effects of selective apoptosis inhibitory genes were examined. For these experiments, PPC-1 cells were transfected with plasmids encoding CrmA, a viral protein that blocks the extrinsic pathway by inhibiting caspase-8 (Zhou et al., 1997) or encoding Bcl-xL, a mitochondria-targeting protein that blocks the intrinsic pathway by inhibiting release of cytochrome c (Boise et al., 1993; Kharbanda et al., 1997). After transfection, cells were treated with CH-11 antibody and compounds 6094911, 5809354, or 55619100 scoring the percentage of apoptotic cells among the successfully transfected cells as determined by co-transfection of a GFP-marker plasmid.

Figure 6B:
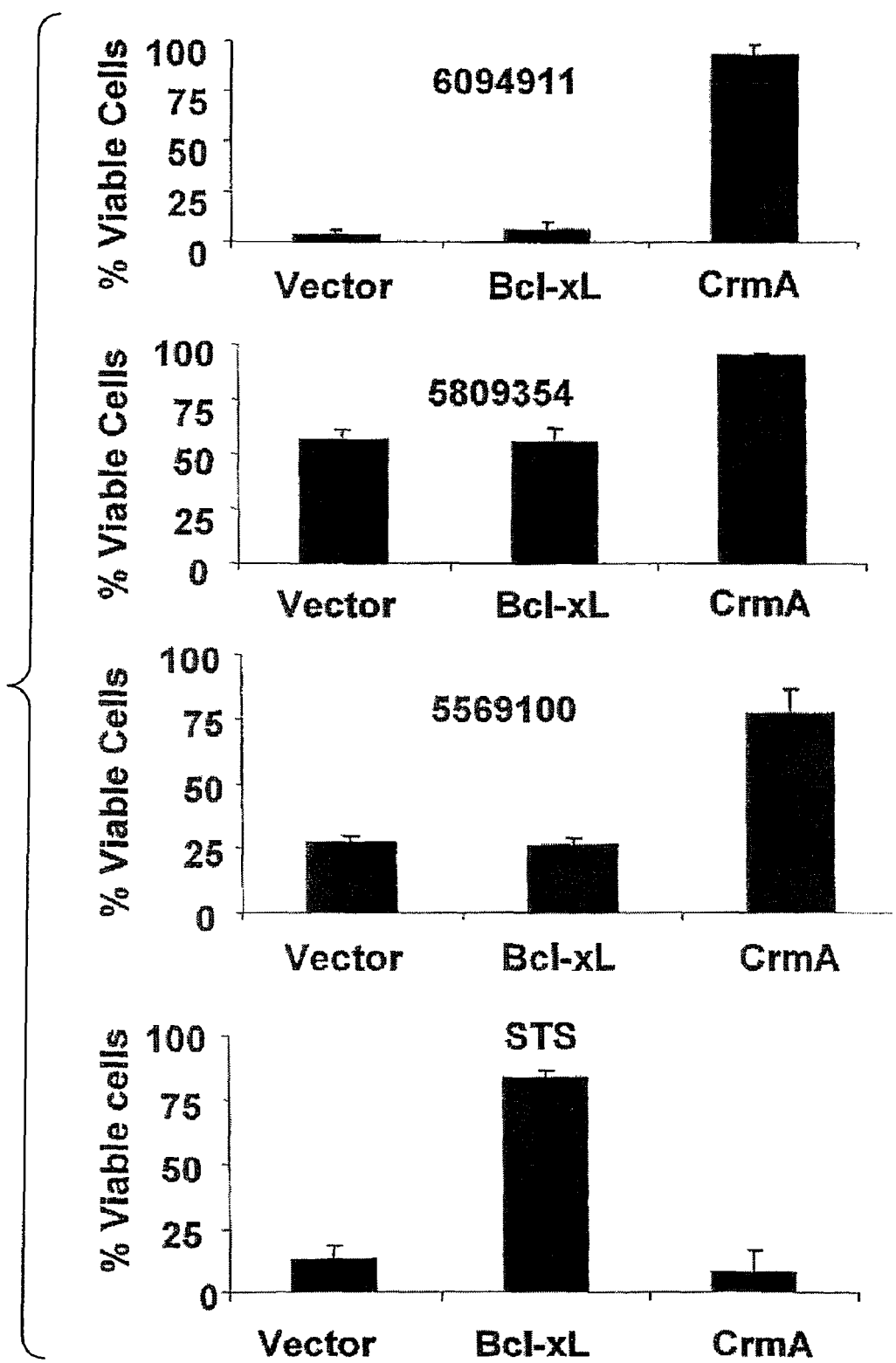

CrmA almost completely protected against apoptosis induced by the combination of CH-11 and either 6094911, 580935, or 5569100 while Bcl-XL had no protective effect (FIG. 6B). As a positive control, transfection of Bcl-XL but not Crm A protected PPC-1 cells from STS-induced apoptosis. Taken together, these results indicate that molecules such as 6094911, 5809354, and 5569100 specifically target the death receptor (extrinsic) pathway proximal to its convergence with the mitochondrial (intrinsic) pathway at the level of downstream effector caspases. Furthermore, since these compounds sensitize to both FAS and TRAIL, they presumably act distal to death receptors. Supporting this hypothesis, treatment of PPC-1 cells with either 6094911, 5809354 or 5569100 did not change the surface expression of FAS or TRAIL receptors, as measured by flow cytometry using specific fluorescinated antibodies (data not shown).

Effects of Sensitizing Compounds on FLIP Protein.

The intra-cellular protein FLIP (c-Fas-associated death domain-like IL-1-converting enzyme-like inhibitory protein) is a key inhibitor of death receptor signalling (Schimmer, 2004; Krueger et al., 2001). As a dominant negative homolog of caspase 8, FLIP binds directly to FADD and inhibits DISC-mediated caspase 8 activation (Irmler, 1997; Yeh et al., 2000). Importantly, FLIP is overexpressed in a number of solid and hematological tumors and as such, allows tumor cells to escape death receptor signalling (Thome et al., 2001; Reed, 2006). Similarly, down-regulation of FLIP in cell culture by small molecules, antisense oligonucleotides, or RNA interference sensitizes Fas-resistant cells to Fas-mediated apoptosis (Kim et al., 2002; Schimmer et al., 2006; Perlman et al., 1999).

Figure 7A:
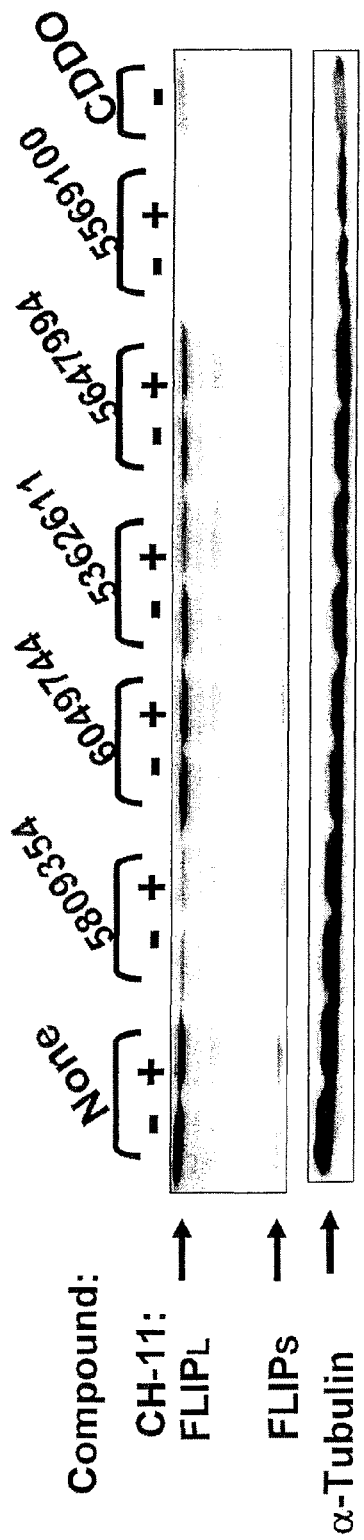
FIG. 7. Effect of FAS-sensitizing compounds on levels of FLIP protein and DISC activation. (A) PPC-1 cells ($2\times10^5$) were seeded into 35 mm plates and treated the next day with various FAS-sensitizing compounds (30 µM), with (+) or without (−) CH-11 antibody (100 ng/mL). As a positive control, cells were treated with CDDO (5 µM). Cell lysates were prepared 24 hours later, normalized for total protein content, and analyzed by SDS-PAGE/immunoblotting using antibodies specific for FLIP or a-tubulin. (B) PPC-1, OVCAR-3, T47D, MDA-MB-468 and DU 145 cells ($2\times10^5$) were seeded into 35 mm plates and treated the next day with 5809354 (40 µM). Cell lysates were prepared 24 hours after treatment, normalized for total protein and analyzed by SDS-PAGE/ immunoblotting using antibodies specific for FLIP or β-actin. (C) PPC-1, OVCAR-3, T47D, and DU 145 cells ($2\times10^5$) were seeded into 35 mm plates and treated the next day with 5809354 (40 µM) (black bars) or buffer control (white bars). mRNA was extracted 24 hours after treatment. Levels of the long isoform of FLIP and GAPDH were detected by quantitative RT-PCR. Levels of FLIP were normalized for GAPDH expression and expressed as a mean fold change+SD over buffer treated cells. (D) PPC-1 cells ($2\times10^5$) were seeded into 35 mm plates and treated the next day with various FAS-sensitizing compounds (30 µM) with (+) or without (−) CH-11 (100 ng/mL). Cell lysates were prepared 24 hours after treatment, normalized for total protein, and analyzed by SDS-PAGE/immunoblotting using antibodies specific for caspase-8 and β-actin.

Since FAS-sensitizing compounds 6094911 and 5809354 modulate the extrinsic pathway downstream of TNF-family death receptors but upstream of effector caspases, the effects of those compounds on expression of FLIP, an intracellular antiapoptotic protein that binds caspases-8 and -10 and is capable of suppressing death receptor signaling at a proximal point within the extrinsic pathway, was examined. For these experiments, PPC-1 cells were treated with sensitizing compounds in the presence or absence of CH-11 antibody, then cell lysates were prepared 24 hours later, and analyzed by immunoblotting for FLIP (FIG. 7A). Comparisons were made with the triterpenoid, CDDO, which was previously shown to reduce FLIP protein levels and restore sensitivity of tumor cells to FAS and TRAIL (Kim et al., 2002), thus serving as a positive control.

Figure 7B:
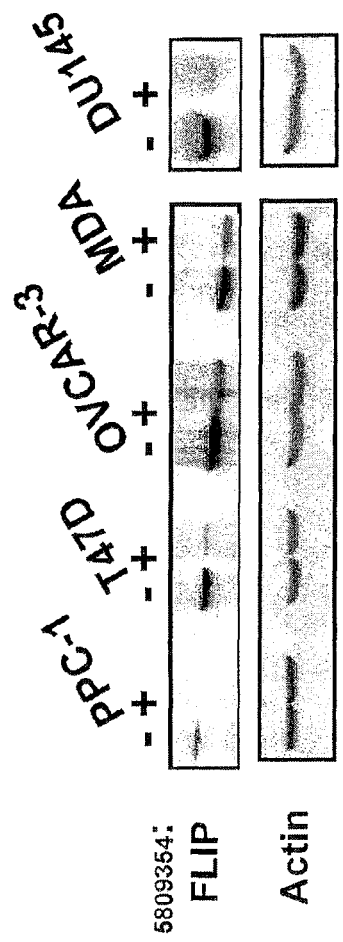

The levels of the short isoform of FLIP were <5% of total FLIP protein as measured by immunoblotting and quantitative densitometry. Therefore, given the very low levels of the short isoform, the analysis was limited to the effects of the compounds on the long isoform of FLIP. Compounds 5809354 and 5569100 decreased levels of FLIP protein. Pre-treatment with z-VAD-fmk did not prevent reductions in FLIP protein, indicating that the changes in FLIP were not a secondary event mediated by caspase activation. In contrast, the other FAS-sensitizing compounds did not alter FLIP expression, indicating that they act through different mechanisms. Similar reductions in FLIP protein were observed after treating OVCAR-3, and T47D cells with 5809354. Likewise, levels of FLIP were decreased in the non-responding cell lines DU145 and MDA-MB-468 after treatment with 5809354 (FIG. 7B). While these compounds reduced levels of FLIP protein, no change in levels of Bcl-2, FADD, caspase-8, or Mcl-1 were observed after treatment with these compounds (data not shown).

Figure 7C:
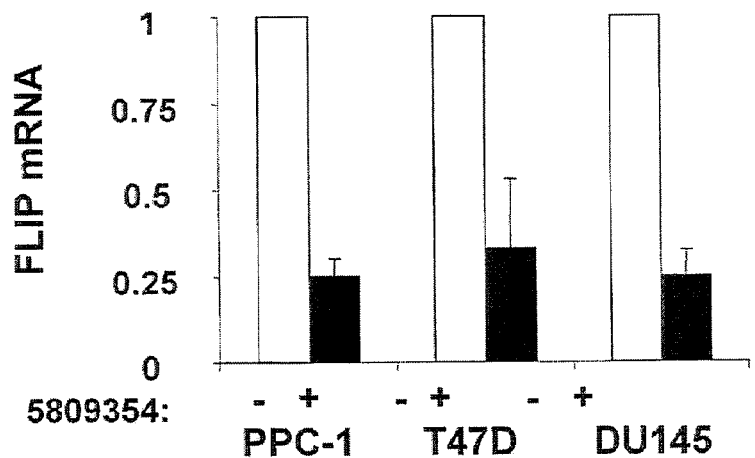

To determine whether the reductions in FLIP protein occurred at the level of mRNA or protein, FLIP mRNA expression was measured by Quantitative RT-PCR in cells treated with 5809354 or buffer control. Treatment with 5809354 reduced expression of FLIP mRNA in the responding and non-responding cell lines (FIG. 7C). In contrast, compounds 5569100 and 6094911 did not reduce FLIP mRNA (data not shown).

Figure 7D:
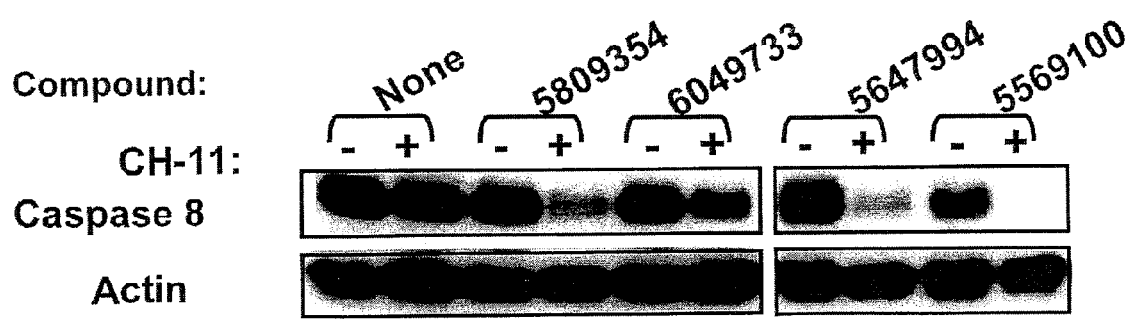

To determine whether the compounds activate the DISC in the presence of CH-11, processing of caspase-8 was analyzed by immunoblotting. Treatment of cells with the sensitizers and CH-11 activated caspase-8, as evidenced by a decrease in the proform of caspase-8 and an increase in the cleaved form (FIG. 7D and data not shown).

Figure 8A:
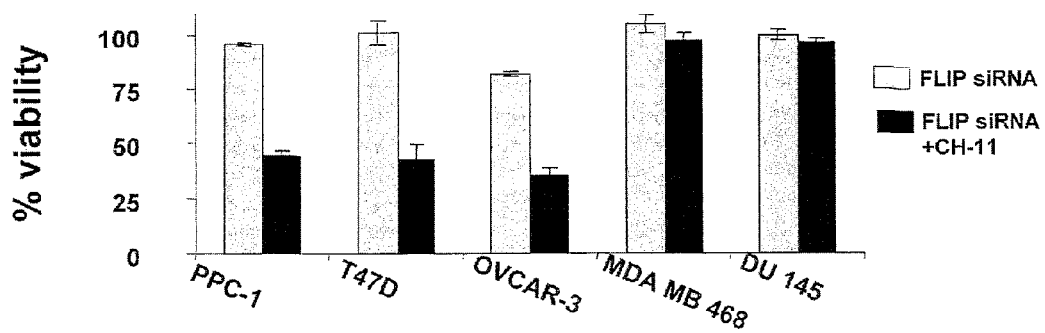
FIG. 8. Decreases in FLIP by compound 5809354 are functionally important. (A) PPC-1, OVCAR-3, T47D, and DU 145 cells ($2\times10^5$) were seeded into 35 mm plates and transfected with double-stranded siRNA targeting FLIP (f), control ds RNA (c), or mock transfected with buffer alone (m). At 24 hours after transfection, cells were treated with CH-11 (100 ng/mL) or buffer control. Cell viability was measured by an MTS assay and expressed as a percentage of untreated control cells (mean+SD; n=3). (B) Levels of FLIP protein were measured by immunoblotting. (C) PPC-1 cells ($2\times10^5$) were seeded into 35 mm plates and transfected with siRNAs (10 nM) targeting FLIP or luciferase as a control (CNTRL). At 24 hours after transfection, cells were treated with increasing concentrations of 5809354 with or without CH-11 anti-FAS antibody (100 ng/mL) for an additional 24 hours. Cell viability was measured by an MTS assay, and expressed as a percentage of control untreated cells (mean+ SD; n=3).
Figure 8B:
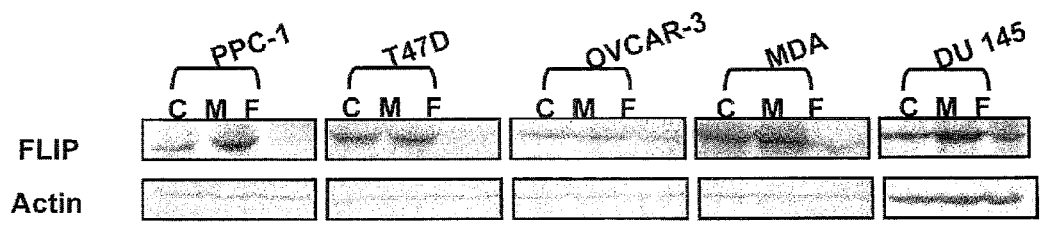
Figure 8C:
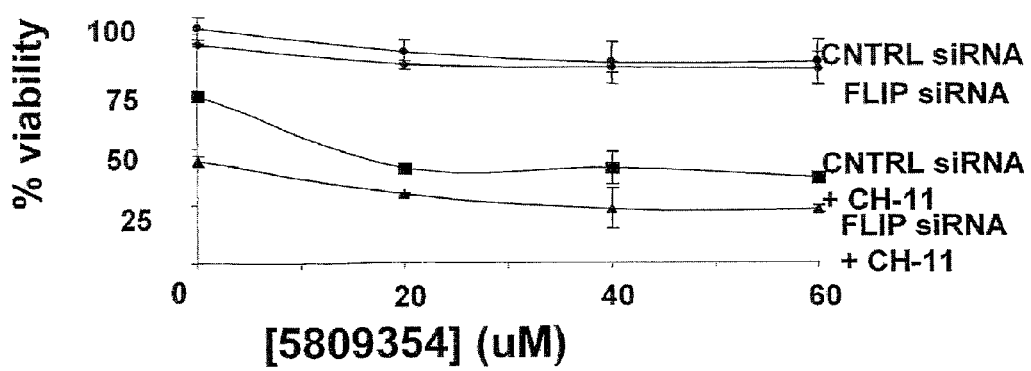

To test the functional importance of decreases in FLIP by 5809354, it was determined whether knocking down FLIP could recapitulate the activity of the molecule and abrogate 5809354's ability to sensitize cells to CH-11. PPC-1 cells were transfected with double stranded siRNA that targeted FLIP or luciferase as a control. At 24 hours after transfection, cells were treated with increasing concentrations of 5809354 with or without CH-11. FLIP siRNA, but not luciferase double-strand ds RNA control, sensitized PPC-1, OVCAR-3, and T47D, but not MDA-MB-468 and DU 145 cells, to CH-11, thereby recapitulating the effects of 5809354 (FIG. 8A). Furthermore, in the presence of FLIP siRNA, 5809354 the longer enhanced CH-11-mediated killing (FIG. 8B). Thus, taken together, the data suggest that decreases in FLIP by 5809354 are functionally important.

Structure Activity Relation (SAR) Analysis.

Figure 9:
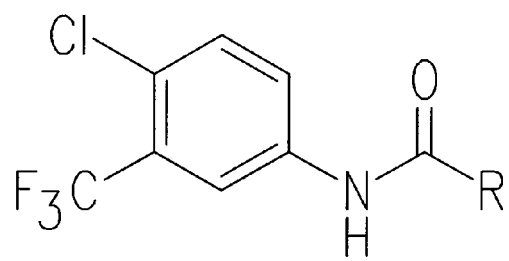
FIG. 9. Structure-activity relation (SAR) analysis of compound 6094911. The chloride substituted 3-trifluor-methyl-phenyl-amide represents the core pharmacophore responsible for FAS-sensitizing activity of 6094911.
Figure 10:
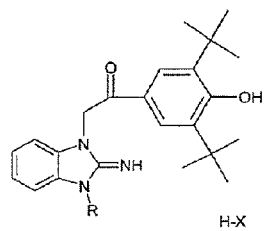
FIG. 10. Activity of compounds related to compound 5541203.

To begin exploring the relationship between the structure and function of the FAS sensitizing compounds, a series of structurally related analogs of 6094911 were evaluated. PPC-1 cells were treated with increasing concentrations of the analogues, with and without CH-11(100 ng/mL), and cell viability was measured by a MTT assay 24 hours later, and approximate $LD_{50}$ values determined (Table 2, $LD_{50}$ is the concentration of compound that reduces cell viability by 50%). Comparison of the analogs indicated that modifications of the 4-chloro-3-(trifluoromethyl)-phenyl group abolished or significantly reduced activity of the compounds. Conversely, various substituents are well tolerated in the R position (FIG. 9 and Table 2). These results suggest that the N-[4-chloro-3-(trifluoromethyl)-phenyl]-amide moiety contains a pharmacophore for the activity of 6094911, while the methyl-keto moiety is expendable (Table 2).

TABLE 2

| Name | Structure | $LD_{50}$ (μM) (PPCl, CH-11) | $LD_{50}$ (μM) PPCl |
|---|---|---|---|
| N-[4-chloro-3-(trifluoromethyl)phenyl]-3-oxobutanamide | 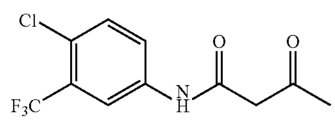 | 35 ± 4 | >100 |
| N-[4-chloro-3-(trifluoromethyl)-phenyl]-3-phenyl-proionamide | 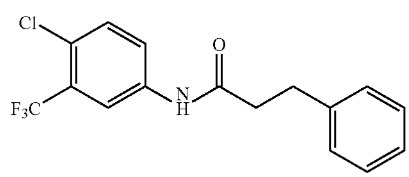 | 11 ± 1 | 85 ± 3 |
| N-(4-Chloro-3-trifluoromethyl-phenyl)-3-[(pyrazine-2-carbonyl)-hydrazono]-butyramide | 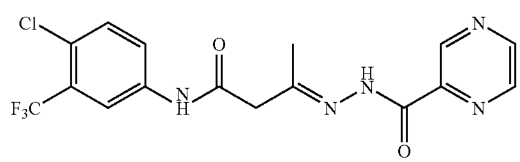 | 11 ± 3 | 67 ± 3 |
| N-[4-chloro-3-(trifluoromethyl)phenyl]-2-thiophenecarboxamide | 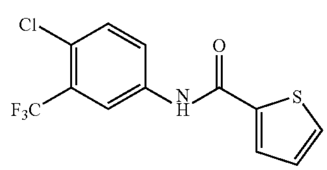 | 35 ± 11 | 96 ± 1 |
| N-[2-chloro-5-(trifluoromethyl)phenyl]-3-oxobutanamide | 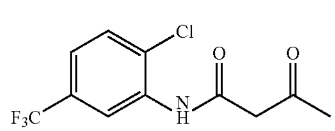 | 65 ± 5 | 75 ± 1 |
| N-[2-chloro-5-(trifluoromethyl)phenyl]-3-phenylpropanamide | 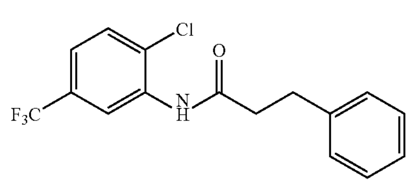 | >100 | >100 |

TABLE 2-continued

| Name | Structure | LD$_{50}$ (μM) (PPCl, CH-11) | LD$_{50}$ (μM) PPCl |
|---|---|---|---|
| N-[4-chloro-2-(trifluoromethyl)phenyl]-3-phenylpropanamide | 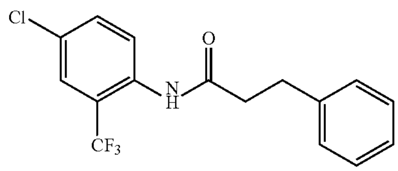 | >100 | >100 |
| 1-(3,5-di-tert-butyl-4-hydroxyphenyl)-2-(2-imino-3-(2-(piperidin-1-yl)ethyl)-2,3-dihydro-1H-benzo[d]imidazol-1-yl)ethanone hydrochloride | 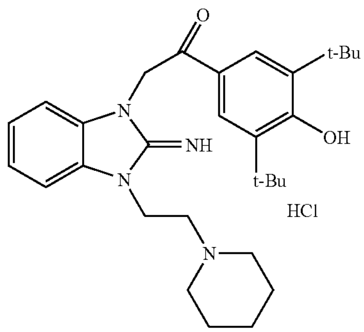 | 3.7 | 7.5 |
| 1-(3,5-di-tert-butyl-4-hydroxyphenyl)-2-(2-imino-3-(4-methylbenzyl)-2,3-dihydro-1H-benzo[d]imidazol-1-yl)ethanone hydrobromide | 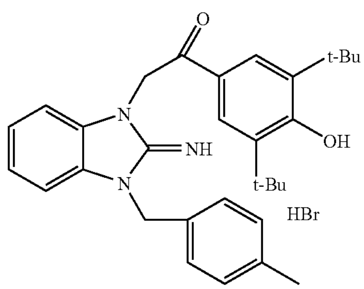 | 9 | 19 |
| 2-(3-benzyl-2-imino-2,3-dihydro-1H-benzo[d]imidazol-1-yl)-1-(3,5-di-tert-butyl-4-hydroxyphenyl)ethanone hydrobromide | 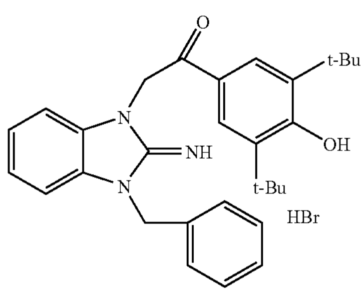 | 3.4 | 9.1 |
| 1-(3,5-di-tert-butyl-4-hydroxyphenyl)-2-(3-ethyl-2-imino-2,3-dihydro-1H-benzo[d]imidazol-1-yl)ethanone hydrobromide | 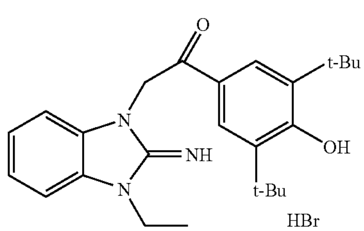 | 5.6 | 15 |
| 1-(3,5-di-tert-butyl-4-hydroxyphenyl)-2-(2-imino-3-methyl-2,3-dihydro-1H-benzo[d]imidazol-1-yl)ethanone hydrobromide | 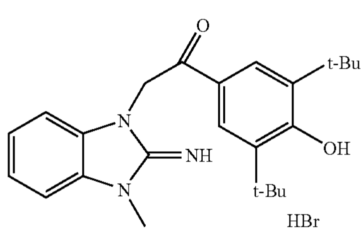 | 25.7 | 45.4 |

Among the nine active compounds originally identified, two have very similar structures, 5569100 and 5541203 (Table 1). These compounds differ only by the presence of an ethyl versus a methyl substitution on the position 3 of the dihydrobenzoimidazol group, in 5569100 and 5541203, respectively. 5569100 is approximately 5-times more potent than 5541203 as a FAS-sensitizer in PPC1 cells (EC50 5.6 µM versus 25.7 µM) but also is 3-times more toxic when added alone (without anti-FAS antibody) to cultures of PPC1 cells (LD50 15 µM versus 45 µM). Interestingly, while 5569100 reduced FLIP expression when applied to tumor cells by itself (without anti-FAS antibody), 5541203 had little effect. This observation implies that substitution of long alkyl groups to the dihydro-benzoimidazol ring may favor FLIP suppression. Additional substitutions at this position in the dihydro-benzoimidazol ring of 5569100 may provide further compounds with improved potencies.

Discussion

Most high throughput screens are designed to identify molecules that interact with specific protein targets. In contrast, the study described here utilized a chemical biology approach to identify molecules that reverse the phenotype of FAS resistance. With the cell-based, high throughput assay, 9 compounds were identified from a library of 50,000 that reversed resistance of PPC-1 cells to CH-11 anti-FAS antibody. The molecules differed in their dose-response curves with some compounds displaying FAS-independent toxicity at higher doses, while enhancing death receptor-mediated killing at lower concentrations. Some compounds such as 5934859 reversed FAS resistance only for PPC-1 cells, while other compounds such as 6094911 were more broadly acting, sensitizing 4 of 10 tumor lines to extrinsic pathway stimuli. These differences among compounds likely reflect different mechanisms of action and different cellular targets, combined with differences in FAS-resistance mechanisms among tumor cell lines. Differences in activity between cell lines may also reflect differential requirements for amplification of death receptor stimuli through the mitochondrial pathway. For example, type II cells require amplification of death receptor stimuli through the mitochondrial pathway of caspase activation to effectively induce apoptosis (Scaffidi et al., 1998). In these cells, blocks in the mitochondrial pathway can render these cells resistant to FAS, and thus could potentially account for resistance in the identified compounds. In type I cells, in contrast, death receptor stimuli do not require amplification through the mitochondrial pathway (Scaffidi et al., 1998). Of course, variations in uptake and metabolism of compounds may also contribute to the heterogeneous responses among tumor lines.

Of the 9 sensitizers to CH-11 identified by this screen, 8 sensitized to the extrinsic pathway agonists CH-11 and TRAIL but not to cell death stimuli that trigger the intrinsic pathway such as VP-16 and staurosporine. Furthermore, FAS-sensitization by these 8 compounds was inhibited by CrmA but not Bcl-XL, consistent with a selective effect on the extrinsic pathway. These results indicate that these compounds act selectively on targets in the extrinsic pathway, operating distal to death receptors but proximal to downstream effector caspases.

Previous studies have shown that PPC-1 cell resistance to FAS and TRAIL can be reversed by decreasing the levels of the caspase-8 inhibitor FLIP using antisense oligonucleotides or the triterpenoid CDDO, which reduces FLIP expression (Kim et al., 2002). Therefore, the effects of some of the compounds on levels of FLIP protein was assessed. Two of the compounds identified decreased levels of FLIP protein. The decrease in FLIP was not secondary to caspase activation, based on experiments using broad-spectrum caspase inhibitor zVAD-fmk. Reducing expression of endogenous FLIP using siRNA-based gene silencing recapitulated the ability of 5809354 to sensitize tumor cells to CH-11 and abrogated the ability of 5809354 to sensitize tumors further to CH-11. These data argue that FLIP is an important target of this compound, since the absence of the target nullifies the actions of 5809354 with respect to FAS-sensitization. 5809354 decreased FLIP mRNA and thus appears to act through a mechanism different than CDDO, which reduces FLIP protein by promoting its ubiquitination (Kim et al., 2002). Of note, other extrinsic pathway modulating compounds such as 6094911 did not alter levels of FLIP protein, indicating that they act through different mechanisms.

A preliminary analysis was conducted to determine functional groups important for the activity of one of the compounds, 6094911, which enhanced FAS-induced killing of several tumor cell lines. For compound 6094911, the N-[4-chloro-3-(trifluoromethyl)-phenyl]-amide moiety appeared necessary for activity. Moving the trifluoromethyl group from the third position of the phenyl ring abolished activity of an active analog, as did moving the chloro atom from the fourth position. In contrast, a variety of substitutions are well tolerated at the R group suggesting that this position is not critical for the FAS-sensitizing activity of the compounds. Accordingly, the compounds could be derivatized at this position with affinity labels (i.e., biotin) that could results very useful to identify cellular targets of 6094911. Furthermore, the initial SAR data reported here provide some guidance for the design and synthesis of second generation compounds that may be more potent than the parent and potentially more amenable to clinical use.

In summary, compounds were identified that sensitize a spectrum of resistant cancer cells to death receptor ligand stimulation. These compounds may serve as prototypes for development of novel therapeutic adjuncts for the treatment of malignancy based on immune-based treatments such as recombinant TRAIL, agonistic anti-TRAIL antibodies, or tumor vaccines. In addition, these compounds provide new research tools for chemical biological experiments aimed at understanding mechanisms of resistance to TNF-family death ligands and death receptors.

EXAMPLE 2

Materials and Methods

Reagents. Anti-Fas monoclonal antibody CH-11 was purchased from MBL (Nagoya, Japan). Staurosporine was purchased from Sigma-Aldrich (Oakville, ON, Canada). z-VAD-fmk was purchased from Calbiochem (San Diego, Calif., USA). 5809354 ((4-(4-chloro-2-methylphenoxy))-N-hydroxybutanamide) and 7271570 ((4-(4-chloro-2-methylphenoxy))-N-(3-ethoxypropyl)-butanamide) were obtained from Chembridge (San Diego, Calif., USA).

Cell culture. SV40-transformed wild-type and FLIP knockout MEFs (gifts from S. Benchimol and Y. C. Yeh, Princess Margaret Hospital) and E1A-transformed wild-type and caspase 8 knockout MEFs (gifts from S. Benchimol and R. Hakem, Princess Margaret Hospital) were maintained in DMEM media. PPC-1, PC-3, DU-145, LNCaP, T47D, and OVCAR-3 cells were maintained in RPMI 1640 media. DLD-1, DKS-8, and MB-MDA-468 were maintained in DMEM media. All culture media was supplemented with 10% fetal bovine serum (Hyclone, Logan, Utah, USA) and antibiotics. DsRED-PPC-1 cells were engineered by transfecting PPC-1 cells with pdsRed2-C1 (Clontech Laboratories, Mountainview, Calif., USA). Cells stably expressing dsRed2 protein were selected with 1 mg/mL G418 for 5 days, and G418-resistant colonies were pooled and enriched for dsRed2 expression using a MoFlo fluorescent activated cell sorter (Dako, Mississauga, ON, Canada). All cells were grown on tissue culture treated polystyrene for adherent conditions or on hydrogel-coated ultra-low binding plates for suspension conditions (Corning, Acton, Mass., USA). Cells in suspension were gently pipetted at least once during the suspension culture to prevent the formation of stable cell spheroids. All cells were cultured at 37° C. in a humid atmosphere with 5% $CO_2$.

Cell viability apoptosis, colony formation, and caspase activation assays. Cell viability was assessed using the MTS reduction assay (Promega, Madison, Wis., USA) according to the manufacturer's protocols and as described in Schimmer et al. (2006). Apoptosis was measured by flow cytometry to detect cell surface annexin V expression and propidium iodide (PI) uptake (Biovision, Mountain View, Calif., USA) as described in Carter et al. (2005). Image-based nuclear fragmentation assays were conducted as an independent measure of apoptosis. Cells were harvested, fixed with 4% (v/v) paraformaldehyde in PBS, and stained with 800 nM DAPI dilactate (Molecular Probes, Carlsbad, Calif., USA). Samples were imaged on a Zeiss Axiovert 200M with a Zeiss A-Plan 32×/0.40 NA Ph I lens using a 360 nM excitation and 460 nM emission filter set, a Coolsnap HQ camera (Roper Scientific, Tucson, Ariz., USA), and Image Pro PLUS software (Media Cybernetics, Silver Spring, Md., USA). Clonogenic growth after suspension culture was measured using colony formation assays. Briefly, equal volumes of suspension-cultured cells were seeded into 6-well plates and grown in adherent conditions for one week. Colonies were fixed, stained with methylene blue, and counted. Caspase activation in intact cells was measured by flow cytometry using FITC-labelled cell permeable peptides that bind preferentially and reversibly to caspases 3, 8, or 9 (Cell Technologies, Mountainview, Calif., USA), according to the manufacturer's directions and as described in Carter et al. (2005).

Cell-surface Fas expression. PPC-1 cells were seeded in suspension conditions in 24-well plates and harvested at the indicated time points. Cells were washed with binding solution (0.5% BSA in PBS), incubated with FITC-labelled anti-Fas antibody (BD Biosciences, Mississauga, ON, Canada), washed in binding solution, and analyzed by flow cytometry.

siRNA transfections. $5.0\times10^6$ cells were seeded in 100 mm dishes and transfected the next day using Lipofectamine 2000 (Invitrogen, Carlsbad, Calif., USA) and double-stranded siRNAs targeting either FLIP (siFLIP) or luciferase control sequences (siCtrl) (Dharmacon, Lafayette, Colo., USA). Cells were reseeded 6 hours post-transfection into 24-well plates at $5.0\times10^4$ cells/well, in either adherent or suspension conditions for 24-30 hours, and then assayed for apoptosis or colony formation.

DNA transfections. $5.0\times10^6$ cells were seeded in 100 mm plates. The next day the cells were transfected with 1 µg pEGFP-C1 (Clontech Laboratories) and 4 µg of plasmid expressing either FLIP, CrmA, Bcl-XL, or vector, using Lipofectamine Plus (Invitrogen) according to the manufacturer's instructions. Cells were reseeded 24-30 hours post-transfection into 24-well plates at $2.0\times10^4$ cells/well, in either adherent or suspension conditions in the presence or absence of 5809354 or staurosporine for 30 hours, and then assayed for nuclear fragmentation as described above. The percentage of EGFP-positive cells with intact or fragmented nuclei was recorded from at least 6 independent fields.

Reverse-transcriptase real-time PCR. First-strand cDNA was synthesized from 1 µg of DNase-treated total cellular RNA using random primers and SuperScript II reverse transcriptase (Invitrogen) according to the manufacturer's protocols. Real-time PCR assays were performed in triplicate with 100 ng of RNA equivalent cDNA, SYBR Green PCR Master mix (Applied Biosystems, Foster City, Calif., USA), and 400 nM of gene-specific primers. Reactions were processed and analyzed on an ABI 7700 Sequence Detection System (Applied Biosystems). Forward/reverse PCR primer pairs for human cDNAs were as follows: FasL (5'-GCA GCC CTT CAA TTA CCC AT-3'; SEQ ID NO:5/5'-CAG AGG TTG GAC AGG GAA GAA-3'; SEQ ID NO:6); FLIP-L (5'-CCT AGG AAT CTG CCT GAT AAT CGA-3'; SEQ ID NO:7/5'-TGG ATA ACC TGC TAC GAG TG-3'; SEQ ID NO:8); FLIP-S 5'-GCA GCA ATC CAA AAG AGT CTC A-3'; SEQ ID NO:9/5'-TTT TCC AAG AAT TTT CAG ATC AGG A-3'; SEQ ID NO:10); 18S (5'-GGACATCTAAGGGCATCACA-3'; SEQ ID NO:11/5'-AGGAATTGACGGAAGGGCAC-3'; SEQ ID NO:12). Relative mRNA expression was determined using the $\Delta\Delta CT$ method described in Schimmer et al. (2006).

Immunoblot analysis. Cells were lysed with sample buffer (62.5 mM Tris-HCl (pH 7.4), 2% SDS, 10% glycerol, and 5% 2-mercaptoethanol) or lysis buffer (10 mM Tris (pH 7.4), 150 mM NaCl, 0.1% Triton X-100, 0.5% sodium deoxycholate, and 5 mM EDTA) containing the complete protease inhibitor set (Roche, Indianapolis, Ind., USA). Immunoblot assays were performed as in Carter et al., (2005). Briefly, protein lysates were quantified (Protein Assay Dye Reagent or Dc Protein Assay, Bio-Rad, Mississauga, ON, Canada), resolved by electrophoresis through 10% SDS-polyacrylamide gels (SDS-PAGE), and transferred to PVDF membranes. Membranes were incubated with mouse monoclonal anti-human FLIP (clone NF6, 1:500 v/v dilution, Alexis, San Diego, Calif., USA), anti-human caspase 8 (clone 3-1-9, 1:1,000 v/v dilution, BD Biosciences), or antihuman actin (clone AC-15, 1:30,000 v/v dilution, Sigma-Aldrich). Primary antibodies were detected with horseradish peroxidase-conjugated secondary antibodies (goat anti-mouse IgG, Bio-Rad) and enhanced chemiluminescence (West Pico Reagent, Pierce, Rockford, Ill.).

In vivo studies. Male severe combined immunodeficient (SCID) mice between 5 and 7 weeks of age were obtained from an in-house breeding program. Mice were housed in laminar-flow cage racks under standardized environmental conditions. Mice had access to food and water ad libitum. All experiments were performed according to the regulations of the Canadian Council on Animal Care. To test anoikis resistance in vivo, dsRED-PPC-1 cells, which stably express dsRed fluorescent protein, were treated in culture with 5809354 (30 µM) or buffer control (16 hours), or FLIP siRNA (25 nM) or control siRNA (25 nM) (8 hours). $3.5\times10^6$ viable cells (as measured by trypan blue exclusion assay) were either injected via the tail vein or subcutaneously into the hind limbs into sublethally irradiated (3.5 Gy) SCID mice (10 mice per treatment). The number of cells injected was at least 3-fold above the minimum threshold required for distal tumor formation. Mice injected with tumor cells subcutaneously were maintained for 3 weeks and then sacrificed via carbon dioxide inhalation. Tumors were excised and weighed. Mice injected with tumor cells intravenously were maintained for 5 weeks after injection or until moribund, at which time, the animals were sacrificed via carbon dioxide inhalation and dissected. Red fluorescent tumors were detected via whole body imaging and whole organ imaging using a Leica MZ FLIII fluorescent stereomicroscope with a 100 W mercury lamp, a 560/40 excitation filter, and a 610 long-pass emission filter. Images were acquired using a Leica DC350 digital camera at 0.8× magnification and analyzed using Image Pro Plus 6.0

(MediaCybernetics). A single common threshold was applied to identify and measure fluorescence in each organ (Cairns et al., 2004). The number of fluorescent spots and the corresponding pixel area were recorded for each lung lobe. All quantification was performed on unmanipulated images.

Statistics. Data points represent the mean±SEM of multiple independent experiments unless otherwise indicated. For in vivo studies, non-parametric methods were used to test for differences in the number of metastases. For comparisons of two groups, the Mann-Whitney rank-sum test was used.

Results

FLIP Expression Contributes to Anoikis Resistance

Figure 11A:
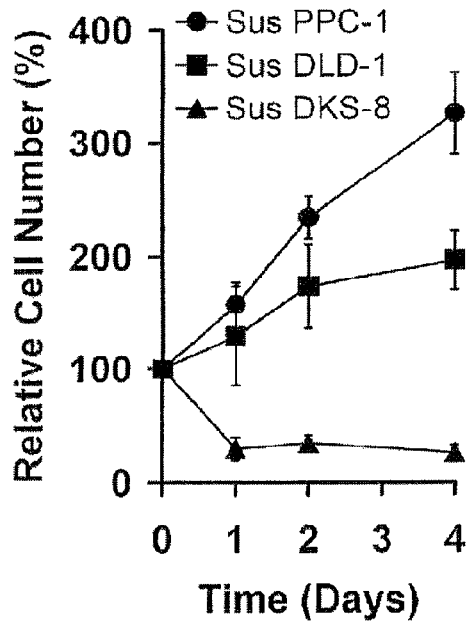
FIG. 11. PPC-1 prostate cancer cells resist anoikis despite increases in Fas and FasL expression. (A) Adherent cells ($5\times10^4$) were seeded in suspension conditions and cell growth determined by counting the number of trypan blue negative cells at increasing times after seeding. PPC-1, prostate cancer cells; DLD-1, anoikis-resistant colonic adenocarcinoma cells; DKS-8 anoikis-sensitive colonic adenocarcinoma cells. (B) PPC-1 cells were cultured under suspension conditions and cells harvested at increasing times of incubation. Anoikis was measured by flow cytometry to detect apoptotic cells stained for cell surface Annexin V expression and propidium iodide (PI) uptake. Data represents the mean±SEM percent of viable cells relative to 0 hours of suspension-culture. (C) PPC-1 cells were cultured as in panel B, stained with FITC-labeled anti-human Fas (CD95) antibody, and cell surface expression of Fas measured by flow cytometry. Data represents the mean percent±SEM of Fas expression relative to 0 hours of suspension culture. (D) PPC-1 cells were cultured as in panel B and FasL mRNA and 18S rRNA expression was measured by real-time RT-PCR. Data represents the mean±SEM percent of FasL/18S expression relative to 0 hours of suspension culture using AACr normalization. (E) FLIP levels correlate with anoikis sensitivity. PPC-1, DLD-1, and DKS-8 cells ($5\times10^6$) were grown in adherent conditions for 36 hours. Total cellular protein was isolated and analyzed by SDS-PAGE immunoblotting using antibodies for FLIP and actin. (F) Anoikis-resistant cells maintain FLIP expression after detachment. PPC-1, DLD-1, and DKS-8 cells were cultured in suspension and total cellular protein was isolated at increasing times after incubation. FLIP and actin expression were measured by SDS-PAGE immunoblotting. (G) SV40-transformed wild-type (WT) or FLIP-/−MEFs ($5\times10^5$) were cultured in suspension conditions. At increasing times after incubation, cell viability was measured by flow cytometry as described in panel B. Data were expressed as the mean±SEM percent of viable cells relative to 0 hours of suspension culture.
Figure 11B:
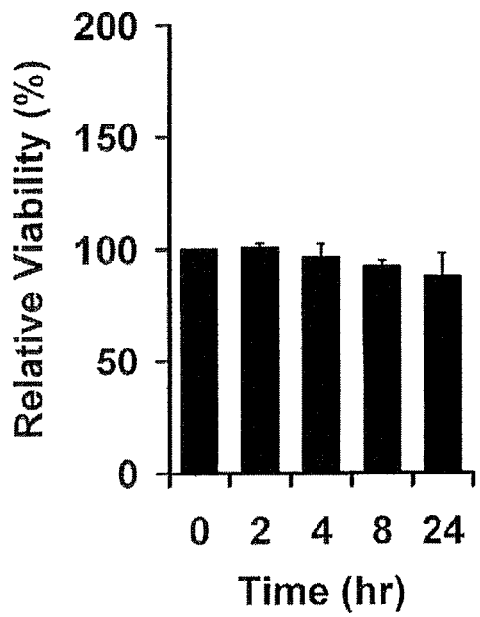

To study mechanisms of anoikis, PPC-1 prostate cancer cells were employed because they exhibit a phenotype profile similar to metastatic prostate cancer cell lines. For example, PPC-1 cells are hormone refractory (Jarrard et al., 1998), lack the tumor suppressor protein p53 (Pan et al., 2001), and are resistant to death receptor-mediated apoptosis (Schimmer et al., 2006). Included in the latter, is resistance to Fas signalling, despite cell surface expression of Fas and intracellular expression of death receptor signalling components such as FADD, TRADD, RIP, pro-caspase 8, and pro-caspase 3 (Kim et al., 2002). Because anoikis may proceed through the death-receptor pathway of caspase activation, the ability of PPC-1 cells to resist anoikis upon detachment from the ECM was tested. PPC-1 cells were cultured under suspension (detached) conditions and their growth compared to DLD-1 colon cancer cells, which are known to be resistant to anoikis, and DKS-8 colon cancer cells, which are known to be sensitive to anoikis (Rosen et al., 2000; Shirasawa et al., 1993). Robust growth of PPC-1 and DLD-1 cells in suspension with no increase in apoptosis was observed (FIGS. 11A and 11B). In contrast, DKS-8 cells underwent apoptosis within 24 hours of detachment from their extra-cellular environment.

Figure 11C:
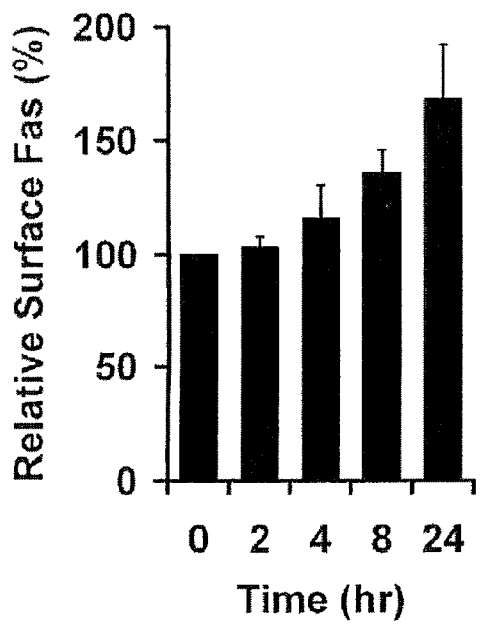
Figure 11D:
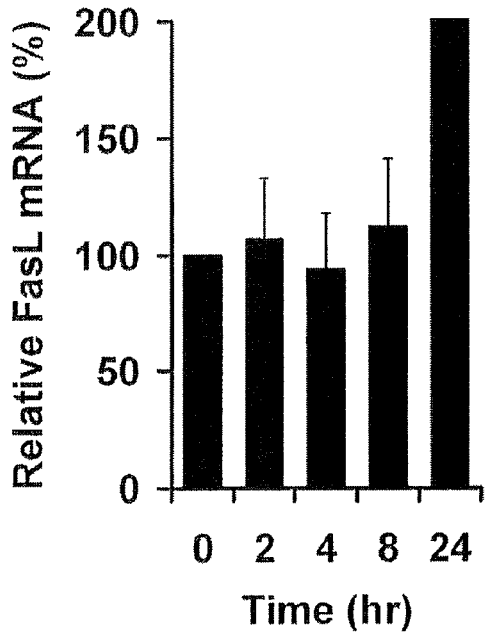

Non-malignant cells undergo anoikis mediated by up-regulation of Fas or FasL expression (Aoudjit et al., 2001; Rosen et al., 2002). To determine if PPC-1 cells were capable of initiating death-receptor signalling upon detachment, PPC-1 cells were cultured under suspension conditions and cell surface Fas and total cellular FasL expression assessed An induction of both Fas and FasL expression was observed within 24 hours of suspension culture (FIGS. 11C and 11D). Thus, these results suggest that PPC-1 cells have an intrinsic drive towards anoikis, but that apoptosis is blocked by an inhibitor of the Fas-signalled death receptor pathway.

Figure 11E:
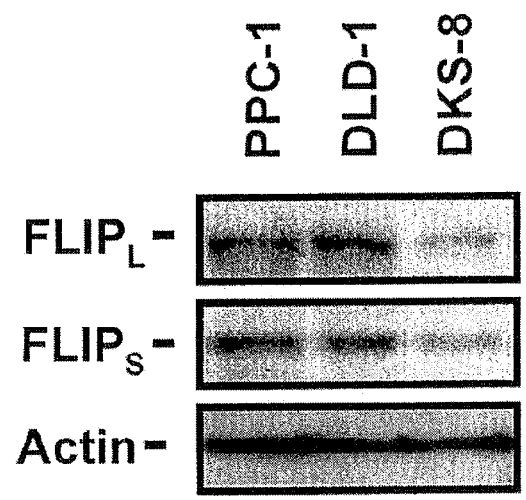
Figure 11F:
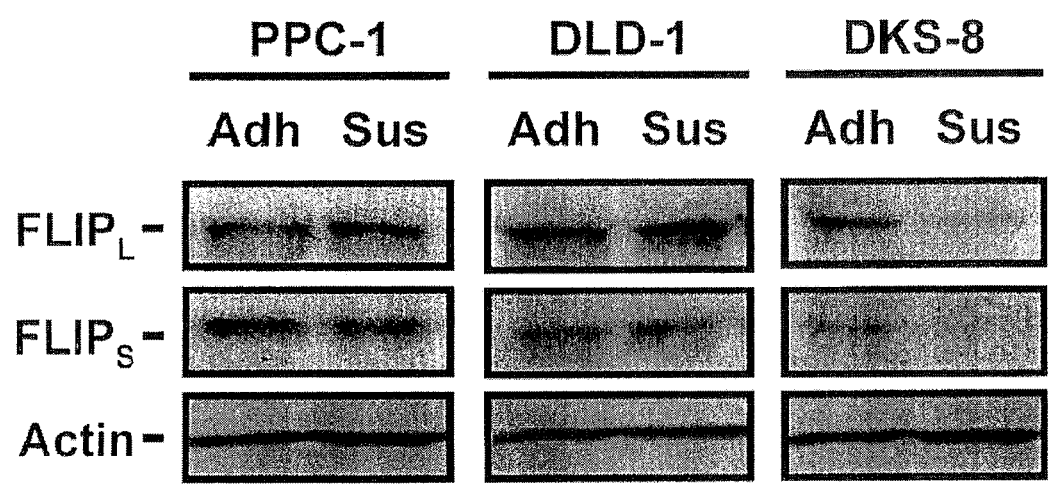
Figure 11G:
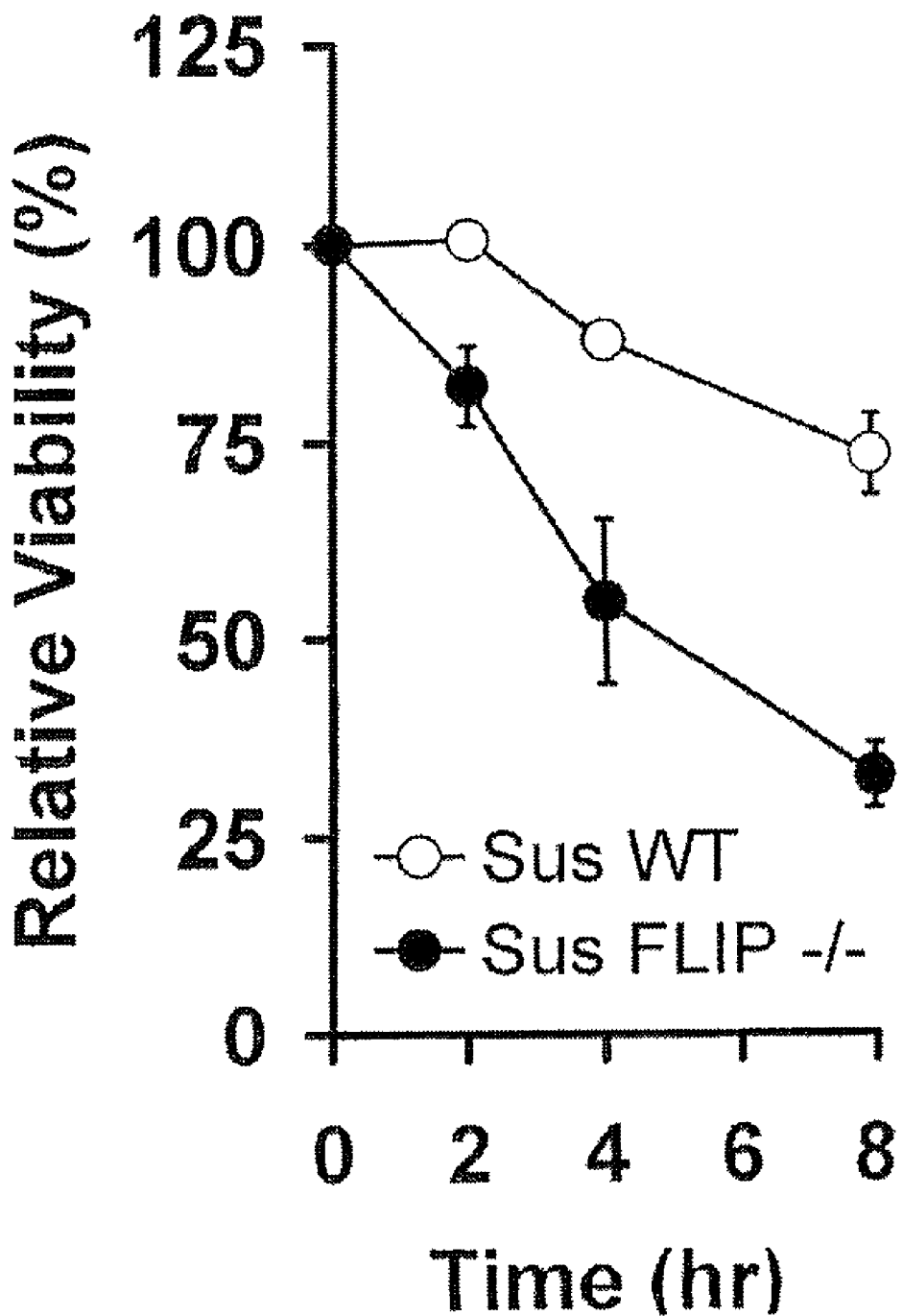

FLIP is a dominant negative inhibitor of caspase 8 signalling and its over expression renders cells resistant to the death receptor pathway of caspase activation (Krueger et al., 2001; Irmler et al., 1997; Schimmer et al., 2006; Hyer et al., 2002). FLIP is expressed as two major protein isoforms, FLIP-long ($FLIP_L$) and Flip-short ($FLIP_s$), which arise from alternate splicing of the FLIP mRNA (Scaffidi et al., 1999). Levels of FLIP in PPC-1, DLD-1, and DKS-8 cells were measured by immunoblotting. Anoikis-resistant PPC-1 and DLD-1 cells expressed higher levels of FLIP protein compared to anoikis-sensitive DKS-8 cells (FIG. 11E). Furthermore, malignant PPC-1 and DLD-1 cells maintained FLIP levels 24 hours after detachment (FIG. 11F). In contrast, anoikis-sensitive DKS-8 cells down-regulated FLIP upon detachment, similar to previously described decreases in FLIP expression in primary endothelial cells (Aoudjit et al., 2001). To further assess the contribution of FLIP to anoikis, the rate of anoikis between SV40 transformed wild-type and FLIP−/−MEFs was compared. FLIP−/−MEFs underwent anoikis more rapidly after detachment from their ECM compared to wild-type MEFs (FIG. 11G). Taken together, these results suggest that malignant cells resistant to anoikis have increased levels of FLIP upon detachment from the ECM.

Figure 12A:
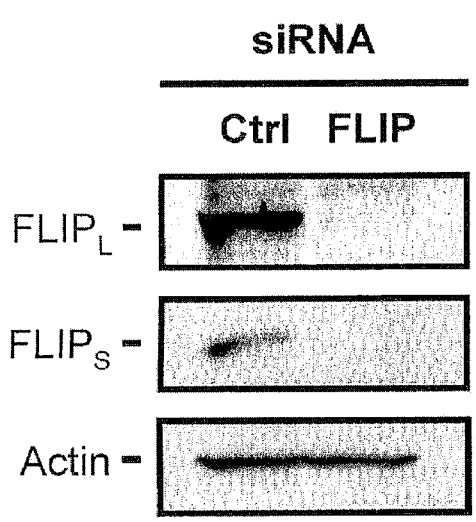
FIG. 12. Depletion of endogenous FLIP levels by siRNA sensitizes malignant cells to anoikis. (A) PPC-1 cells were seeded in adherent conditions overnight and then transfected with 25 nM anti-FLIP siRNA (siFLIP) or control luciferase siRNA (siCtrl). Thirty hours after transfection, cells were harvested, total protein isolated and analyzed by SDS-PAGE immunoblotting using anti-FLIP and anti-actin antibodies. (B) PPC-1 cells were transfected with increasing concentrations of siFLIP or siCtrl. After transfection, cells were treated with CH-11 Fas activating antibody (100 ng/ml). Thirty hours after incubation, cells were harvested and apoptosis measured by flow cytometry to detect cell surface annexin V expression and PI uptake. Data represents the mean±SEM percent of viable cells. (C) PPC-1 cells were transfected with increasing concentrations of siFLIP or siCtrl. After transfection, cells were subcultured under suspension conditions for 30 hours and then harvested. Apoptosis was measured by flow cytometry to detect cell surface annexin V expression and PI uptake. Data represents the mean±SEM of percent of viable cells. (D) Equal volumes of PPC-1 cells from panel C were replated under adherent conditions to permit clonogenic growth. One week after replating, cells were stained with methylene blue and the number of colonies counted. Data represents the mean±SEM percent of colonies compared to untreated controls.
Figure 12B:
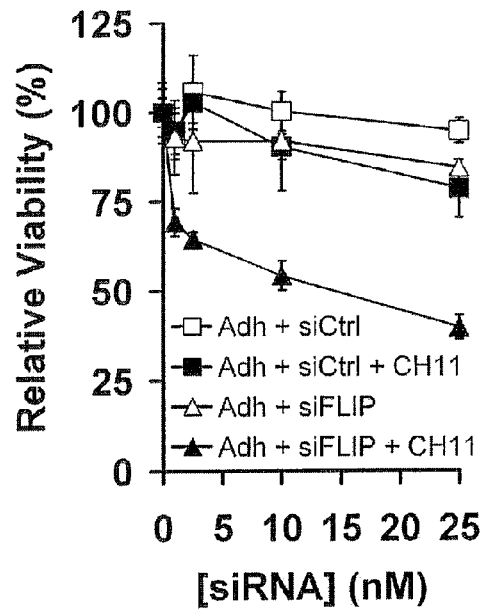
Figure 12C:
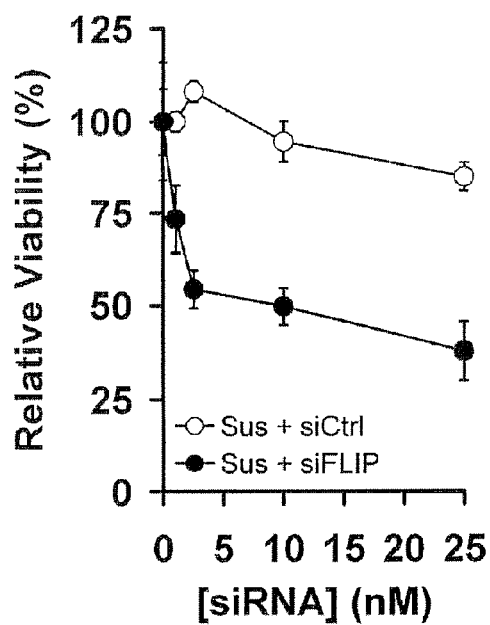
Figure 12D:
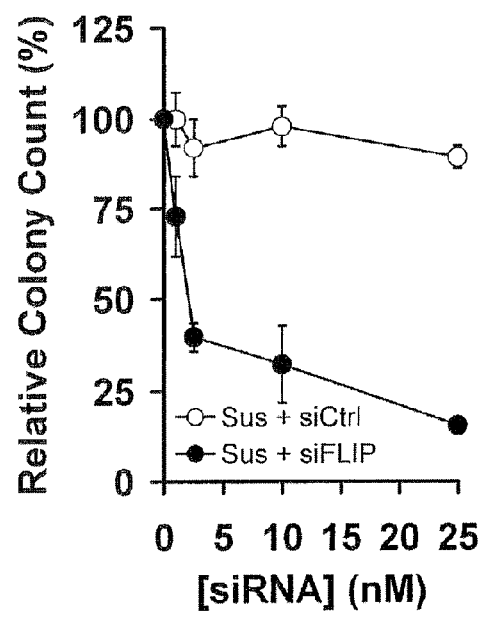
Figure 13A:
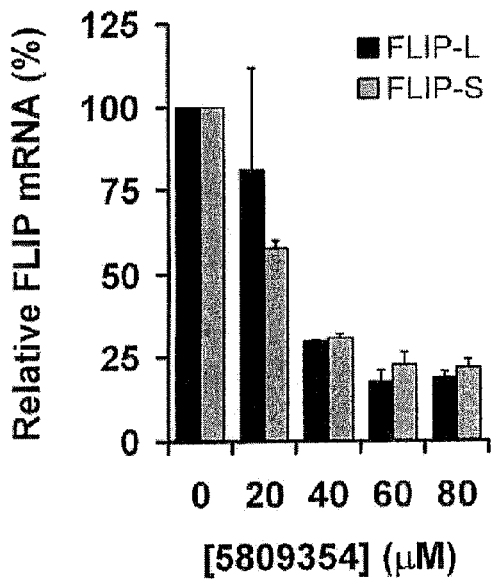
FIG. 13. Small molecule down-regulation of FLIP sensitizes prostate cancer cells to anoikis. (A) PPC-1 cells were seeded overnight in adherent conditions and then treated with increasing concentrations of 5809354 for 16 hours. After incubation, cells were harvested. Total cellular RNA was extracted and mRNA levels of the long isoform of FLIP (FLIP$_L$), the short isoform of FLIP (FLIP$_S$), or rRNA levels of 18S were detected by real-time RT-PCR. Data were normalized using the $\Delta\Delta C_T$-method and expressed as the mean±SEM percent of FasL/18S expression relative to untreated controls. (B) PPC-1 cells were cultured and treated as in panel A. Total cellular protein was isolated and analyzed by SDS-PAGE immunoblotting using anti-FLIP and anti-Actin antibodies. (C) PPC-1 cells were seeded overnight in adherent conditions and then exposed to increasing concentrations of 5809354 in the presence or absence of Fas-activating antibody (CH-11, 100 ng/mL). Thirty hours after incubation, cell viability was determined using the MTS assay. Data represents the mean±SEM of percent of viable cells. (D) PPC-1 cells were seeded overnight in adherent or suspension conditions and then treated with increasing concentrations of 5809354 for 30 hours. After incubation, apoptosis was measured by flow cytometry to detect cell surface annexin V expression and PI. Data represents the mean±SEM of percent of viable cells. (E) Cells were harvested, fixed, stained with DAPI, and nuclear morphology analyzed by fluorescence microscopy. Arrowheads refer to fragmented nuclei indicative of apoptosis. (F) PPC-1 cells ($5 \times 10^4$) were seeded in suspension conditions overnight and then cultured with increasing concentrations of 5809354 or the inactive 7271570. Thirty hours after incubation, cells were harvested and equal volumes plated in a colony formation assay. One week later, cells were stained with methylene blue and the number of colonies counted. Data represents the mean ±SEM percent of colonies relative to untreated controls.
Figure 13B:
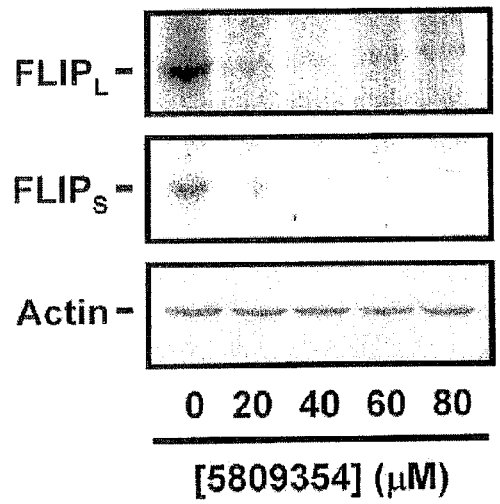
Figure 13C:
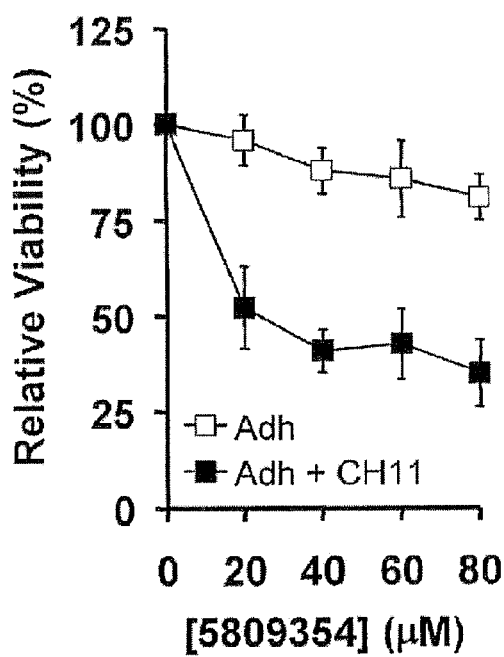
Figure 13D:
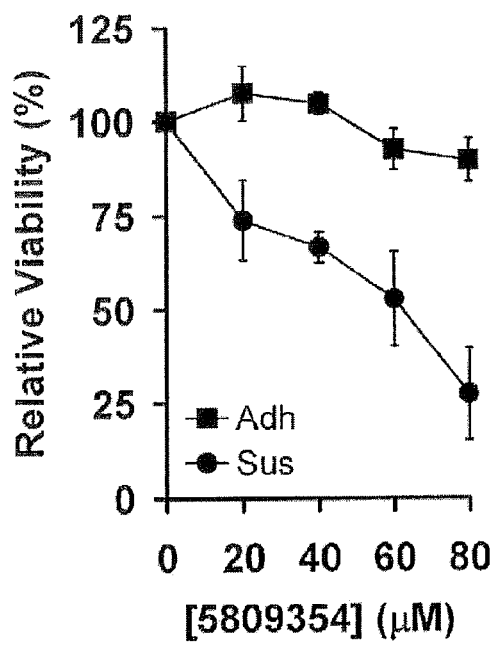
Figure 13E:
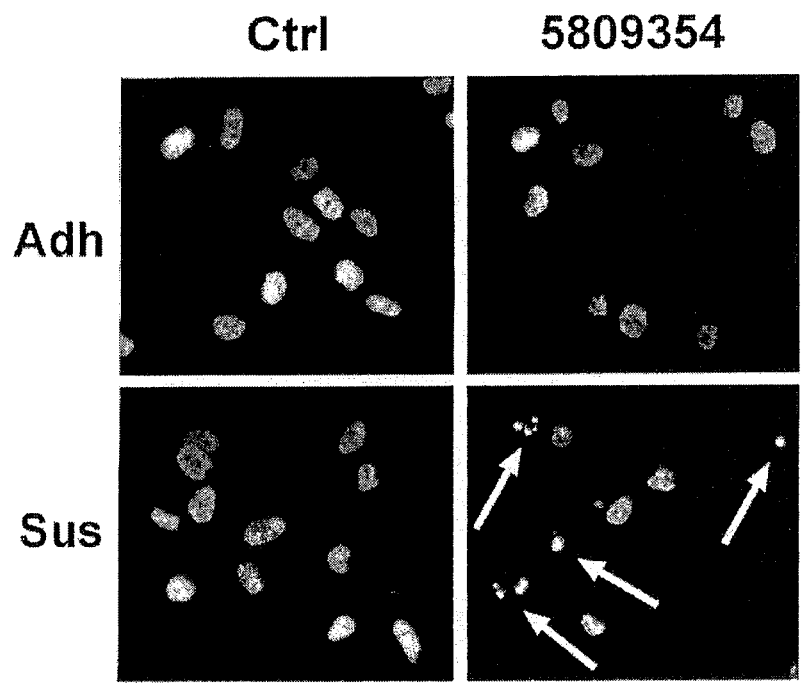
Figure 13F:
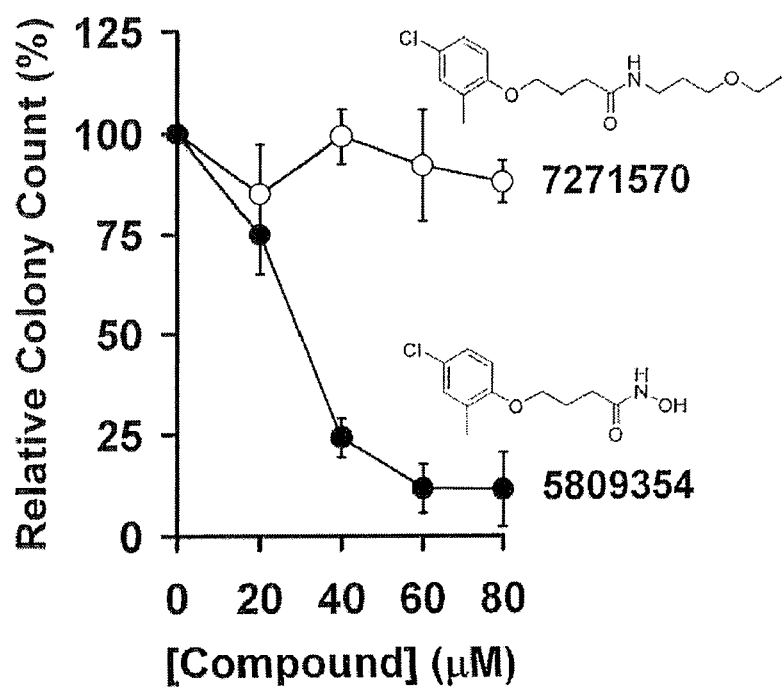

To functionally assess the role of FLIP in anoikis, RNA interference was employed to knockdown FLIP expression in PPC-1 cells. FLIP siRNA reduced the expression of both FLIP-long and FLIP-short isoforms as determined by immunoblotting (FIG. 12A), and sensitized adherent-cultured PPC-1 cells to Fas signalling by a Fas-activating antibody (CH-11, 100 ng/mL, FIG. 12B). To examine the effects of FLIP siRNA on anoikis, PPC-1 cells were transfected in adherent conditions with increasing concentrations of FLIP siRNA or control siRNA and then cultured for 30 hours under suspension conditions. FLIP siRNA but not a control siRNA, sensitized PPC-1 cells to anoikis in a concentration-dependent manner whereas control siRNA left PPC-1 cells resistant to anoikis (FIGS. 12C and 12D). Of note, under adherent conditions FLIP siRNA did not reduce cell viability up to four days after treatment (data not shown). Thus, these findings further support the role of FLIP as a suppressor of anoikis and suggest that inhibiting FLIP may be a useful strategy to sensitize malignant cells to anoikis.

Small Molecule Down-regulation of FLIP mRNA Sensitizes Cells to Anoikis

Previously, a high-throughput chemical screen was employed to identify small molecules that sensitize PPC-1 cells to Fas-mediated apoptosis (Example 1). From this screen, 4-(4-chloro-2-methylphenoxy)-N-hydroxybutanamide (5809354) was found to specifically sensitize resistant cells to Fas- and TRAIL-mediated apoptosis by decreasing FLIP expression.

5809354 was used as a tool to further evaluate the relationship between death receptor signalling, FLIP, and anoikis. PPC-1 cells exposed to increasing concentrations of 5809354 showed a concentration-dependent decrease in FLIP mRNA and protein expression (FIGS. 13A and 13B), which correlated with decreases in viability when cultured in the presence of Fas-activating antibody (CH-11, 100 ng/mL, FIG. 13C). To determine if small-molecule modulation of FLIP could sensitize cells to anoikis, PPC-1 cells were cultured under adherent or suspension (detached) conditions overnight and then incubated with 5809354 for 30 hours. Apoptosis was measured by flow cytometry to detect cell surface annexin V expression and PI staining, or by nuclear fragmentation as determined by DAPI staining. 5809354 sensitized cells to anoikis (FIGS. 13D and 13E) at concentrations associated with reductions in FLIP mRNA and protein. It is important to note that 5809354 did not induce apoptosis in PPC-1 cells cultured under adherent conditions up to five days after treatment (FIG. 13 and data not shown). In contrast to the effects of 5809354, 7271570 failed to decrease FLIP levels and also failed to sensitize cells to either CH-11 or anoikis (FIG. 3F and data not shown).

Figure 14:
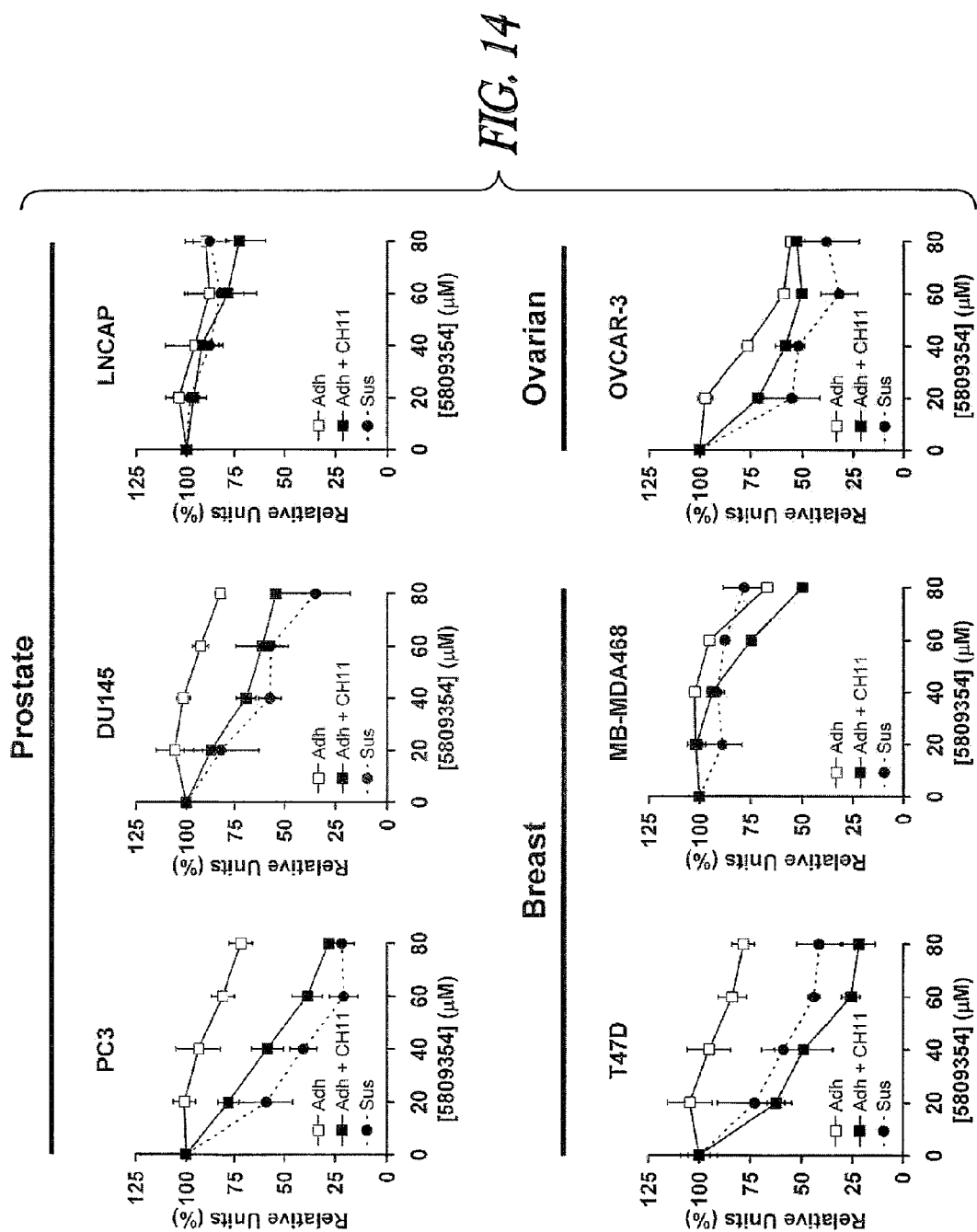
FIG. 14. Tumor cell sensitivity to anoikis correlates with sensitivity to Fas-mediated apoptosis. PC-3, DU-145, and LNCaP prostate, T47D and MB-MDA-468 breast, and OVCAR-3 ovarian cancer cells were cultured under adherent conditions with increasing concentrations of 5809354, in the presence or absence of Fas-activating antibody (CH-11, 100 ng/mL). Thirty hours after incubation, cell viability was determined using the MTS assay. Cell lines were also cultured under suspension conditions in the presence or absence of 5809354. Thirty hours after incubation, equal volumes of suspension-cultured cells were replated in a colony formation assay. Data represents the mean±SEM percent of viable cells or colonies compared to untreated controls.

To assess the spectrum of activity of 5809354 as an anoikis sensitizer, the effects of this compound were tested on 6 additional malignant cell lines (FIG. 14). 5809354 sensitized PC-3 and DU-145 prostate cancer, T47D breast, and OVCAR-3 ovarian cancer cell lines to anoikis. Likewise, 5809354 also sensitized these lines to CH-11-induced apoptosis. Conversely, 5809354 did not sensitize LNCaP or MB-MDA-468 cells to anoikis or CH-11. Thus, a strong correlation was observed between the ability of 5809354 to sensitize tumor cells to Fas-mediated apoptosis in adherent conditions, and its ability to sensitize these same cells to anoikis.

The above studies provide further evidence that anoikis and Fas-mediated apoptosis share a common pathway. Furthermore, they suggest that a small molecule that targets FLIP expression can be used to sensitize cells to anoikis.

5809354 Induces Anoikis by a Caspase 8-dependent Mechanism

Figure 15A:
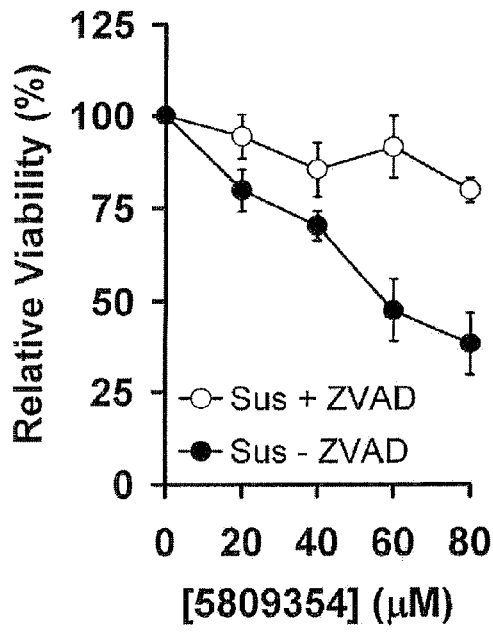
FIG. 15. 5809354 sensitizes cells to anoikis through a caspase 8 dependent mechanism. (A) PPC-1 cells ($5 \times 10^4$) were cultured under suspension conditions overnight and then treated with 5809354 in the presence or absence of the pan-caspase inhibitor z-VAD-fmk (100 µM). Thirty hours after incubation, anoikis was determined by flow cytometry to detect cell surface annexin V expression and PI uptake. Data represents the mean±SEM percent of viable cells or colonies compared to untreated controls. (B) PPC-1 cells ($5 \times 10^4$) were cultured in suspension conditions overnight and then treated with 5809354 (60 µM). At increasing times after treatment, caspase activation was detected with FITC-labeled peptides that bind preferentially and irreversibly to caspase 3/7, 8, or 9. Caspase activation was monitored by flow cytometry to quantify the percentage of fluorescently labeled cells. Data represents the mean±SEM percent caspase-active cells relative to untreated controls. (C) PPC-1 cells were seeded overnight in adherent or suspension conditions and then treated with 5809354 (60 µM). At increasing times after incubation, total cellular protein was isolated and analyzed by SDS-PAGE immunoblotting using anti-caspase 8 and anti-actin antibodies. * indicates cleaved caspase 8. (D) PPC-1 cells were seeded overnight in adherent or suspension conditions and then treated with increasing concentrations of staurosporine (STS). Thirty hours after incubation, apoptosis was measured by cell surface annexin V expression and PI uptake. Data represents the mean±SEM percent of viable cells compared to untreated controls. (E) E1A-transformed wild-type (WT) and caspase 8−/−MEFs were cultured in suspension conditions with increasing concentrations of 5809354. Ten hours after incubation, cell viability was measured using the MTS assay. Data represents the mean±SEM percent viable cells compared to untreated controls. (F) PPC-1 cells were co-transfected with plasmids expressing FLIP, CrmA, BclXL, or empty vector, along with a plasmid expressing EGFP (to identify successfully-transfected cells). After 24 hours, cells were reseeded in suspension conditions, cultured overnight, and then treated with vehicle, 5809354 (60 µM), or staurosporine (0.5 µM). Thirty hours after incubation, cells were harvested, fixed, and stained with DAPI. EGFP expression and nuclear morphology were analyzed by fluorescence microscopy. EGFP-expressing cells were scored for intact or fragmented nuclei, and the percentage of apoptotic cells calculated. Data from a representative experiment is shown.
Figure 15B:
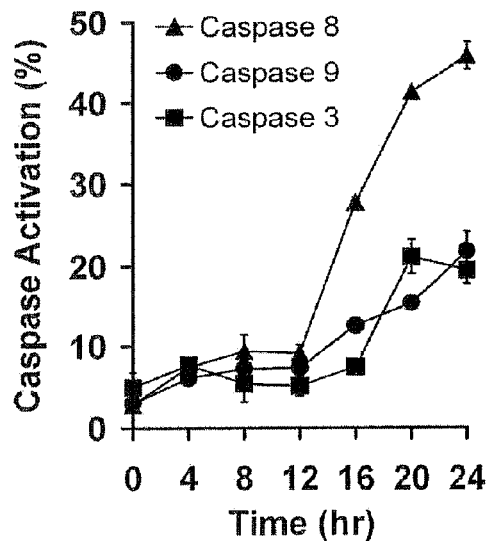
Figure 15C:
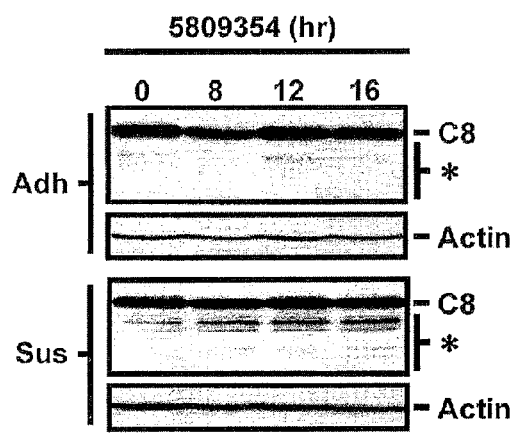
Figure 15D:
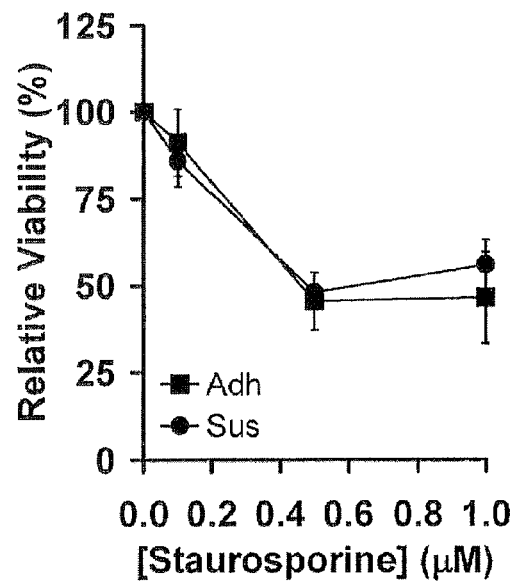

Next, the mechanism by which reductions in FLIP by 5809354 promotes anoikis was investigated. PPC-1 cells were cultured under suspension conditions with increasing concentrations of 5809354 and the pan-caspase inhibitor z-VAD-fmk. z-VAD-fmk inhibited the ability of 5809354 to promote anoikis, demonstrating a caspase-dependent mechanism of anoikis (FIG. 15A). To determine the sequence of caspase activation in 5809354-mediated anoikis, PPC-1 cells were treated with 5809354 (60 µM) or buffer under suspension conditions. At increasing times after treatment, caspase activation was detected using cell-permeable FITC-labelled peptides that bind preferentially and irreversibly to active caspases. Active caspase 8 was detected prior to activation of caspases 3/7 and 9 (FIG. 15B). These data suggest that 5809354 can sensitize cells to anoikis by activating the death receptor pathway of caspase activation. Consistent with this observation, immunoblot analysis revealed that 5809354 preferentially activated caspase 8 in cells cultured under suspension but not adherent conditions (FIG. 15C). In contrast to 5809354, staurosporine, an activator of the intrinsic/mitochondrial apoptotic pathway, induced apoptosis in a manner that did not discriminate between suspension and adherent cells (FIG. 15D). Therefore, these data suggest that FLIP down-regulation derepresses a caspase 8-dependent pathway of anoikis.

Figure 15E:
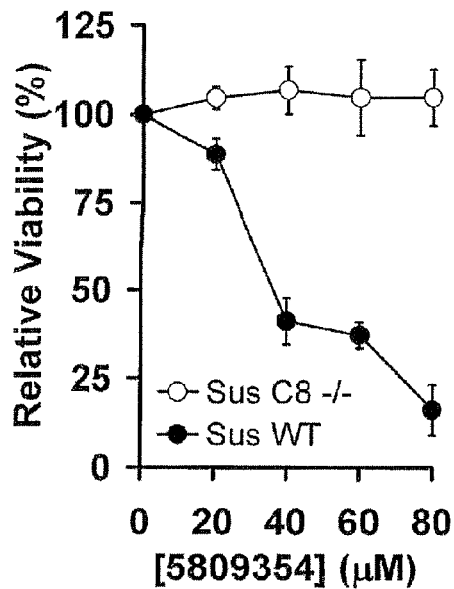
Figure 15F:
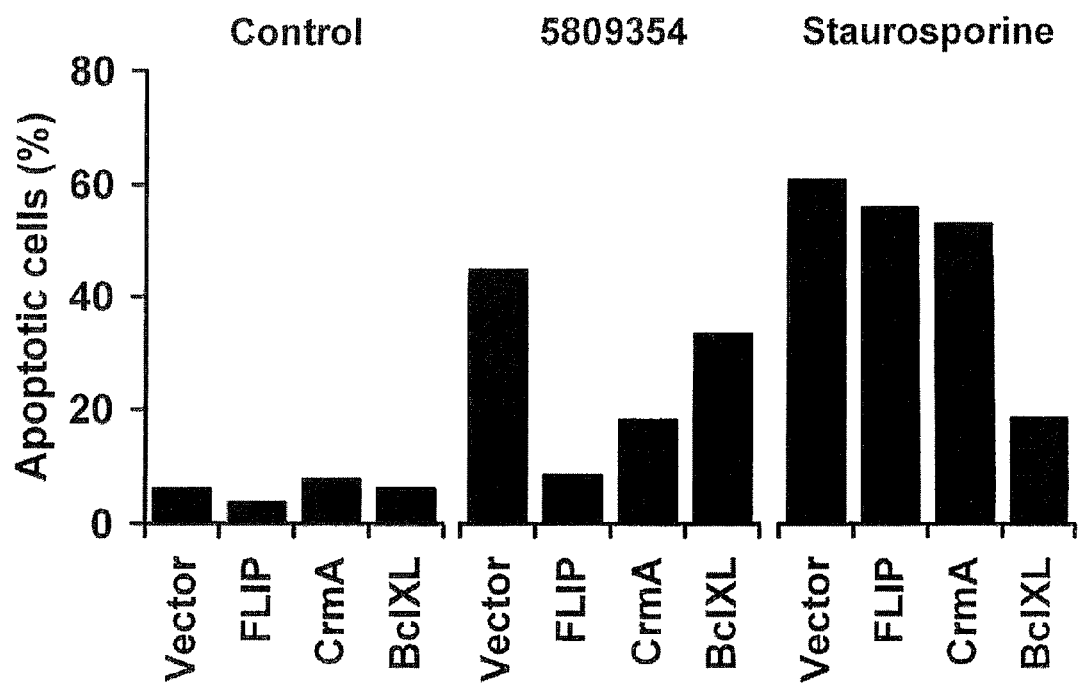

To further evaluate the relationship between FLIP and caspase 8 in anoikis, the effects of 5809354 were studied in two independent models of caspase 8 inhibition. First, caspase 8-deficient E1A-transformed MEFs were found to be resistant to 5809354-mediated anoikis compared to wild-type E1A transformed MEFs (FIG. 15E). Second, overexpression of FLIP or the viral caspase 8 inhibitor CrmA, but not the mitochondrial anti-apoptotic protein BclXL or empty vector, attenuated 5809354-mediated anoikis (FIG. 15F). In contrast, overexpression of BclXL, but not CrmA, protected PPC-1 cells from staurosporine-induced anoikis. These results provide further evidence that decreases in FLIP expression initiates a caspase 8-dependent pathway of anoikis.

Figure 16A:
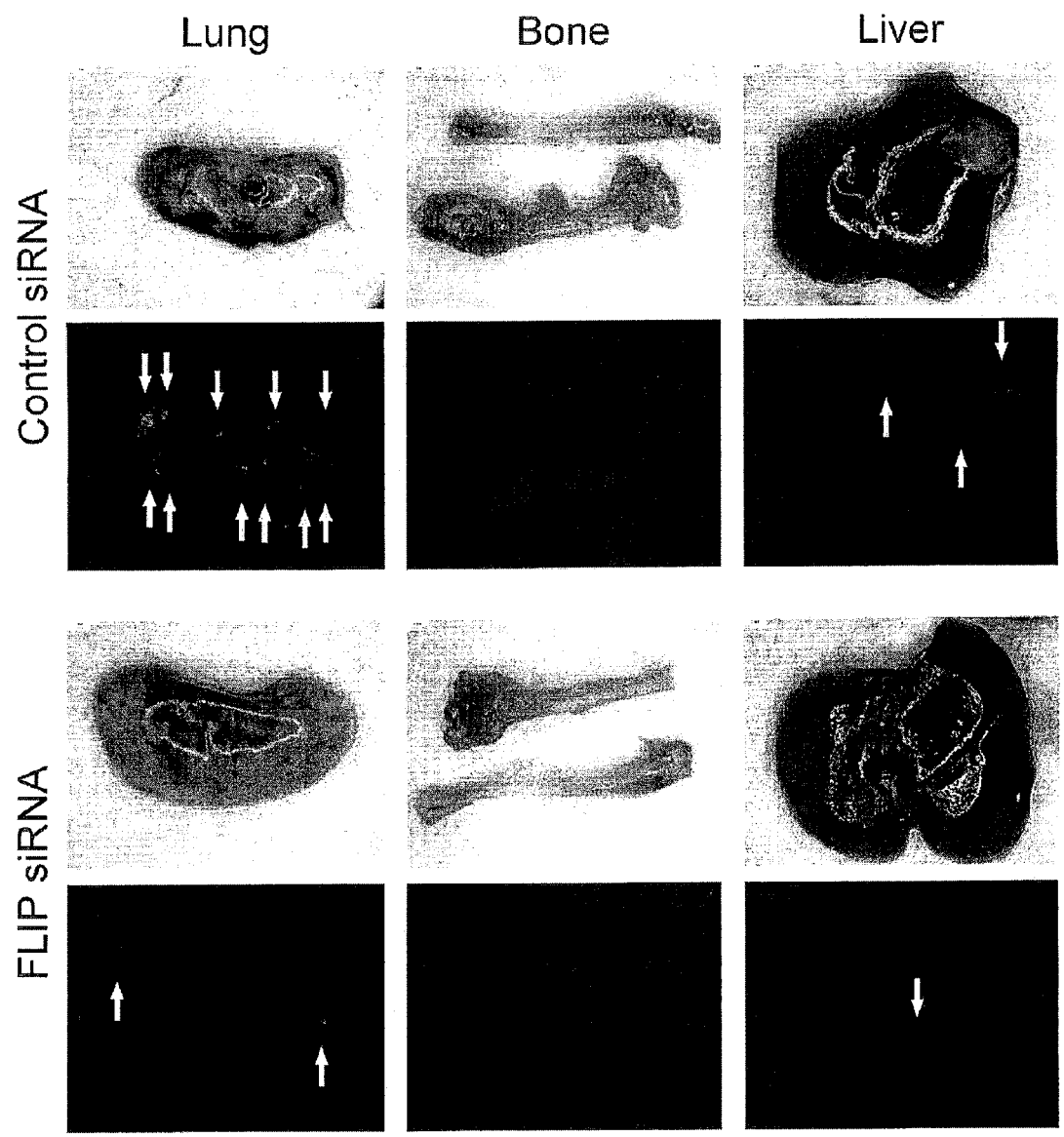
FIG. 16. Decreases in cellular FLIP levels by siRNA diminishes the in vivo survival and growth of circulating prostate cancer cells. (A) Fluorescent dsRed-PPC-1 cells were transfected in culture with anti-FLIP siRNA (siFLIP, 25 nM) or control siRNA (siCtrl, 25 nM). Eight hours after transfection cells were harvested and $3.5 \times 10^6$ viable cells were injected into the tail veins of sublethally irradiated SCID mice. Five weeks after injection, or when mice became moribund, mice were sacrificed and their organs imaged using a fluorescent microscope (n=9). Representative images of tumor formation in the lung, bone, and liver are shown. (B) The total number and area of distant tumors from mice described above were quantified using image analysis software. Tumors were quantified from all five lobes of the lungs. Data points represent measurements from each mouse. Differences in the number and area of tumors are significant by the rank sum test. The bar represents the median of the population. Measurements were completed on unaltered images.
Figure 16B:
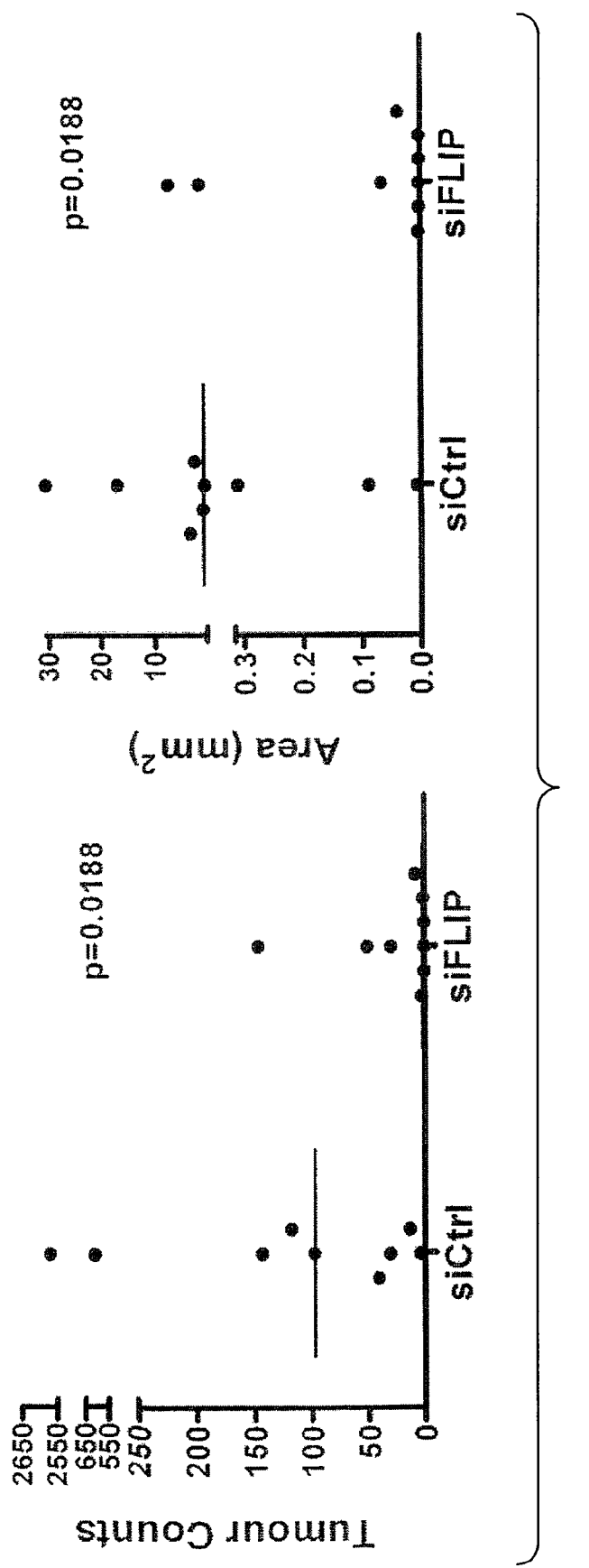
Figure 17A:
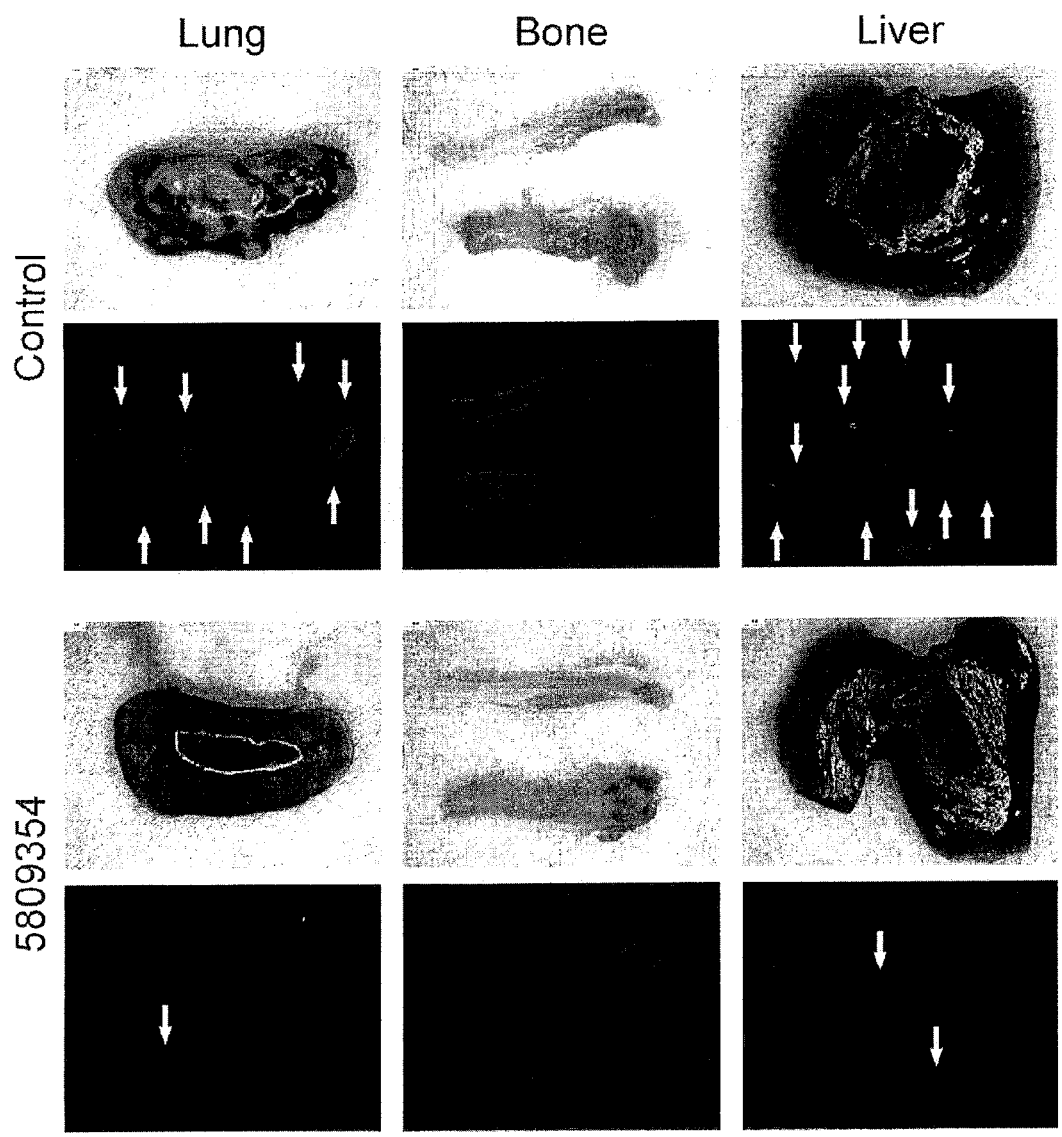
FIG. 17. Decreases in cellular FLIP levels by 5809354 diminishes the in vivo survival and growth of circulating prostate cancer cells. (A) Fluorescent dsRed-PPC-1 cells were treated in culture with 5809354 (30 µM) or buffer control. Sixteen hours after treatment cells were harvested and $3.5 \times 10^6$ viable cells were injected into the tail veins of sublethally irradiated SCID mice. Five weeks after injection, or when mice became moribund, mice were sacrificed and their organs imaged using a fluorescent microscope (n=8). Representative images of tumor formation in the lung, bone, and liver are shown. (B) The number and area of distant tumors from mice described above were quantified using image analysis software. Tumors were quantified from all five lobes of the lungs. Data points represent measurements from each mouse. Differences in the number and area of tumors are significant by the rank sum test. The bar represents the median of the population. Measurements were made on unaltered images.
Figure 17B:
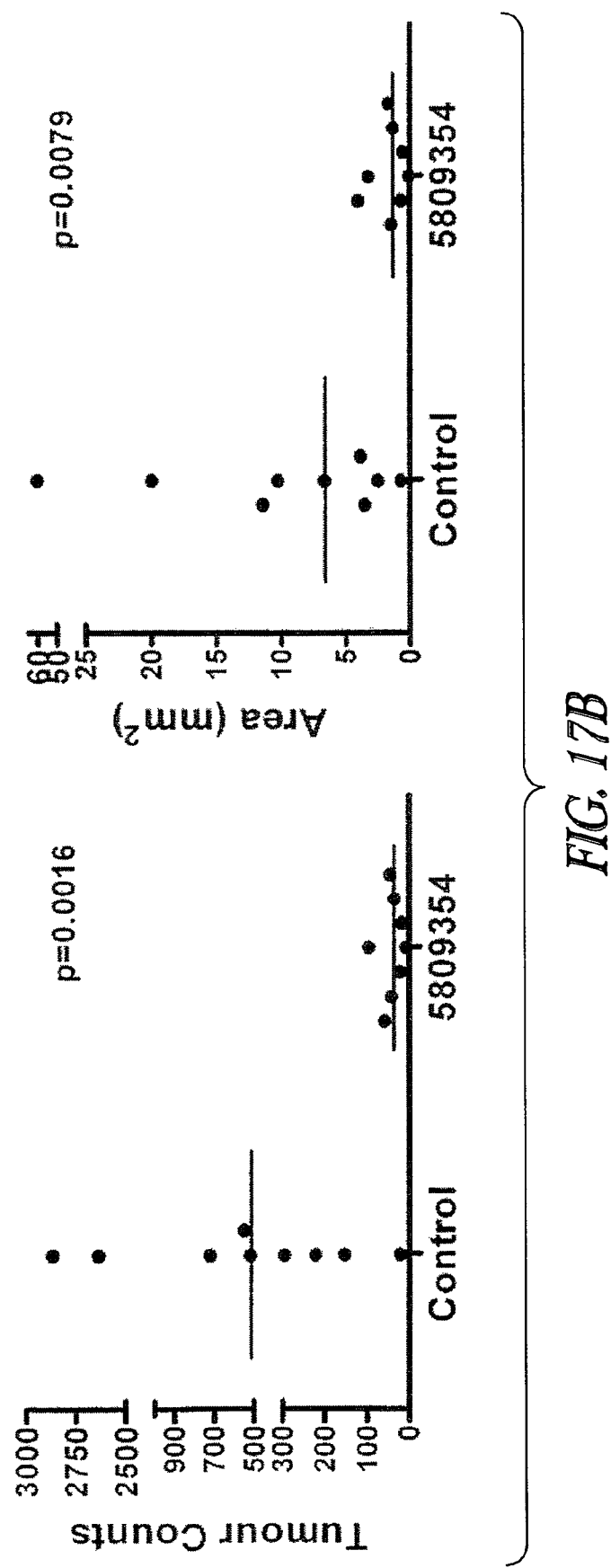

Genetic and Chemical Down Regulation of FLIP Decreases the in vivo Survival of Circulating Prostate Cancer Cells The abundance and phenotype of circulating cancer cells can influence metastasis and survival (Cristofanilli et al., 2004; Berezovskaya et al., 2005; Moreno et al., 2005). Anoikis serves as a barrier to metastasis as it prevents normally adherent cells from surviving in an anchorage-independent fashion in vivo. FLIP expression contributes to anoikis resistance in vitro, so it was tested whether reductions in cellular FLIP levels could decrease the in vivo survival of circulating prostate cancer cells and thereby decrease the formation of distal tumor formation. dsRed-labelled PPC-1 cells were treated with FLIP siRNA (25 nM), control siRNA (25 nM), 5809354 (30 µM), or buffer control in culture under adherent conditions. After treatment, cells were injected intravenously into sublethally irradiated SCID mice. Five weeks after IV injection or when moribund, mice were sacrificed and tumor formation in the organs was imaged with fluorescent microscopy. Invasion of prostate cancer cells was detected in the lung, bone, and liver, clinically relevant sites of metastases in prostate cancer. Treatment with either FLIP siRNA or 5809354 decreased tumor formation in these organs compared to controls (FIGS. 16 and 17). It is important to note that both treated and control cells were greater than 85% viable at the time of injection and remained viable for an extended period under adherent conditions.

Metastasis of dsRed-PPC-1 cells to the lung was readily quantifiable using image-based analysis (Cairns et al., 2004; Hoffman, 2005). Compared to control siRNA, mice injected with FLIP siRNA treated cells had decreased median tumor number and median total tumor area. Likewise, compared to buffer control, mice injected with 5809354 treated cells had a decreased median total tumor count median total tumor area within the lung (FIGS. 16 and 17). Median survival was not significantly different between mice injected with FLIP siRNA or control siRNA treated cells (33 days versus 26.5 days respectively, p=0.0993, n=9). Median survival of mice injected with 5809354 treated cells was significantly longer than mice injected with control treated cells (32 days versus 20 days respectively, p=0.0002, n=8). Similar reductions in tumor growth were observed in the bones and liver. In contrast to the decrease in tumor formation after intravenous injection, no difference in tumor weight was detected after subcutaneous injection of dsRed-PPC-1 cells treated with 5809354 or buffer alone (data not shown). These results validate that the PPC-1 cells were viable at the time of injection.

Taken together, these results indicate that inhibiting FLIP with small molecules or siRNA decrease the survival of circulating tumor cells and thereby decrease tumor formation in distant organs. Thus, the inhibition of FLIP may be a useful anti-metastatic strategy.

Discussion

Anoikis serves as a barrier to metastasis. Resistance to anoikis permits cancer cells to survive in the systemic circulation and facilitates their metastasis to distant organs. In fact, patients with circulating tumor cells in the peripheral blood after conventional chemotherapy have a worse prognosis compared to patients without these circulating cells (Cristofanilli et al., 2004; Moreno et al., 2005). Therefore, therapeutic strategies that specifically target anoikis-resistance pathways have the potential to decrease metastasis and thereby improve patient survival.

Recent studies in non-malignant epithelial cells have shown that anoikis is a self-initiating event that occurs, in part, by activation of the death receptor pathway of apoptosis (Frisch et al., 2001; Aoudjit et al., 2001; Rosen et al., 2002; Rytomaa et al., 1999; Frisch, 1999). In contrast, malignant epithelial cells resist anoikis and survive in an anchorage-independent manner (Glinsky et al., 1997; Zhu et al., 2001; Nishimura et al., 2001).

PPC-1 prostate cancer cells were demonstrated to be remarkably resistant to anoikis despite the increased expression of the death receptor Fas and its ligand FasL. In both PPC-1 and DLD-1 cells, a correlation was noted between resistance to anoikis and persistent expression of the caspase 8 inhibitor FLIP after detachment. In contrast, DKS-8 colonic epithelial cells rapidly underwent anoikis and showed detachment-induced decreases in FLIP expression. Similar decreases in FLIP expression have been previously reported for anoikis-sensitive primary endothelial cells (Aoudjit et al., 2001). Sensitization to anoikis was also observed in MEFs and PPC-1 cells lacking FLIP expression. From these studies, it was concluded that persistent FLIP expression in malignant cells upon detachment from the ECM renders cells resistant to anoikis.

To further explore the role of FLIP and Fas-signalling in anoikis, 5809354, a molecule that sensitizes cells to Fas-mediated apoptosis, was employed. 5809354 decreased FLIP mRNA and protein expression and thereby sensitized malignant cells to anoikis. Of note, FLIP siRNA or 5809354 did not induce apoptosis in adherent cells even after prolonged culture. Together, these observations support the hypothesis that anoikis can be initiated via activation of the Fas-signalling pathway. Furthermore, the present data is the first to show that malignant epithelial cells can be sensitized to anoikis upon down-regulation of FLIP.

The downstream mechanisms by which decreases in FLIP sensitized cells to anoikis was also investigated. Using multiple independent methods, FLIP down-regulation by 5809354 was found to initiate anoikis via a caspase 8-dependent mechanism. Importantly, caspase 8 activation was observed preferentially in suspension-cultured PPC-1 cells and not in adherent-cultured cells, a finding consistent with the observation that PPC-1-cells induce Fas and FasL expression upon detachment. In nonmalignant cells, caspase 8 plays a pivotal role in the initiation of anoikis (Aoudjit et al., 2001; Rosen et al., 2002; Rytomaa et al., 1999; Frisch, 1999). Similarly, a recent study found that adenovirus-mediated over expression of caspase sensitized gastric carcinoma cells to anoikis and also prevented their peritoneal dissemination from the abdominal cavity (Nishimura et al., 2001). In contrast, p53 over expression did not sensitize these cells to anoikis. Taken together, the present data suggest that FLIP suppresses anoikis in malignant cells by inhibiting detachment-induced caspase 8 activation.

Previous studies measuring FLIP expression suggest that this protein may be an important determinant of the metastatic potential of a cell. For example, reviewing data from gene profiling studies, FLIP mRNA expression was found to be higher in metastatic prostate tumors compared to benign prostate tissues (Varambally et al., 2005; Lapointe et al., 2004; Yu et al., 2004). Likewise, increased levels of FLIP protein were found in metastatic prostate tumors compared to localized disease by immunoblotting and immunohistochemistry (Shimada et al., 2006). The increase in FLIP in metastatic prostate tumors compared to localized prostate cancer may explain why metastatic tumors retain malignant potential even though they show increases in FasL expression relative to localized tumors. Reviewing data from gene expression profiling from other tumor sites also revealed that FLIP over-expression was associated with an increased mortality in patients with prostate, breast, and lung cancer (Varambally et al., 2005; Yu et al., 2004; van't Veer et al., 2002; Bhattacharjee et al., 2001). Thus, these results suggest that FLIP is a potential target for novel anti-cancer therapies.

Both animal and clinical studies have shown that the presence and phenotype of malignant cells in the circulation can predict metastasis and survival (Berezovskaya et al., 2005; Moreno et al., 2005). To study the contribution of FLIP expression to anoikis-resistance in vivo, a mouse model was employed that measures the ability circulating human prostate cancer cells to form distant tumors. Functional genetic and chemical genetic down-regulation of FLIP was found to reduce the number and area of distant tumors. In this model, FLIP levels were decreased in adherent dsRed PPC-1 cells in culture prior to injection into mice. It is important to note that the cells were viable at the time of injection and remained viable when cultured under adherent conditions for extended periods of time. Furthermore, note that no difference was detected in tumor growth after subcutaneous injection of cells treated with 5809354 or control, indicating the specific effects of FLIP inhibition on anoikis in vivo.

The present study supports the hypothesis that the death receptor (extrinsic) pathway of apoptosis can initiate anoikis (Frisch et al., 2001), however, other studies have shown that anoikis involves activation of the mitochondrial (intrinsic) pathway of apoptosis (Rosen et al., 2000; Grossmann et al., 2001; Rosen et al., 2001). These apparently opposing concepts can be reconciled by studies showing that death receptor-initiated anoikis can still occur even though blocks in the mitochondrial pathway are present (Rosen et al., 2002). Furthermore, in some cells, apoptosis initiated through the death receptor pathway requires amplification through the mitochondrial pathway of caspase activation (Slee et al., 1999; Kuwana et al., 1998). In these cases, blocks in the mitochondrial pathway can inhibit anoikis (Rytomaa et al., 1999; Jiang et al., 2001). Further studies are needed to assess the relative contribution of these pathways to anoikis. However, it is tempting to speculate that epithelial cells may acquire differential blocks in pro-anoikis pathways depending on the tissues from which they metastasize. Consistent with this concept, recent transciptome and proteome-wide studies on metastatic cells suggest that specific metastatic signatures may exist for cells based on their source and target organ (Varambally et al., 2005; Minn et al., 2005). Future studies that identify pro-metastatic genes may also identify novel suppressors of anoikis.

In summary, the present data suggest that the overexpression of FLIP in malignant cells suppresses anoikis and contributes to their metastatic potential. Thus, inhibiting FLIP expression may be a useful strategy in the treatment of metastatic malignancy.

REFERENCES

Aoudjit et al., Matrix attachment regulates Fas-induced apoptosis in endothelial cells: a role for c-flip and implications for anoikis. *J Cell Biol* 2001;152(3):633-43.

Bachelder et al., The cleavage of Akt/protein kinase B by death receptor signalling is an important event in detachment-induced apoptosis. *J Biol Chem* 2001;276(37):34702-7.

Berezovskaya et al., Increased expression of apoptosis inhibitor protein XIAP contributes to anoikis resistance of circulating human prostate cancer metastasis precursor cells. *Cancer Res* 2005;65(6):2378-86.

Bhattachajee et al., Classification of human lung carcinomas by mRNA expression profiling reveals distinct adenocarcinoma subclasses. *Proc Natl Acad Sci USA* 2001;98(24):13790-5.

Boatright et al., Mechanisms of caspase activation. *Curr Opin Cell Biol* 2003;15(6):725-31.

Boise et al., Bcl-x, a Bcl-2-related gene that functions as a dominant regulator of apoptotic cell death. *Cell* 1993;74:597-608.

Bradford, A rapid and sensitive for the quantitation of microgram quantities of protein utilizing the principle of protein-dye binding. *Analy. Biochem.* 1976;72:248-54.

Cairns et al., Acute hypoxia enhances spontaneous lymph node metastasis in an orthotopic murine model of human cervical carcinoma. *Cancer Res* 2004;64(6):2054-61.

Carter et al., Small-molecule XIAP inhibitors derepress downstream effector caspases and induce apoptosis of acute myeloid leukemia cells. *Blood* 2005;105(10):4043-50.

Carter et al., Small-molecule XIAP inhibitors derepress downstream effector caspases and induce apoptosis of acute myeloid leukemia cells. *Blood* 2005;105:4043-50.

Chinnaiyan et al., FADD, a novel death domain-containing protein, interacts with the death domain of Fas and initiates apoptosis. *Cell* 1995;81(4):505-12.

Chou, The Median-Effect Principle and the Combination Index for Quantitation of Synergism and Antagonism. In: D. C. Rideout and T. C. Chou (eds.), Synergism and Antagonism in Chemotherapy, pp. 61-102: Academic Press, Inc., 1991.

Cristofanilli et al., Circulating tumor cells, disease progression, and survival in metastatic breast cancer. *N Engl J Med* 2004;351(8):781-91.

DeMarzo et al., Pathological and molecular aspects of prostate cancer. *Lancet* 2003;361(9361):955-64.

Frisch et al., Anoikis mechanisms. *Curr Opin Cell Biol* 2001;13(5):555-62.

Frisch et al., Disruption of epithelial cell-matrix interactions induces apoptosis. *J Cell Biol* 1994;124(4):619-26.

Frisch, Evidence for a function of death-receptor-related, death-domain-containing proteins in anoikis. *Curr Biol* 1999; 9(18):1047-9.

Glinsky et al., Apoptosis and metastasis: increased apoptosis resistance of metastatic cancer cells is associated with the profound deficiency of apoptosis execution mechanisms. *Cancer Lett* 1997;115(2):185-93.

Grimm et al., Fatality in mice due to oversaturation of cellular microRNA1short hairpin RNA pathways. *Nature* 2006;441(7092):537-41.

Grossmann et al., Apoptotic signalling during initiation of detachment-induced apoptosis ("anoikis") of primary human intestinal epithelial cells. *Cell Growth Differ* 2001;12(3):147-55.

Hajra and Liu, Apoptosome dysfunction in human cancer. *Apoptosis* 2004;9:691-704.

Hoffman, The multiple uses of fluorescent proteins to visualize cancer in vivo. *Nat Rev Cancer* 2005;5(10):796-806.

Hyer et al., Downregulation of c-FLIP sensitizes DU145 prostate cancer cells to Fas-mediated apoptosis. *Cancer Biol Ther* 2002;1(4):401-6.

Irrnler et al., Inhibition of death receptor signals by cellular FLIP. *Nature* 1997;388(6638):190-5.

Jarrard et al., Methylation of the androgen receptor promoter CpG island is associated with loss of androgen receptor expression in prostate cancer cells. *Cancer Res* 1998;58(23):5310-4.

Jemal et al., Cancer statistics, 2006. *CA Cancer J Clin* 2006;56(2):106-30.

Jiang et al., Caspases as key executors of methyl selenium-induced apoptosis (anoikis) of DU-145 prostate cancer cells. *Cancer Res* 2001;61(7):3062-70.

Jin et al., Overview of cell death signalling pathways. *Cancer Biol Ther* 2005;4(2):139-63.

Kharbanda et al., Role for Bcl-XL as an inhibitor of cytosolic cytochrome C accumulation in DNA damage-induced apoptosis. *Proc. Natl. Acad. Sci. USA* 1997;94:6939-42.

Kim et al., An inducible pathway for degradation of FLIP protein sensitizes tumor cells to TRAIL-induced apoptosis. *J Biol Chem* 2002;277(25):22320-9.

Kimura et al., Androgen blocks apoptosis of hormone-dependent prostate cancer cells. *Cancer Res* 2001;61(14):5611-8.

Kischkel et al., Cytotoxicity-dependent APO-1 (Fas/CD95)-associated proteins form a death-inducing signalling complex (DISC) with the receptor. *Embo J* 1995;14(22):5579-88.

Krueger et al., FLICE-inhibitory proteins: regulators of death receptor-mediated apoptosis. *Mol Cell Biol* 2001;21(24):8247-54.

Kuwana et al., Apoptosis induction by caspase-8 is amplified through the mitochondrial release of cytochrome c. *J Biol Chem* 1998;273(26):16589-94.

Lapointe et al., Gene expression profiling identifies clinically relevant subtypes of prostate cancer. *Proc Natl Acad Sci USA* 2004;101(3):811-6.

Marsden, RNA interference as potential therapy—not so fast. *N Engl J Med* 2006;355(9):953-4.

Medema et al., FLICE is activated by association with the CD95 death-inducing signalling complex (DISC). *Embo J* 1997;16(10):2794-804.

Mehlen et al., Metastasis: a question of life or death. *Nat Rev Cancer* 2006;6(6):449-58.

Minn et al., Genes that mediate breast cancer metastasis to lung. *Nature* 2005;436(7050):518-24.

Montel et al., FAS involvement in cytotoxicity mediated by human NK cells. *Cell Immunol.* 1995b;166:236-46.

Montel et al., FAS-mediated cytotoxicity remains intact in perforin and granzyme B antisense transfectants of a human NK-like cell line. *Cell Immunol.* 1995a;165:312-7.

Moreno et al., Circulating tumor cells predict survival in patients with metastatic prostate cancer. *Urology* 2005;65(4):713-8.

Muzio et al., FLICE, a novel FADD-homologous ICE-ICED-3-like protease, is recruited to the CD95 (FasIAPO-1) death—inducing signalling complex. *Cell* 1996;85(6):817-27.

Nagane et al., The potential of TRAIL for cancer chemotherapy. *Apoptosis* 2001;6:191-7.

Nishimura et al., Adenovirus-mediated transfection of caspase-8 augments anoikis and inhibits peritoneal dissemination of human gastric carcinoma cells. *Cancer Res* 2001;61(19):7009-14.

Pan et al., 5q11,8p117 and 10q22 are recurrent chromosomal breakpoints in prostate cancer cell lines. *Genes Chromosomes Cancer* 2001;30(2):187-95.

Pedersen et al., The triterpenoid CDDO induces apoptosis in refractory CLL B-cells. *Blood* 2002;100:2965-72.

Perlman et al., FLICE-inhibitory protein expression during macrophage differentiation confers resistance to fas-mediated apoptosis. *J Exp Med* 1999;190(11):1679-88.

Reed, Drug Insight: cancer therapy strategies based on restoration of endogenous cell death mechanisms. *Nat Clin Pract Oncol* 2006;3(7):388-98.

Rennebeck et al., Anoikis and survival connections in the tumor microenvironment: is there a role in prostate cancer metastasis? *Cancer Res* 2005;65(24):11230-5.

Rosen et al., Activated Ras prevents downregulation of Bcl-X(L) triggered by detachment from the extracellular matrix. A mechanism of Ras-induced resistance to anoikis in intestinal epithelial cells. *J Cell Biol* 2000;149(2):447-56.

Rosen et al., Cell detachment triggers p38 mitogen-activated protein kinase-dependent overexpression of Fas ligand. A novel mechanism of Anoikis of intestinal epithelial cells. *J Biol Chem* 2002;277(48):46123-30.

Rosen et al., Transforming growth factor-alpha prevents detachment-induced inhibition of c-Src kinase activity, Bcl-XL down-regulation, and apoptosis of intestinal epithelial cells. *J Biol Chem* 2001;276(40):37273-9.

Rytomaa et al., Involvement of FADD and caspase-8 signalling in detachment-induced apoptosis. *Curr Biol* 1999;9(18):1043-6.

Sayers et al., Molecular mechanisms of immune-mediated lysis of murine renal cancer: differential contributions of perforindependent versus FAS-mediated pathways in lysis by NK and T cells. *J. Immunol.* 1998;161:3957-65.

Scaffidi et al., The role of c-FLIP in modulation of CD95-induced apoptosis. *J Biol Chem* 1999;274(3):1541-8.

Scaffidi et al., The role of c-Flip in modulation of CD95-induced apoptosis. *J. Biol. Chem.* 1999;274:1541-8.

Scaffidi et al., Two CD95 (APO-1/FAS) signaling pathways. *EMBO J.* 1998;17:1675-87.

Schimmer et al., Receptor- and mitochondrial-mediated apoptosis in acute leukemia: A translational view. *Blood* 2001;98:3541-53.

Schimmer et al., Small-molecule antagonists of apoptosis suppressor XIAP exhibit broad antitumor activity. *Cancer Cell* 2004;5:25-35.

Schimmer, inhibitor of apoptosis proteins: translating basic knowledge into clinical practice. Cancer Res 2004;64(20):7183-90.

Schimmer et al., Identification of small molecules that sensitize resistant tumor cells to tumor necrosis factor-family death receptors. *Cancer Res* 2006;66(4):2367-75.

Shimada et al., Specific positive and negative effects of FLIP on cell survival in human prostate cancer. *Carcinogenesis* 2006;27(7):1349-57.

Shirasawa et al., Altered growth of human colon cancer cell lines disrupted at activated Ki-ras. *Science* 1993;260(5104):85-8.

Slee et al., Ordering the cytochrome c-initiated caspase cascade: hierarchical activation of caspases-2, -3, -6, -7, -8, and -10 in a caspase-9-dependent manner. *J Cell Biol* 1999;144(2):281-92.

Takeda et al., Involvement of tumor necrosis factor-related apoptosis-inducing ligand in surveillance of tumor metastasis by liver natural killer cells. *Nat. Med.* 2001;7:94-100.

Thome et al., Regulation of lymphocyte proliferation and death by FLIP. *Nat Rev Immunol* 2001;1(1):50-8.

van't Veer et al., Gene expression profiling predicts clinical outcome of breast cancer. *Nature* 2002;415(6871):530-6.

Varambally et al., Integrative genomic and proteomic analysis of prostate cancer reveals signatures of metastatic progression. *Cancer Cell* 2005;8(5):393-406.

Wang and El-Deiry, TRAIL and apoptosis induction by TNF-family death receptors. *Oncogene* 2003;22:8628-33.

Wuchter et al., In vitro susceptibility to TRAIL induced apoptosis of acute leukemia cells in the context of TRAIL receptor gene expression and constitutive NF-kappa B activity. *Leukemia* 2001;15:921-8.

Yeh et al., Expression of fas ligand in metastatic prostatic carcinoma: suggestive of possible clonal expansion of subpopulation with metastatic potential. *Diagn Mol Pathol* 2001;10(4):236-41.

Yu et al., Gene expression alterations in prostate cancer predicting tumor aggression and preceding development of malignancy. *J Clin Oncol* 2004;22(14):2790-9.

Zhou et al., Signal transduction targets in androgen-independent prostate cancer. *Cancer Metastasis Rev* 2001;20(3-4):351-62.

Zhou et al., Target protease specificity of the viral serpin CrmA: analysis of five caspases. *J. Biol. Chem.* 1997;272:7797-800.

Zhu et al., Anoikis and metastatic potential of cloudman S91 melanoma cells. *Cancer Res* 2001;61(4):1707-16.

All publications, patents and patent applications are incorporated herein by reference. While in the foregoing specification, this invention has been described in relation to certain preferred embodiments thereof, and many details have been set forth for purposes of illustration, it will be apparent to those skilled in the art that the invention is susceptible to additional embodiments and that certain of the details herein may be varied considerably without departing from the basic principles of the invention.

What is claimed:

1. A method to enhance TNF-family death receptor ligand-mediated killing of tumor cells in a mammal, comprising administering to a mammal having TNF-family death receptor ligand-resistant cancer an effective amount of a compound of formula (I):

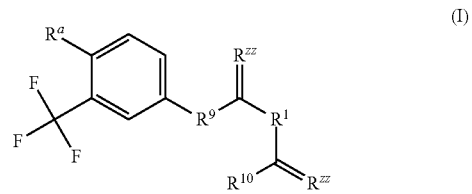

wherein,
$R^1$ is alkylene, alkenylene, arylene, heteroarylene, heterocyclene or cycloalkylene;
$R^a$ is F, Cl, Br or I;
$R^9$ is O or $NR^x$;
each $R^{zz}$ is independently O, $NR^x$ or S;
$R^{10}$ is alkyl, alkenyl, alkoxy, halo, haloalkyl, hydroxy, hydroxyalkyl, heteroaryl, heterocycle, cycloalkyl, amino, alkylamino, $NR^xR^y$ or $COOR^x$; and
each $R^x$ and $R^y$ is independently H, alkyl, alkenyl, aryl, heteroaryl, heterocycle, cycloalkyl or hydroxyl;
or a pharmaceutically acceptable salt thereof.

2. The method of claim 1 further comprising administering an effective amount of a TNF-family death receptor ligand.

3. The method of claim 2 wherein the compound and the ligand are administered at the same time.

4. The method of claim 2 wherein the compound is administered before the ligand.

5. The method of claim 2 wherein the compound is administered after the ligand.

6. A method to inhibit TNF-family death receptor ligand-resistant cancer in a mammal, comprising identifying a mammal having TNF-family death receptor ligand-resistant cancer; and administering to the mammal an effective amount of a compound of formula (I):

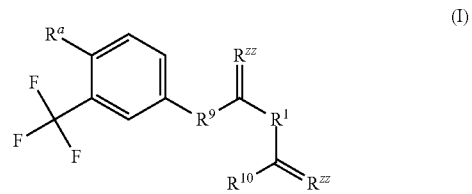

wherein,
$R^1$ is alkylene, alkenylene, arylene, heteroarylene, heterocyclene or cycloalkylene;
$R^a$ is F, Cl, Br or I;
$R^9$ is O or $NR^x$;
each $R^{zz}$ is independently O, $NR^x$ or S;
$R^{10}$ is alkyl, alkenyl, alkoxy, halo, haloalkyl, hydroxy, hydroxyalkyl, heteroaryl, heterocycle, cycloalkyl, amino, alkylamino, $NR^x R^y$ or $COOR^x$; and
each $R^x$ and $R^y$ is independently H, alkyl, alkenyl, aryl, heteroaryl, heterocycle, cycloalkyl or hydroxyl;
or a pharmaceutically acceptable salt thereof.

7. The method of claim 6 further comprising administering a TNF-family death receptor ligand.

8. The method of claim 7 wherein the compound and the ligand are administered at the same time.

9. The method of claim 7 wherein the compound is administered before the ligand.

10. The method of claim 7 wherein the compound is administered after the ligand.

11. A method to sensitize prostate cancer, breast cancer or ovarian cancer cells that are resistant to TNF-family death receptor ligand-mediated killing comprising contacting the cells with an effective amount of a compound of formula (I):

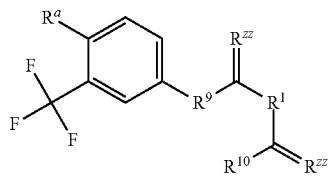

(I)

wherein, $R^1$ is alkylene, alkenylene, arylene, heteroarylene, heterocyclene or cycloalkylene;

$R^a$ is F, Cl, Br or I;

$R^9$ is O or $NR^x$;

each $R^{zz}$ is independently O, $NR^x$ or S;

$R^{10}$ is alkyl, alkenyl, alkoxy, halo, haloalkyl, hydroxy, hydroxyalkyl, heteroaryl, heterocycle, cycloalkyl, amino, alkylamino, $NR^xR^y$ or $COOR^x$; and each $R^x$ and $R^y$ is independently H, alkyl, alkenyl, aryl, heteroaryl, heterocycle, cycloalkyl or hydroxyl;

or a pharmaceutically acceptable salt thereof.

12. The method of claim 11 wherein the cells are contacted with the compound ex vivo.

13. The method of claim 11 further comprising contacting the cells with an effective amount of a TNF-family death receptor ligand.

14. The method of claim 11 wherein the cells are contacted with the compound and the ligand at the same time.

15. The method of claim 13 wherein the cells are contacted with the compound before the cells are contacted with the ligand.

16. The method of claim 13 wherein the cells are contacted with the compound after the cells are contacted with the ligand.

17. A method to inhibit metastases comprising administering to a mammal having TNF-family death receptor ligand-resistant cancer an effective amount of a compound of formula (I):

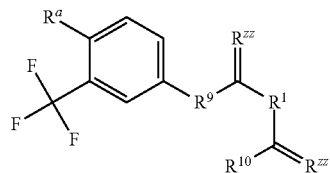

(I)

wherein, $R^1$ is alkylene, alkenylene, arylene, heteroarylene, heterocyclene or cycloalkylene;

$R^a$ is F, Cl, Br or I;

$R^9$ is O or $NR^x$;

each $R^{zz}$ is independently O, $NR^x$ or S;

$R^{10}$ is alkyl, alkenyl, alkoxy, halo, haloalkyl, hydroxy, hydroxyalkyl, heteroaryl, heterocycle, cycloalkyl, amino, alkylamino, $NR^xR^y$ or $COOR^x$; and each $R^x$ and $R^y$ is independently H, alkyl, alkenyl, aryl, heteroaryl, heterocycle, cycloalkyl or hydroxyl;

or a pharmaceutically acceptable salt thereof.

18. A method to sensitize cells to anoikis, comprising administering to a mammal having TNF-family death receptor ligand-resistant cancer an effective amount of a compound of formula (I):

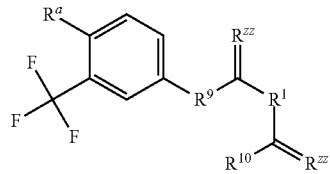

(I)

wherein, $R^1$ is alkylene, alkenylene, arylene, heteroarylene, heterocyclene or cycloalkylene;

$R^a$ is F, Cl, Br or I;

$R^9$ is O or $NR^x$;

each $R^{zz}$ is independently O, $NR^x$ or S;

$R^{10}$ is alkyl, alkenyl, alkoxy, halo, haloalkyl, hydroxy, hydroxyalkyl, heteroaryl, heterocycle, cycloalkyl, amino, alkylamino, $NR^xR^y$ or $COOR^x$; and each $R^x$ and $R^y$ is independently H, alkyl, alkenyl, aryl, heteroaryl, heterocycle, cycloalkyl or hydroxyl;

or a pharmaceutically acceptable salt thereof.

19. The method of claim 1, 6, 11, 17 or 18 wherein $R^a$ is Cl.

20. The method of claim 1, 6, 11, 17 or 18 wherein $R^9$ is $NR^x$.

* * * * *